(12) United States Patent
Rubinstein et al.

(10) Patent No.: US 10,806,711 B2
(45) Date of Patent: *Oct. 20, 2020

(54) METHOD OF TREATING ACUTE DECOMPENSATED HEART FAILURE WITH PROBENECID

(75) Inventors: Jack Rubinstein, Cincinnati, OH (US); W. Keith Jones, Fort Thomas, KY (US)

(73) Assignee: University of Cincinnati, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 13/584,713

(22) Filed: Aug. 13, 2012

(65) Prior Publication Data

US 2013/0046021 A1  Feb. 21, 2013

Related U.S. Application Data

(60) Provisional application No. 61/522,940, filed on Aug. 12, 2011.

(51) Int. Cl.
*A61K 31/195* (2006.01)

(52) U.S. Cl.
CPC .................. *A61K 31/195* (2013.01)

(58) Field of Classification Search
CPC ................................................. A61K 31/195
(Continued)

(56) References Cited

U.S. PATENT DOCUMENTS 3,524,917 A   8/1970  Morgans et al.
4,544,371 A * 10/1985 Dormandy, Jr. .... A61M 5/1428
                                                        604/185
(Continued)

FOREIGN PATENT DOCUMENTS

JP   2009-149534   7/2009
JP   2009149534    7/2009
(Continued)

OTHER PUBLICATIONS

Bronsky, D. Dubin, A. and Kushner, DS., Diuretic action of benemid: its effect upon the urinary excretion of sodim, chloride, potassium and water in edematous subjects., Am. J. Med. Feb. 18, 1955 (2): 259-66.*

(Continued)

*Primary Examiner* — Shengjun Wang
(74) *Attorney, Agent, or Firm* — Wood Herron & Evans LLP

(57) ABSTRACT

Described are inventions directed to methods of treating a cardiac dysfunction in a subject that includes administering an amount of probenecid effective to treat a symptom of cardiac dysfunction. The probenecid may be administered in at least one of an injection, orally, or transdermally. The amount of probenecid is sufficient to result in an improved performance on a standardized 6 minute walk test, an improved New York Heart Association (NYHA) classification, a lower diuretic dose requirement, a lower serum BNP levels, a normalization of serum sodium concentrations, and combinations thereof. In an embodiment, probenecid is administered over a period of about 8 hours to about 24 hours. Probenecid may be used for short term treatments, i.e., less than a week, or it may be administered in a long term manner, i.e., over a period of weeks, months, or even years.

12 Claims, 31 Drawing Sheets

Specification includes a Sequence Listing.

(58) Field of Classification Search
USPC .......................................................... 514/562
See application file for complete search history.

(56) References Cited

U.S. PATENT DOCUMENTS

| | | | |
|---|---|---|---|
| 4,952,402 A | 8/1990 | Sparks et al. | |
| 4,965,282 A | 10/1990 | Takamura et al. | |
| 4,973,600 A | 11/1990 | Takamura et al. | |
| 5,407,935 A | 4/1995 | Bigge et al. | |
| 5,444,067 A | 8/1995 | Kivlighn et al. | |
| 5,767,119 A | 6/1998 | Bigge et al. | |
| 5,942,513 A | 8/1999 | Bigge et al. | |
| 6,221,856 B1 | 4/2001 | Traynor-Kaplan et al. | |
| 7,625,696 B2* | 12/2009 | Katano ............... | A61K 31/00 435/4 |
| 7,799,794 B2 | 9/2010 | Kivlighn et al. | |
| 7,915,012 B2 | 3/2011 | Hwang et al. | |
| 8,420,594 B2 | 4/2013 | Hulot et al. | |
| 2002/0103181 A1* | 8/2002 | Sen ..................... | A61K 9/205 514/200 |
| 2003/0212123 A1 | 11/2003 | DeMello et al. | |
| 2004/0067954 A1 | 4/2004 | Eggenweiler et al. | |
| 2005/0182011 A1* | 8/2005 | Olson et al. ..................... | 514/44 |
| 2006/0035840 A1 | 2/2006 | Fujikura et al. | |
| 2007/0185197 A1 | 8/2007 | Fujikura et al. | |
| 2007/0212366 A1 | 9/2007 | Greinacher et al. | |
| 2008/0051428 A1 | 2/2008 | Davis et al. | |
| 2008/0188426 A1 | 8/2008 | Fushimi et al. | |
| 2008/0207763 A1 | 8/2008 | Gulati | |
| 2009/0017015 A1 | 1/2009 | Hughes | |
| 2009/0215107 A1 | 8/2009 | Hwang et al. | |
| 2010/0056464 A1 | 3/2010 | Gunic et al. | |
| 2010/0160351 A1* | 6/2010 | Jenkins ............... | A61K 31/167 514/262.1 |
| 2010/0160367 A1* | 6/2010 | Davis et al. ................... | 514/292 |
| 2010/0290998 A1 | 11/2010 | Jones et al. | |
| 2010/0292755 A1* | 11/2010 | Jones et al. ..................... | 607/46 |
| 2013/0046021 A1 | 2/2013 | Rubinstein et al. | |

FOREIGN PATENT DOCUMENTS

| | | |
|---|---|---|
| JP | 2009149534 A | 7/2009 |
| JP | 2009-535410 | 10/2009 |
| JP | 2009-535410 A | 10/2009 |
| WO | WO 2007130509 | 11/2007 |

OTHER PUBLICATIONS

Mylan Pharmaceuticals Inc., Morgantown, WV 26505, Mar. 2006. Probenecid tablet, film coated—(Human Prescription Drug Label) (total 4 pages).*

Jin, Y. et al., Effect of Application Volume of Ethanol-Isopropyl Myrstate Mixed Solvent System on Permeation of Zidovudine and Probenecid Through Rat Skin. Drug Development and Industrial Pharmacy, 26(2), 193-198 (2000).*

Chiang, Chia-Whei N., and Benet, Leslie Z., Dose-Dependent Kinetics of Probenecid in Rhesus Monkeys—Infusion Studies. Pharmacology 28: 181-187 (1984).*

Medical Dictionary—(online resource, Free Online Medical Dictionary)—definition of extended-release (total one page).*

2010 Comprehensive Heart Failure Practice Guideline, Heart Failure Society of America, http://www.heartfailureguideline.org/diuretic_therapy/81.*

Chaing et. al. Pharmacology 28:181-187; 1984.*

Ryuji Inoue, et al., Circulation Research Jul. 21, 2006, p. 119-131.*

Bang, S. et al. "Transient receptor potential V2 expressed in sensory neurons is activated by probenecid," Neuroscience Letters, 425 (2007) pp. 120-125.*

Arslan, S. et al., Tex Heart Inst J 2007;34:166-9.*

Koch et al, Journal of Investigative Medicine, vol. 59, No. 4, Apr. 2011, Abstract No. 58.*

Goldhaber, J. et al., Role of IN.*

HFSA 2010 HF Guidelines, Journal of Cardiac Failure, vol. 16, No. 6, 2010.*

Joseph, et al,Tex Heart Inst J. 2009: 36(6): 510-520.*

Balis, et al., Cancer Chemother Pharmacol (2000), 45: 259-264.*

Reichlin et al. "Diagnostic and Prognostic value of Uric acid in Patients with acute Dyspnea," American Journal of Medicine, 2009, vol. 122, No. 11, pp. Article No. 1054.e7. BIOSIS Abstract, AN 2009:636384 (Year: 2009).*

Koch, Sheryl E., et al., Probenecid Improves Myocardial Function in an Ischemic Heart Disease Murine Model, Department of Internal Medicine, Division of Cardiovascular Diseases, University of Cincinnati, Cincinnati, Ohio.

Database WPI, Week 200947, Thomson Scientific, London, GB, 2 pages.

Fast, Vladimir G., et al., Simultaneous Optical Mapping of Transmembrane Potential and Intracellular Calcium in Myocyte Cultures, Journal of Cardiovascular Electrophysiology, May 2000, pp. 547-556, vol. 11, No. 5, University of Alabama, Birmingham, Alabama.

Hasinoff, Brian B., The Metabolites of the Cardioprotective Drug Dexrazoxane Do Not Protect Myocytes from Doxorubicin-Induced Cytotoxicity,Molecular Pharmacology, 2003, pp. 670-678, vol. 64, No. 3, The American Society for Pharmacology and Experimental Therapeutics, USA.

Erttmann, R.R., Kinetics and Inotropic Action of Probenecid in Guinea-Pig Heart In Vitro, Experientia, Apr. 25, 1978, pp. 1620-1621, vol. 34, issue 12, University of Hamburg, Hamburg, Germany.

Tsuji, Akira, et al., In Vivo Evidence for Carrier-Mediated Uptake of B-Lactam Antibiotics Through Organic Anion Transport Systems in Rat Kidney and Liver, The Journal of Pharmacology and Experimental Therapeutics, Jun. 9, 1989, pp. 315-320, vol. 253, No. 1, The American Society for Pharmacology and Experimental Therapeutics, USA.

Damm, K.H., et al., Interaction of Probenecid with Digitoxin Metabolism in Rats, Toxicology and Applied Pharmacology, Feb. 25, 1975, pp. 246-257, vol. 33, Academic Press, Inc.

Damm, Klaus-H., et al., The Effects of Probenecid on the In Vitro Absorption of Cardiac Glycosides, European Journal of Pharmacology, Apr. 18, 1974, pp. 157-163, vol. 28, North-Holland Publishing Company.

Vasko, Michael R., et al., Furosemide Absorption Altered in Decompensated Congestive Heart Failure, Annais of Internal Medicine, 1985, pp. 314-318, vol. 102, American College of Physicians.

Kramer, Bernhard K., et al., Diuretic Treatment and Diuretic Resistance in Heart Failure, American Journal of Medicine, 1999, pp. 90-96, vol. 106, Excerpta Medica, Inc.

Robbins, Nathan, et al., The History and Future of Probenecid, Cardiovasc Toxicol, 2012, pp. 1-9, vol. 12, Springer Science+Business Media, LLC.

Koch, Sheryl E., et al., Probenecid: Novel Use As a Non-injurious Positive Inotrope Acting Via Cardiac TRPV2 Stimulation, Mar. 26, 2012, Department of Internal Medicine, Division of Cardiovascular Diseases, University of Cincinnati, Cincinnati, Ohio.

Bronsky, David, et al.,. Diuretic Action of Benemid, Its Effect Upon the Urinary Excretion of Sodium, Chloride, Potassium and Water in Edematous Subjects, American Journal of Medicine, Feb. 1955, pp. 259-266.

Anjak, A., et al., Transient Receptor Potential Vanilloid 2 (TRPV2) Stimulation Is Cardioprotective, Journal of Investigative Medicine, Apr. 23, 2010, vol. 58, No. 4, Lippincott Williams & Wilkens, US.

International Preliminary Report on Patentability issued by the International Bureau of WIPO in corresponding PCT Application No. PCT/US2014/025930 dated Sep. 15, 2015, 6 pages.

Rajesh M etal, Cannabidiol Attenuates Cardiac Dysfunction, Oxidative Stress, Fibrosis, and Inflammatory and Cell Death Signaling Pathways in Diabetic Cardiomyopathy, Journal of the American College of Cardiology, Elsevier, NY, vol. 56, No. 25, Dec. 14, 2010, pp. 2115-2125.

Anjak et al., Transient Receptor Potential Vanilloid 2 (TRPV2) Stimulation Is Cardioprotective, Journal of Investigative Medicine, Apr. 23, 2010, vol. 58, No. 4, Lippincott Williams & Wilkens, US.

(56) References Cited

OTHER PUBLICATIONS

Arslan et al., Prognostic Value of 6-Minute Walk Test, Tex Heart Inst J 2007; vol. 34:166-169.
Bang et al., Transient receptor potential V2 expressed in sensory neurons is activated by probenecid, Neuroscience Letters, 425 (2007) 120-125.
Bronsky et al., Diuretic Action of Benemid, Its Effect Upon the Urinary Excretion of Sodium, Chloride, Potassium and Water in Edematous Subjects, American Journal of Medicine, 18, Feb. 1955, 259-266.
Caterina, A capsaicin-receptor homologue with a high threshold for noxious heat. Nature, 1999; 398: 436-441.
Chiang et al., Dose-Dependent Kinetics of Probenecid in Rhesus Monkeys—Intravenous Bolus Studies, Pharmacology 23, 326-336, 1981.
Chiang et al., Dose-Dependent Kinetics of Probenecid in Rhesus Monkeys—Infusion Studies, Pharmacology 28: 181-187, 1984.
Damm et al., Interaction of Probenecid with Digitoxin Metabolism in Rats, Toxicology and Applied Pharmacology, Feb. 25, 1975, 246-257, vol. 33, Academic Press, Inc.
Damm et al., The Effects of Probenecid on the In Vitro Absorption of Cardiac Glycosides, European Journal of Pharmacology, Apr. 18, 1974, 157-163, vol. 28, North-Holland Publishing Company.
Database WPI, Week 200947, Thomson Scientific, London, GB, 2 pages, 2009.
Erttmann, Kinetics and Inotropic Action of Probenecid in Guinea-Pig Heart In Vitro, Experientia, Apr. 25, 1978, 1620-1621, vol. 34, issue 12, University of Hamburg, Hamburg, Germany.
Etsuko et al., Regulation of Calcium-Permeable TRPV2 Channel by Insulin in Pancreatic ?-Cells. Diabetes. Jan. 2009 vol. 58 No. 1 174-184.
Fast et al., Simultaneous Optical Mapping of Transmembrane Potential and Intracellular Calcium in Myocyte Cultures, Journal of Cardiovascular Electrophysiology, May 2000, 547-556, vol. 11, University of Alabama, Birmingham AL.
Haghighi, Superinhibition of Sarcoplasmic Reticulum Function by Phospholamban Induces Cardiac Contractile Failure* Jun. 29, 2001, The Journal of Biological Chemistry, 276, 24145-24152.
Hasinoff, The Metabolites of the Cardioprotective Drug Dexrazoxane Do Not Protect Myocytes from Doxorubicin-Induced Cytotoxicity, Molecular Pharmacology, 2003, pp. 670-678, vol. 64, No. 3, The American Society for Pharmacology and Experimental Therapeutics, USA.
Iwata et al., A novel mechanism of myocyte degeneration involving the Ca21-permeable growth factor-regulated channel. (2003) Journal of Cellular Biology. 161:957-967.
Inoeu et al., Transient receptor potential Channels in cardiovascular function and disease, Circulation Research, Jul. 21, 2006, pp. 119-131.
International Preliminary Report on Patentability issued by the International Bureau of WIPO in corresponding PCT Application No. PCT/US2014/025930 dated Sep. 15, 2015, 5 pages.
International Searching Authority, International Search Report and Written Opinion in corresponding application No. PCT/US2012/060990, dated Jan. 22, 2013, 9 pages.
Jin et al. Effect of Application Volume of Ethanol-Isopropyl Myrstate Mixed Solvent System on Permeation of Zidovudine and Probenecid through Rat Skin. Drug Development and Industrial Pharmacy, 26(2), 193-198 (2000).
Kamouh et al., Contemporary Management and Research Directions in Advanced Heart Failure: Where Are We Going? Congest Heart Fail. 2011; 17: 241-7.
Koch et al., Probenecid: Novel use as a non-injurious positive inotrope acting via cardiac TRPV2 stimulation, Jul. 2012, Department of Internal Medicine, Division of Cardiovascular Diseases, University of Cincinnati, Cincinnati, Ohio, (53), 134-144.
Kramer et al., Diuretic Treatment and Diuretic Resistance in Heart Failure, American Journal of Medicine, 1999, 90-96, vol. 106, Excerpta Medica, Inc.
Medical Dictionary (online, Free Online Medical Dictionary)—definition of 'extended release' (one page).
Monet, Lysophospholipids stimulate prostate cancer cell migration via TRPV2 channel activation. Biochimica et BiophysicaActa 1793 (2009) 528-539.
Muraki et al., TRPV2 is a component of osmotic sensitive cation channels in murine aortic myocytes. Circulation Research 2003;93: 829-838.
Orengo et al., "A bichromatic fluorescent reporter for cell-based screens of alternative splicing"; Nucleic Acids Research; 34(22):e148. Epub (Nov. 16, 2006).
Packer et al., Effect of Oral Milrinone on Mortality in Severe Chronic Heart Failure. NEngl J Med 1991; 325:1468-1475.
Rajesh et al, Cannabidiol Attenuates Cardiac Dysfunction, Oxidative Stress, Fibrosis, and Inflammatory and Cell Death Signaling Pathways in Diabetic Cardiomyopathy, Journal of the American College of Cardiology, Elsevier, NY, vol. 56, Dec. 14, 2010, 2115-2125.
Robbins et al., The History and Future of Probenecid, Cardiovasc Toxicol, 2012, 1-9, vol. 12, Springer Science+Business Media, LLC.
Shibasaki et al., (2010) TRPV2 enhances axon outgrowth through its activation by membrane stretch in developing sensory and motor neurons. J Neuroscience 30:4601-12.
Tsuji et al., In Vivo Evidence for Carrier-Mediated Uptake of B-Lactam Antibiotics Through Organic Anion Transport Systems in Rat Kidney and Liver, Journal of Pharmacology and Experimental Therapeutics, Jun. 9, 1989, 315-320, vol. 253.
Vasko et al., Furosemide Absorption Altered in Decompensated Congestive Heart Failure, Annals of Internal Medicine, 1985, pp. 314-318, vol. 102, American College of Physicians.
Yang et al., Functional expression of transient receptor potential melastatin- and vanilloid-related channels in pulmonary arterial and aortic smooth muscle. American Journal of Physiology Lung Cell Molecular Physiology 2006; 290: L1267-1276.
Global status report on noncommunicable diseases 2010. Geneva, World Health Organization, 2011.
Global atlas on cardiovascular disease prevention and control. Geneva, World Health Organization, 2011.
Kochanek et al. Deaths: final data for 2009. National vital statistics reports 2011;60(3).
Burger et al. Comparison of the occurrence of ventriculary arrhtyhmias in patients with acutely decompensated congestive heart failure receiving dobutamine versus nesiritide therapy. Am J Cardiol 2001;88(1):35-39.
Singh et al. Adrenergic Regulation of Cardiac Myocyte Apoptosis. J Cell Physiol 2001;189(3):257-265.
Kunert-Keil et al. Tissue-specific expression of TRP channel genes in the mouse and its variation in three different mouse strains. BMC Genomics 2006;7:159.
Koch et al. Probenecid as a non-injurious positive inotrope in an ischemic heart disease murine model. J Cardiovas Pharm Ther 2012;18(3):280-289.
Livak and Schmittgen. Analysis of relative gene expression data using real-time quantitative PCR and the 2(-Delta Delta C(T)) Method. Methods 2001;25:402-408.
Pfaffl. A new mathematical model for relative quantification in real-time RT-PCR. Nucleic Acids Res 2001;29:e45.
Lang et al. Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology. Chamber Quantification Writing Group; American Society of Echocardiography's Guidelines and Standards Committee; European Association of Echocardiography. J Am Soc Echocardiogr 2005;18(12):1440-1463.
Barrio-Soria et al. Angiotensin-2-Mediated Ca2+ Signaling in the Retinal Pigment Epithelium: Role of Angiotensin-Receptor-Associated-Protein and TRPV2 Channel. PLoS ONE 2012;7(11):e49624.

(56) References Cited

OTHER PUBLICATIONS

Park et al. TRP vanilloid 2 knock-out mice are susceptible to perinatal lethality but display normal thermal and mechanical nociception. J Neurosci. Aug. 10, 2011;31(32):11425-36. doi: 10.1523/JNEUROSCI.1384-09.2011.

Hisanaga et al. Regulation of calcium-permeable TRPV2 channel by insulin in pancreatic beta-cells. Diabetes. Jan. 2009;58(1):174-84. doi: 10.2337/db08-0862. Epub Nov. 4, 2008.

Mihara et al. TRPV2 ion channels expressed in inhibitory motor neurons of gastric myenteric plexus contribute to gastric adaptive relaxation and gastric emptying in mice. Am J Physiol Gastrointest Liver Physiol 2013;304(3):G235-G240.

Beyer, R.H., et al., "'Benemid,' p-(di-n-Propylsulfamyl)-Benzoic Acid: Its Renal Affinity and Its Elimination"; The American Journal of Physiology; vol. 166, Issue 3; pp. 625-640 (Sep. 1951).

Bishop and Pfaff., "Immediate Uricosuric Effect of Probenecid in Normal Humans"; Proc. Soc. Exp. Biol. Med. 88 (1955) 346-48.

Boger et al., "Benemid and Carinamide: Comparison of Effect on Para-Aminosalicylic Acid (PAS) Plasma Concentrations"; Journal of Laboratory and Clinical Medicine, 36; pp. 276-282 (Apr. 28, 1950).

Boger et al., "Toxicity of Carinamide", A Review of 1,997 Patients, American Journal of Medicine; pp. 35-43 (Jul. 1950).

Boger et al., "Probenecid (Benemid): Its uses and side effects in 2502 Patients"; AMA Arch Intern Med. 95(1); pp. 83-92 (1955).

Forbes, et al., "The Transport of Organic Anions by the Rabbit Eye. II. In vivo transport of iodopyracet (Diodrast)"; Am J Ophthalmol; 50. pp. 867-875 (1960).

Gutman, et al., "Benemid (p-di-n-propylsulfamyl)-benzoic acid) as Uricosuric Agent in Chronic Gouty Arthritis"; Trans Assoc. Am Physicians; 64:279-288 (1951).

Kahn et al.; "Urate Transport in the Proximal Tubule: In vivo and in vesicle studies"; American Journal of Physiology; 249:F789-F798 (1985).

Koch et al., "Probenecid Increases Myocardial Contractility without Worsening Ischemic Damaga in an Infarct Model"; Abstract; The American Federation for Medical Research; p. 709 (2011).

Korf et al., "The Intravenous Probenecid Test: a Possible Aid in Evaluation of the Serotonin Hypothesis on the Pathogenesis of Depressions"; Psychopharmacologia. 18(1); pp. 129-132 (1970).

Nagasawa et al., "Chemotactic Peptide fMetLeuPhe Induces Translocation of the TRPV2 Channel in Macrophages"; Journal of Cellular Physiology, vol. 210, Issue 3, pp. 692-702, (Mar. 2007).

O'Connell et al., "Isolation and Culture of Adult Mouse Cardiac Myocytes"; Methods in Molecular Biology, vol. 357, pp. 271-296 (2007).

Wolf et al., "Pharmacokinetics and renal effects of cidofovir with a reduced dose of probenecid in HIV-infected patients with cytomegalovirus retinitis"; J ClinPharmacol. 43(1); pp. 43-51 (2003).

Anjnk et al., Journal of Investigative Medicine, Apr. 2010, vol. 58, No. 4, p. 652.

Koch et al, Journal of Investigative Medicine, Apr. 2011, vol. 59, No. 4, p. 709.

JP Action issued in corresponding Appln. No. 2015-527439, dated Apr. 10, 2017.

Bronsky, M.D., David et al.; "Diuretic Action of Benemid"; American Journal of Medicine; vol. 18, pp. 259-266 (1955).

Journal of Investigative Medicine; Midwestern Regional Program Abstracts; vol. 58, No. 4; p. 652 (Apr. 2010).

Journal of Investigative Medicine; Midwestern Regional Program Abstracts; vol. 59, No. 4; p. 709 (Apr. 2011).

Koch, Sheryl E. et al.; "Probenecid: Novel use as a non-injurious positive inotrope acting via cardiac TRPV2 stimulation"; Journal of Molecular and Cellular Cardiology; vol. 53, No. 1; pp. 134-144 (Apr. 27, 2012).

JP, Notice of Reasons for Rejection, translated and original, issued in corresponding Japanese Application No. 2015-527439, 9 pages (dated Apr. 17, 2017).

Japanese Patent Office, Decision of Rejection issued in corresponding Japanese Application No. 2015-527439, dated Jan. 29, 2018, English translation only (7 pages).

Official Journal of the Japanese Circulation Society, JCS Guidelines for Treatment of Acute Heart Failure—Digest Version (JCS 2011), Circulation Journal vol. 77, Aug. 2013, in Japanese (41 pages) and in English (45 pages).

\* cited by examiner

METHOD OF TREATING ACUTE DECOMPENSATED HEART FAILURE WITH PROBENECID

RELATED APPLICATION

The Present application claims priority to U.S. Ser. No. 61/522,940 filed Aug. 12, 2011, the disclosure of which is hereby incorporated herein by reference in its entirety.

FIELD OF THE INVENTION

The present invention relates generally to treating cardiomyopathy, systolic cardiac dysfunction, and the symptoms of congestive heart failure with probenecid and it metabolites, and related chemical entities.

BACKGROUND OF THE INVENTION

Nearly six million people in the United States are living with the symptoms of congestive heart failure and other cardiac dysfunctions. The patients suffering from the symptoms of congestive heart failure are treated on an average with six different medications.

The current management of acute congestive heart failure is based on afterload reduction and increasing myocardial contractility. The therapies for the former are well established and include direct and indirect vasodilators, unfortunately the therapeutic options available for the latter are limited to digoxin and sympathomimetics (i.e dopamine, dobutamine, milrinone). The sympathomimetic drugs share the common endpoint of increasing cAMP production in the cardiomyocyte (either directly through β-ADR stimulation or indirectly via phosphodiesterase inhibition PDI) and have repeatedly been shown to be associated with poor outcomes. Several mechanisms have been shown to be related to the deleterious outcomes associated with these medications including arrhythmias, stimulation of apoptotic signaling and increased myocardial energetic demand. New ans safer therapies for congestive heart failure are needed, yet despite billions of dollars invested in the hunt to date, most candidates continue to focus upon the same pathways and have similar adverse effect profiles.

Probenecid is a highly lipid soluble benzoic acid derivative with an excellent safety profile that was developed in the 1950's to decrease the renal tubular excretion of penicillin; and has been used to increase the serum concentration of several antibiotics and antivirals since. It was also found to be a competitive inhibitor of active transport process in the brain, liver and eye and was studied in these fields but a clinical use was not established outside of its renal effects.

Not unlike other drugs that were developed to increase serum levels of antibiotics it was initially administered via slow intravenous infusion. Subsequently it was found to be rapidly absorbed following oral administration with peak serum concentrations occurring in 1 to 5 hours. Water soluble preparations of the drug were briefly available in the United States but the orally administered lipid soluble version is the only one currently available and FDA approved for the treatment of gout.

During the initial studies using probenecid (referred to as Benemid), probenecid was observed to have a strong uricosuric effect and quickly became the standard of treatment of gout. It was found to decrease uric acid levels in the serum via inhibition of organic acid reabsorption, such as uric acid, by the renal proximal tube by acting as a competitive inhibitor of the organic anion transporter (OAT) and thus preventing OAT-mediated reuptake of uric acid from the urine to the serum. Even though probenecid has a minimal adverse effect profile, its clinical use has declined significantly as other therapies for gout have shown improved efficacy.

Previously, the diurectic effects of probenecid was investigated patients suffering from "uncomplicated congestive heart failure." [Bronsky, et al., (1955) *Diuretic Action of [Probenecid]: Its Effects Upon The Urinary Excretion of Sodium, Chloride, Potassium, and Water In Edematous Subjects*, Am. J. Med. 18, pp. 259-266 and Kushner, et al., (1954) *Effect of [Probenecid] On Excretion of Water, Sodium, and Chloride In Congestive Heart Failure*, Federation Proceedings, 13, p. 435.] In those investigations, a large dose of probenecid, 2 g/day or 4 g/day was given orally to subjects with uncomplicated congestive heart failure over a period of several days, with the explicit goal of evaluating the potential renal effects of probenecid. Those studies found that probenecid had a strong diuretic effect that was attributed to the renal aspect of probenecid and not any potential cardiac effect as the technology.

Research interest in probenecid has recently increased with the finding that it is a selective agonist of transient receptor potential vanilloid 2 (TRPV 2). The TRP family of ion channels has been studied for many years in the nephrology and neurology literature. Several TRPs have also been found to be important mediators of vascular tone (TRPC1, TRPVc6 and TRPM4), cerebral blood flow (TRPM4), neointimal hyperplasia (TRPC1), and pulmonary hypertension (TRPC6). But until recently, only a few of the channels (such as TRPC3/6/7 in the development of cardiac hypertrophy in response to pressure overload) in this family have been found to have direct cardiac effects. With regards to the TRPV family, there are very interesting studies that have found a direct cardiac effect. First, it was observed that cardiac specific overexpression of TRPV2 resulted in chamber dilation of all cavities of the murine heart. Subsequently, it was observed that TRPV1 knockout mice have increased infarct size and decreased survival after ligation of the left anterior descending artery in comparison to their wild type littermates. Interestingly, others have observed that TRPV 1 activation with specific agonists results in protection against ischemia/reperfusion (I/R) injury.

SUMMARY OF THE INVENTION

While the invention will be described in connection with certain embodiments, it will be understood that the invention is not limited to these embodiments. On the contrary, the invention includes all alternatives, modifications and equivalents as may be included within the spirit and scope of the present invention.

An aspect of the present invention is directed to a method of treating cardiomyopathy, systolic cardiac dysfunction, and the symptoms of congestive heart failure, collectively referred to herein as "cardiac dysfunction," in a subject that includes administering via intravenous administration an amount of probenecid effective to treat a cardiac dysfunction and the symptom of cardiac dysfunction. In one embodiment of the invention, probenecid is administered in a range of about 1 mg/kg/day to about 100 mg/kg/day. The probenecid may be administered in at least one of a bolus injection or continuous intravenous infusion, or a bolus (loading dose) followed by intravenous infusion. In an embodiment, probenecid is administered over a period of about 8 hours to about 24 hours. Probenecid may be used for short term treatments, i.e., less than a week, or it may be administered in a long term manner, i.e., over a period of weeks, months, or even years. Probenecid may be administered in an amount sufficient to improve cardiac function clinically, resulting in an improvement in the cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof.

Another aspect of the invention is direct to a method of treating a cardiac dysfunction and the symptom of cardiac dysfunction in a subject comprising administering via oral administration an amount of probenecid effective to treat a symptom of cardiac dysfunction. In an embodiment, probenecid is administered in a range of about 1 mg/kg/day to about 100 mg/kg/day. Probenecid may be administered in an immediately available formulation or in an extended release formulation. The extended release formulation is formulated to maintain a therapeutic blood plasma concentration of probenecid for a duration ranging between about 18 hours and about 24 hours. Probenecid may be used for short term treatments, i.e., less than a week, or it may be administered in a long term manner, i.e., over a period of weeks, months, or even years. Probenecid may be administered in an amount sufficient to improve cardiac function clinically, resulting in an improvement in the cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof.

BRIEF DESCRIPTION OF THE DRAWINGS

The accompanying figures, which are incorporated in and constitute a part of this specification, illustrate exemplary embodiments of the invention and, together with a general description of the invention given above, and the detailed description given below, serve to explain the principles of the invention.

DETAILED DESCRIPTION OF THE INVENTION

Figure 1A:
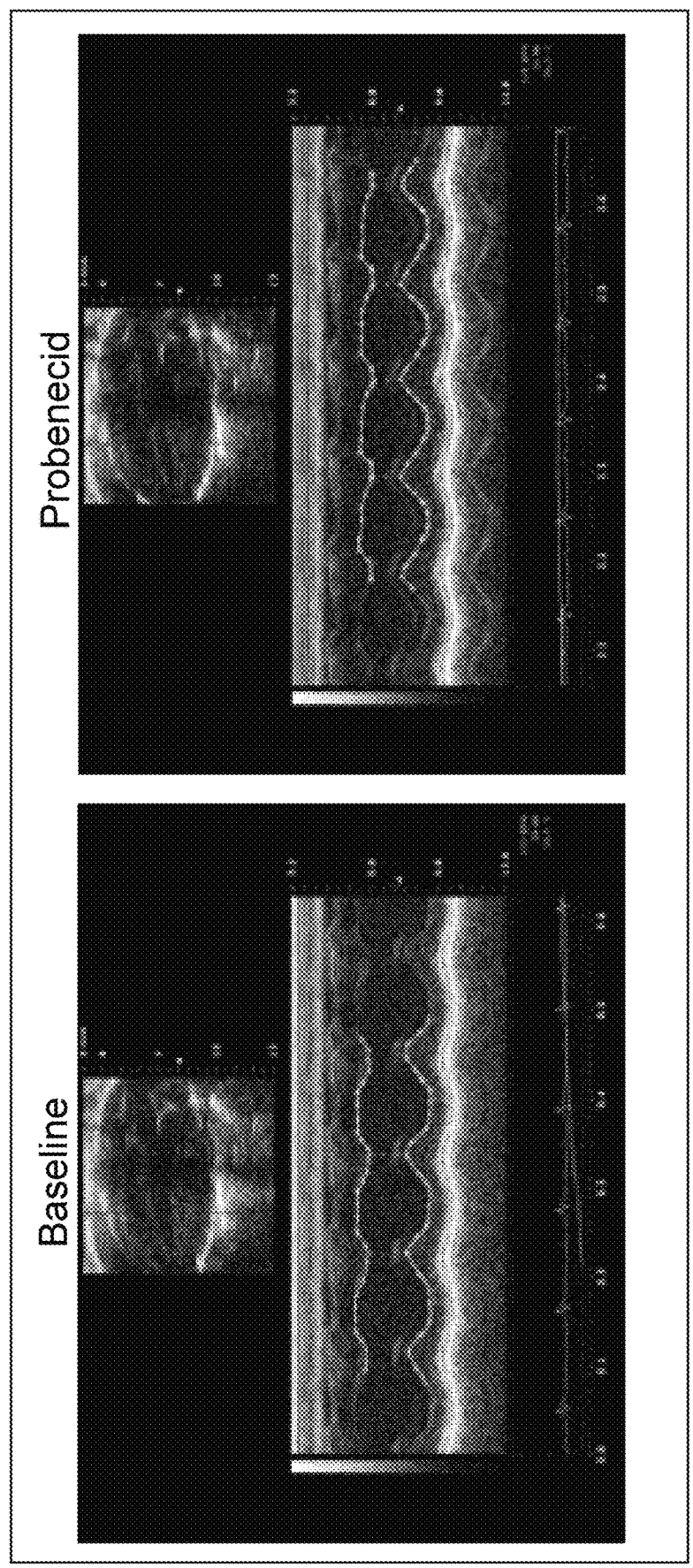
FIG. 1A is a representative B-mode and M-mode echocardiogram from long axis views for baseline and after administration of probenecid 200 mg/kg IV.

An aspect of the invention is directed to novel methods of treating cardiomyopathy, systolic cardiac dysfunction, and the symptoms of congestive heart failure, collectively referred to herein as "cardiac dysfunction," in a subject with probenecid. Probenecid has recently been identified as an agonist of the transient receptor potential vanilloid 2 (TRPV2) ion channel. TRPV2 is a weakly calcium-selective cation channel that is activated by swelling of cells and heat, in addition to specific agonists, like probenecid.

Without being bound to any particular theory, probenecid increases contractility in cardiac myocytes through dose dependent changes in myocyte calcium concentration and improved calcium handling by the cell. As illustrated in the data provided in Example 1, these processes are not mediated through beta-adrenergic receptor phosphorylation or ryanodine receptor or phospholamban. The effects mediated by probenecid do not induce cell death and is not associated with increased infarct size during simulated myocardial infarction, unlike clinically used sympathomimetics. Understanding the mechanism of action for the effects of probenecid, as demonstrated in Examples 2 and 3 allow for the surprising discovery that cardiac dysfunction and the symptom of cardiac dysfunction can be treated with probenecid and more particularly, lower doses of probenecid than is needed for the other uses and indeed lower the doses of probenecid used in previous studies of congestive heart failure. These observations resulted in novel treatments for subjects in acute crisis as well as the long term treatment of patients with therapeutically effective doses of probenecid.

As illustrated in the Examples, probenecid acts as a positive inotrope in a murine model of heart failure. Importantly, probenecid is more active in heart failure mice with low ejection fraction than in mice without heart failure. In the heart failure mice, probenecid normalizes the ejection fraction. Like murine cardiac tissue, human cardiac tissue also includes TRPV2 ion channels that can be targeted to treat cardiac dysfunction or the symptoms of cardiac dysfunction with probenecid.

When treating cardiac dysfunction or the symptoms of cardiac dysfunction, the therapeutically effective dose of probenecid is a dose that achieves levels of probenecid and its active metabolites in the plasma to increase the contractility of the heart such that the cardiac output is sufficient to alleviate at least some symptoms of cardiac dysfunction. For example, probenecid may be administered in an amount sufficient to improve cardiac function clinically, resulting in an improvement in the cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof.

An aspect of the invention is directed to a method of treating cardiac dysfunction or the symptoms of cardiac dysfunction in a subject comprising administering via injection a therapeutically effective amount of probenecid. In one embodiment, the injection is an intravenous administration. The dose required to adequately improve cardiac function in a given patient may vary widely due to titration required by the effectiveness of treatment and the rate of clearance. Thus, in one embodiment, probenecid is administered in a range from about 1 mg/kg/day to about 100 mg/kg/day. The term day is understood to be a 24 hour cycle. In another embodiment, the extended release formulation includes a total dose of probenecid in a range from about 1 mg/kg/day to about 50 mg/kg/day. In an alternative embodiment, the extended release formulation includes a total dose of probenecid in a range from about 1 mg/kg/day to about 25 mg/kg/day. In an embodiment, the therapeutically effective amount of probenecid is in a range from about 1 mg/kg/day to about 20 mg/kg/day. In another embodiment, the therapeutically effective amount of probenecid is in a range from about 5 mg/kg/day to about 50 mg/kg/day. In another embodiment, the therapeutically effective amount of probenecid has a dosage in the range of about 10 mg/kg/day to about 100 mg/kg/day. In another embodiment, the therapeutically effective amount of probenecid has a dosage in the range of about 50 mg/kg/day to about 100 mg/kg/day.

The injection of the therapeutically effective amount of probenecid may be administered in a bolus injection, by continuous infusion, or a combination of bolus injection and continuous infusion. The term bolus injection is understood to be an injection wherein the dose is delivered over a relatively short period of time. The term continuous infusion is understood to be an injection delivered, such as with an intravenous drip, wherein the dose is delivered in a metered manner over the period of time desired for probenecid therapy. In an embodiment, the probenecid is administered via continuous infusion over a period of time ranging between about 30 min/day to about 24 hours/day. In another embodiment, therapeutically effective amount of probenecid is administered over a period of about 8 hours/day to about 24 hours/day. In some circumstances, probenecid is administered via continuous drip on at least one day and up to on seven days. In other circumstances, probenecid may be administered for even longer periods of times, such as on days over multiple weeks, months, or even years, as necessary to treat the symptoms in the subject. Thus, embodiments of the invention are directed to the long term administration of probenecid to treat cardiac dysfunction and the symptoms of cardiac dysfunction.

In some instances a combination of bolus injection with continuous infusion may be desired to a treat a subject. For example, a bolus injection may be utilized to deliver a loading dose, i.e., a dose of probenecid to rapidly achieve a desired therapeutic level of probenecid in the subject, and the continuous infusion may be utilized to maintain or even titrate the desired therapeutic levels over the desired duration of treatment. For example, a subject in acute distress such as from decompensated congestive heart failure may require immediate treatment with a bolus intravenous injection of probenecid. After the initial bolus injection the subject may then require followed by maintenance administration or titration of probenecid such as via continuous infusion for a period of time thereafter. In the alternative, maintenance administration of probenecid may be accomplished with subsequent bolus injections. The continuous infusion of probenecid is also useful in treating subjects with compensated congestive heart failure or the other forms of cardiac dysfunction.

Another aspect of the invention is directed to a method of treating the cardiac dysfunction or the symptoms of cardiac dysfunction in a subject that includes administering via oral administration of a therapeutically effective dose of probenecid. In an embodiment, the therapeutically effective amount of probenecid is in a range from about 1 mg/kg/day to about 25 mg/kg/day. In another embodiment, the therapeutically effective amount of probenecid has a dosage in the range of about 5 mg/kg/day to about 25 mg/kg/day. In another embodiment, the therapeutically effective amount of probenecid has a dosage in the range of about 5 mg/kg/day to about 20 mg/kg/day. In another embodiment, the therapeutically effective amount of probenecid has a dosage in the range of about 5 mg/kg/day to about 15 mg/kg/day. This oral dose of probenecid may be administered in a single dose or multiple doses in a 24 hour period and may generally be administered for a period of days, weeks, months, or even years. In an embodiment, probenecid is orally administered to a subject over a period of at least two weeks, and in alternative embodiments, probenecid is administered for a plurality of months or a year or more. Thus, embodiments of the invention are directed to the long term administration of probenecid to treat cardiac dysfunction and the symptoms of cardiac dysfunction.

Another aspect of the invention is directed to a method of treating cardiac dysfunction or the symptoms of cardiac dysfunction in a subject that includes administering an extended release formulation of probenecid that maintains a therapeutic blood plasma concentration of probenecid and its active metabolites for a duration ranging between about 18 hours/day and about 24 hours/day. The extended release formulation may be an oral formulation, an injected formulation or even a transdermal formulation. In an embodiment, the extended release formulation includes a total dose of probenecid to improve cardiac function clinically, resulting in an improvement in the cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof. Probenecid dosing will require titration to achieve and maintain the desired effect. Thus, the dose required to adequately improve cardiac function may vary widely for a given subject as treatment progresses as well as between subjects. Thus, in one embodiment, probenecid is administered in a range from about 1 mg/kg/day to about 100 mg/kg/day. The term day is understood to be a 24 hour cycle. In another embodiment, the extended release formulation includes a total dose of probenecid in a range from about 1 mg/kg/day to about 50 mg/kg/day. In an alternative embodiment, the extended release formulation includes a total dose of probenecid in a range from about 1 mg/kg/day to about 25 mg/kg/day. In an embodiment, the therapeutically effective amount of probenecid is in a range from about 1 mg/kg/day to about 20 mg/kg/day. In another embodiment, the therapeutically effective amount of probenecid is in a range from about 5 mg/kg/day to about 50 mg/kg/day. In another embodiment, the therapeutically effective amount of probenecid has a dosage in the range of about 10 mg/kg/day to about 100 mg/kg/day. In another embodiment, the therapeutically effective amount of probenecid has a dosage in the range of about 50 mg/kg/day to about 100 mg/kg/day. In an embodiment, probenecid is orally administered to a subject over a period of at least two weeks, and in alternative embodiments, probenecid is administered for a plurality of months or a year or more. Thus, embodiments of the invention are directed to the long term administration of probenecid to treat cardiac dysfunction and the symptoms of cardiac dysfunction.

Another aspect of the invention is directed to a method of treating cardiac dysfunction or the symptoms of cardiac dysfunction in a subject comprising administering via transdermal administration, such as with a gel or patch, a therapeutically effective amount of probenecid. In one embodiment, the transdermal formulation maintains a therapeutic blood plasma concentration of probenecid and its active metabolites for a duration ranging between about 18 hours/day and about 24 hours/day. In an embodiment, the transdermal formulation includes a total dose of probenecid to improve cardiac function clinically, resulting in an improvement in the cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof. Probenecid dosing will require titration to achieve and maintain the desired effect. Thus, the dose required to adequately improve cardiac function may vary widely for a given subject as treatment progresses as well as between subjects. Thus, in one embodiment, probenecid is administered in a range from about 1 mg/kg/day to about 100 mg/kg/day. The term day is understood to be a 24 hour cycle. In another embodiment, the extended release formulation includes a total dose of probenecid in a range from about 1 mg/kg/day to about 50 mg/kg/day. In an alternative embodiment, the extended release formulation includes a total dose of probenecid in a range from about 1 mg/kg/day to about 25 mg/kg/day. In an embodiment, the therapeutically effective amount of probenecid is in a range from about 1 mg/kg/day to about 20 mg/kg/day. In another embodiment, the therapeutically effective amount of probenecid is in a range from about 5 mg/kg/day to about 50 mg/kg/day. In another embodiment, the therapeutically effective amount of probenecid has a dosage in the range of about 10 mg/kg/day to about 100 mg/kg/day. In another embodiment, the therapeutically effective amount of probenecid has a dosage in the range of about 50 mg/kg/day to about 100 mg/kg/day. In an embodiment, probenecid is transdermally administered to a subject over a period of at least a week, and in alternative embodiments, probenecid is administered for a plurality of months or a year or more. Thus, embodiments of the invention are directed to the long term administration of probenecid to treat cardiac dysfunction and the symptoms of cardiac dysfunction.

Achievement of a therapeutic blood plasma concentration may be evaluated by quantifying the clinical improvement in cardiac function of a subject such as with a standardized 6 minute walk test, improved New York Heart Association (NYHA) classification, lower diuretic dose requirement, lower serum BNP levels, normalization of serum sodium concentrations, and combinations thereof. Alternatively, levels of probenecid and its metabolites may be measured in the blood of a subject. For example, lowering the NYHA classification by 1, such as from 4 to 3, is a quantifiable improvement. While the extended release and the transdermal formulations may be used to rescue a subject suffering from decompensated congestive heart failure, these formulations are particularly useful for maintenance and titration of probenecid for subjects suffering from the cardiac dysfunction and the symptoms of cardiac dysfunction.

The dosing and routes of administration of probenecid may be combined to result in the optimal treatment of the subject. For example, probenecid may be administered as bolus therapy with a dose of 1/mg/kg up to 50 mg/kg in acutely ill subject with a cardiac dysfunction such as decompensated heart failure. If this treatment is sufficient to improve symptoms then the physician may chose to initiate a continuous infusion at a rate of 1 mg/kg/hr and up to 100 mg/kg/hr with titration as needed based on each individual scenario. Furthermore, some patients may require transition to parenteral probenecid which may be administered via gel form or scored capsules with a range of 200 mg/daily and up to 4 gr/daily.

Probenecid, as used herein, includes pharmaceutically acceptable salts of probenecid as well as, pro-drugs, isomers, and polymorphs, as well as derivatives that are structurally related to or derived from probenecid. The compositions of probenecid can be administered in vivo in a pharmaceutically acceptable carrier. By "pharmaceutically acceptable" is meant a material that is not biologically or otherwise undesirable. Thus, the compositions may be administered to a subject, without causing undesirable biological effects or interacting in a deleterious manner with any of the other components of the pharmaceutical composition in which it is contained. The carrier would naturally be selected to minimize any degradation of the probenecid and to minimize any adverse side effects in the subject, as would be known to one of skill in the art.

Suitable carriers and their formulations are described in Remington: The Science and Practice of Pharmacy (19th ed.) ed. A. R. Gennaro, Mack Publishing Company, Easton, Pa. 1995. For intravenous administration, an appropriate amount of a pharmaceutically-acceptable salt is used in the formulation to render the formulation isotonic. Examples of the pharmaceutically-acceptable carriers include, but are not limited to, saline, Ringer's solution and dextrose solution. The pH of the solution is in a pharmaceutically acceptable range, preferably from about 5 to about 8.5, and more preferably from about 7.8 to about 8.2. Further carriers include sustained release preparations such as semipermeable matrices of solid hydrophobic polymers containing the pharmaceutical composition, which matrices are in the form of shaped articles, e.g., films, liposomes or microparticles. It will be apparent to those persons skilled in the art that certain carriers may be more preferable depending upon, for instance, the route of administration and concentration of composition being administered. For example, persons skilled in the art may choose a particular carrier suitable for introduction to the body by injection, as described above, or ingestion.

In one embodiment, an injectable formulation of probenecid is prepared by dissolving probenecid powder (acid form) in 0.1 molar sodium hydroxide. This solution is then diluted with 0.2M phosphate buffer (pH=7.4). The probenecid is then diluted to a stock concentration, such as about 4.2 mg/ml with normal saline, or other carrier suitable for intravenous injection, to form a stock solution. The stock solution may then be diluted in saline or other injectable solution to the desired dose for administration.

For ingestion, probenecid may be formed into a tablet, capsulized, or dissolved or suspended in a liquid or gel as known to those of ordinary skill in the art for oral administration of a drug. In some embodiments, probenecid is formulated for sustained release, such as with the use of one or more excipients that control the release of probenecid over a specified period of time for absorption by the subject.

The pharmaceutical compositions of probenecid may also include binders, thickeners, diluents, buffers, preservatives, surface active agents, and the like in addition to the probenecid and carriers.

The disclosed compositions may be suitable for systemic administration. For example the compositions may be administered by other means known in the art, such as orally, parenterally (e.g., intravenous injection, intramuscular injection, intraperitoneal injection, or subcutaneous injection), suppository, or even transdermally such as through a gel or patch formulation. Such formulations may be prepared as described above or as is known to those of ordinary skill in the art.

EXAMPLE 1

A survey of murine and human myocardial tissue for expression of TRPV channels established that TRPV2 was the highest of these expressed in whole heart samples and specifically in the left ventricle. The present study investigates the cardiac effects of probenecid on the whole animal, isolated whole heart and the isolated ventricular myocyte to evaluate probenecid's ability to modulate myocardial function.

Methods

Animals—Wild type (WT) mice (B6129SF2/J F2 and C57BL6J, Jackson laboratories) and TRPV2$^{-/-}$ mice (breeding pairs provided by Dr. M. Caterina, John's Hopkins, Baltimore, Md.) were males at 12-16 weeks of age.

In vivo studies—Studies of contractility with intravenous administration of probenecid.

Echocardiographic evaluation. In order to obtain a dose response curve, male C57 WT (n=39) mice 12-16 weeks of age were anesthetized with isoflurane while intravenous jugular access (IV) was obtained under a microscope as previously described. Subsequently, an echocardiographic study with both M-mode and B-mode was obtained in parasternal long axis (PSLAX) as described below. Either saline or different doses of probenecid (increasing from 2 to 200 mg/kg) were injected (bolus IV) for the initial contractility studies in WT mice.

Invasive evaluation.—Once a dose range was established, a separate group of WT mice were anesthetized with an intraperitoneal injection of ketamine (50 μg/g) and inactin (thiobutabarbital, 100 μg/g, Sigma, Mass.). A tracheotomy was performed (PE-90), and body temperature was monitored and maintained with a feedback-controlled heating table. The right femoral artery was cannulated with fluid-filled polyethylene tubing for measurement of blood pressure and connected to a low compliance pressure transducer (COBE Cardiovascular, Arvada, Colo.). The right femoral vein was cannulated for delivery of drugs. A high fidelity, 1.2-French SciSence pressure catheter (SciSence, London, ON, Canada) was inserted into the right carotid artery and advanced into the left ventricle to monitor cardiac performance. ECG leads were placed on the right and left arms, and left leg and connected to a BIOAmp (AD Instruments, Colorado Springs, Colo.). For carotid blood flow measurements, the left carotid artery was isolated and fitted with a 0.5-PSB perivascular flow probe connected to a TS420 flowmeter (Transonic Systems, Ithaca, N.Y.). Experimental solutions of 100 μg/μl probenecid were delivered as a bolus via the femoral vein catheter at 30 and 100 mg/kg with 5 minutes between each dose. Hemodynamic variables were collected and analyzed using a MacLab 4/S system (AD Instruments, Colorado Springs, Colo.) and Chart software.

Contractility studies with WT, TRPV2$^{+/-}$ and TRPV2$^{-/-}$ mice—Based on the results of the above experiments, it was determined that the dose of 100 mg/kg of probenecid gave a maximum contractility response. Mice were then injected the probenecid intraperitoneal (IP) to decrease the possible stress effects of surgery. WT, TRPV2$^{+/-}$, and TRPV2$^{-/-}$ mice were monitored by echo for 30 minutes after injection as described below.

Echocardiography—All echocardiographic studies were performed with a Vevo 2100 Ultrasound system (Visualsonics, Toronto Calif.) with an MS400 probe (30 MHz centerline frequency) and were post-processed at a separate workstation with Vevostrain software (Vevo 2100, v1.1.1 B1455, Visualsonic, Toronto, Canada). Images were obtained from PSLAX and short axis (SAX) views at depths between 2 and 10 mm in both M-mode and B-mode. All studies on mice exposed to I/R injury included M-mode, B-mode in PSLAX and strain imaging in SAX. While for the contractility studies, only M-mode measurements were obtained from the PSLAX. Strain imaging was performed from the B-mode images and regional radial strain and circumferential displacement were measured by regional wall and summed average from the SAX images. From the M-mode images, left ventricular cavity size and wall thickness was measured and the ejection fraction (EF) and fractional shortening (FS) calculations were obtained using the Vevo software.

The change in the EF, FS, as well as strain derived parameters was obtained by subtracting the baseline value from each individual subject against subsequent time-points. In addition, the average change from baseline for each time point between 5 and 30 minutes was determined for each mouse, with measurements being taken every 5 minutes. These averages were compared between the different groups.

In vivo electrophysiology—Electrocardiographic data was obtained during all echocardiographic studies. These studies were subsequently analyzed by an independent, blinded reader at all time points to evaluate for electrocardiographic changes and drug induced arrhythmias. The following parameters were measured: PR interval, RR interval, QRS width and were reported as peak change while the presence of supraventricular or ventricular arrhythmias was measured as a total observed over all images obtained in 30 minutes.

Ex vivo (Langendorff) studies—Isolated heart experiments were performed as previously described on WT mice. After hearts achieved steady-state with pacing at 400 bpm, probenecid ($10^{-6}$M) was perfused into the heart using a syringe pump and continuous perfusion for up to 5 minutes. Measurements were taken every second. After the 5 minute perfusion of probenecid, the hearts were removed from the cannula and flash frozen in $N_2$ for western blot analysis.

Molecular Studies

Quantitative RT-PCR—Hearts (LV) obtained for RNA isolation and qRT-PCR from WT, TRPV2$^{+/-}$ and TRPV2$^{-/-}$ mice were flash frozen and stored at –80° C. For assessment of TRPV2 transcript levels, total RNA was isolated (RNeasy kit; Qiagen, Valencia, Calif.) and cDNA synthesized (high capacity RNA-to-cDNA kit; Applied Biosystems, Carlsbad, Calif.) per manufacturer's instructions, using the C-terminal located primers 5'-CTACTGCTCAACATGCTC-3' (sense) (SEQ. ID. NO. 1) and 5'-CTCATCAGGTATACCATCC-3' (antisense) (SEQ. ID. NO. 2) which generate a 198 base pair product. All samples were performed in triplicate with a minimum of 3 independent experimental replicates with expression differences calculated using the delta-delta Ct approximation method with 18S mRNA as a loading control. Corrections for primer efficiency were made where appropriate using the Pfaffl Method.

Western Blot Analysis—WT hearts used for protein expression were isolated from control mice (C57, 12-16 weeks old) from the Langendorff experiments. Total protein for calcium handling proteins was isolated by homogenizing whole hearts in an ice-cold buffer containing (in mM): 80 Imidazole, 300 sucrose, 1 DTT, 10 sodium metabisulfite, the protease inhibitor cocktail P8340 (Sigma, St. Louis, Mo.) and the phosphatase inhibitor cocktail set II (EMD, Merck, Darmstadt, Germany). Protein concentrations were determined using the BCA Protein Assay kit (Pierce, Thermo Scientific, Rockford, Ill.).

Aliquots of protein were separated on SDS-PAGE gels (Novex gels, Invitrogen, Eugene, Oreg.) and then transferred to nitrocellulose membranes (Bio-Rad, Hercules, Calif.) and blocked with 5% BSA. The membranes were analyzed with primary antibodies. When appropriate, the membranes were cut in half to allow two different primary antibodies to be used. The top half would be used for one of the $Ca^{2+}$ handling proteins and the bottom half (less than 60 kD) would be used for the normalization protein, actin. In circumstances where it wasn't appropriate to cut the membrane, as the two proteins were too close in size, the membranes were stripped after the first protein. Membranes were also stripped between primary antibodies for phosphorylated proteins and corresponding total protein. Table A shows the amount of each protein loaded, size of the protein, dilution and the manufacturer.

Isolated Myocytes, Calcium Uptake and Handling

Isolation of ventricular myocytes—Hearts from WT mice (12-week old) were perfused on the Langendorff system with a modified Krebs-Henseleit buffer (KHB) composed of (mM) NaCl 118, KCl 5.4, HEPES 10, $NaH_2PO_4$ 0.33, $MgCl_2$ 2, glucose 10, taurine 30, butanedione monoxime 10 (pH=7.4). Then an enzyme solution (KHB containing 0.7 mg/ml type II collagenase, 0.1% BSA and 25 µM $CaCl_2$) was used to digest the hearts for 10 min. Finally, ventricles of the hearts were excised, minced and filtered to obtain isolated cells. After sufficient sedimentation, the supernatant was removed and the cells were resuspended.

Myocyte contractility measurement—Myocytes were put on a plexiglass chamber containing a Tyrode's solution composed of (mM) NaCl 140, KCl, 5.4, $MgCl_2$ 1, $CaCl_2$ 1.8, HEPES 5, glucose 10 (pH=7.4). Myocytes were excited under 0.5 Hz field stimulation. After reaching the steady state, myocyte shortening and the rates of shortening (+dL/dt) and relengthening (−dL/dt) were imaged with a CCD camera and monitored by a video-edge detector. Drugs were dissolved in Tyrode's solution and perfused into the chamber. Data were continuously collected through the PCLAMP 9 software.

Myocyte $Ca^{2+}$ transient and cytosolic $Ca^{2+}$ measurement—Myocytes were loaded with Fluo-4 acetoxymethyl ester (7 µM) for 20 min at room temperature, followed by a 10 min wash with Tyrode's solution, and then placed onto a plexiglass chamber for recording. For $Ca^{2+}$ transient measurements, myocytes were excited under 0.5 Hz and 3 Hz field stimulation, and the fluorescence signals were obtained using a Nikon TE 2000 microscope and collected through an InCyt Standard photometry system. For cytosolic $Ca^{2+}$ analysis in quiescent myocytes, a Zeiss LSM 510 confocal microscope was used to record fluorescent images from resting myocytes. Line-scan mode was applied at 3.07 ms intervals with 512 pixels spaced at 0.056 µm. Drugs were dissolved in Tyrode's solution and perfused into the chamber. Images of myocytes were recorded every 30 s after drug application. Data analysis was performed using Clampfit 9.2 and Image J 1.44 software.

Water soluble probenecid was used for all of the myocyte experiments.

Electrophysiological recordings—Isolated myocytes were perfused with a $Na^+$- and $K^+$-free solution containing (mM): tetraethylammonium chloride (TEA-Cl) 137, CsCl 5.4, $CaCl_2$ 2, $MgCl_2$ 1, HEPES 5, glucose 10 and 4-aminopyridine 3 (pH=7.4). Whole-cell patch clamp recordings were performed with an Axopatch-1B amplifier. For $Ca^{2+}$ current recordings, glass pipettes were filled with solution containing (mM): aspartic acid 115, CsOH 115, CsCl 20, EGTA 11, HEPES 10, $MgCl_2$ 2.5, Na-GTP 0.1, Mg-ATP 2 (pH adjusted to 7.2 with CsOH). Probenecid was dissolved in a $Na^+$- and $K^+$-free solution which was used to perfuse the myocytes. Data were collected using pCLAMP9 software through an Axon Digidata 1322A data acquisition system. All experiments were performed at room temperature (24° C.).

Statistical Analysis—All data are expressed as means±standard error of the mean (SEM). Results were analyzed with a paired and unpaired Student's t-test and one-way ANOVA as needed. P values ≤0.05 were considered significant. Power analysis was employed to determine the group size necessary to determine whether significant differences exist between endpoint measures in control and experimental groups as previously described. SigmaPlot was used to produce a best fit line and calculate an $EC_{50}$ for the dose response curves.

Results

Figure 1B:
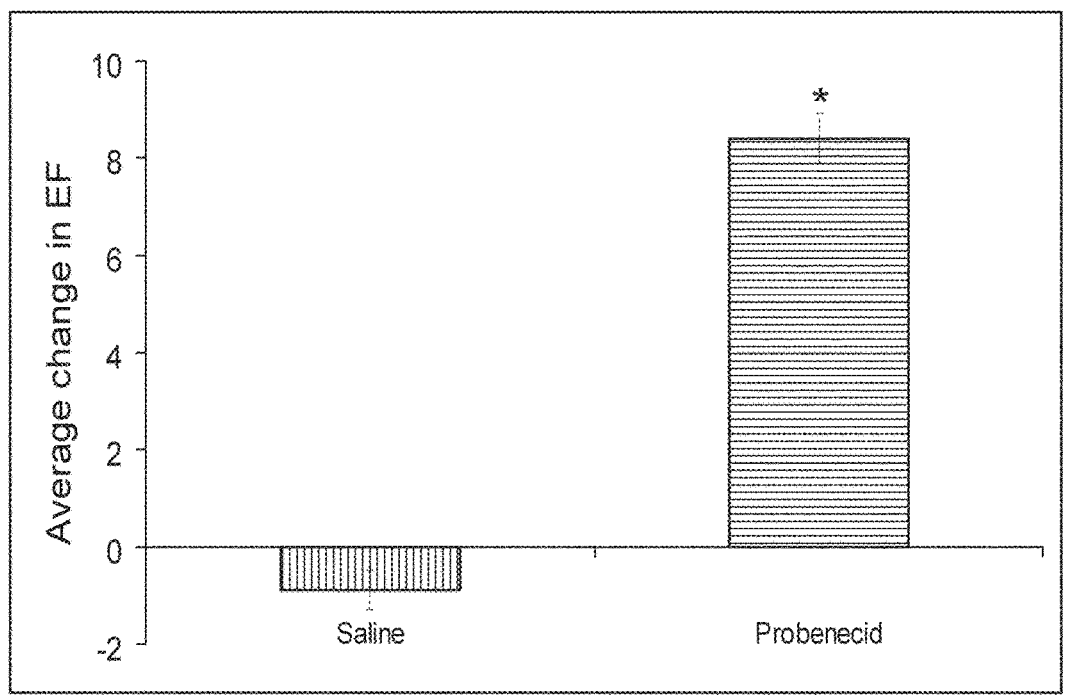
FIG. 1B is a bar graph illustrating that probenecid did not result in any echocardiographic changes.
Figure 1C:
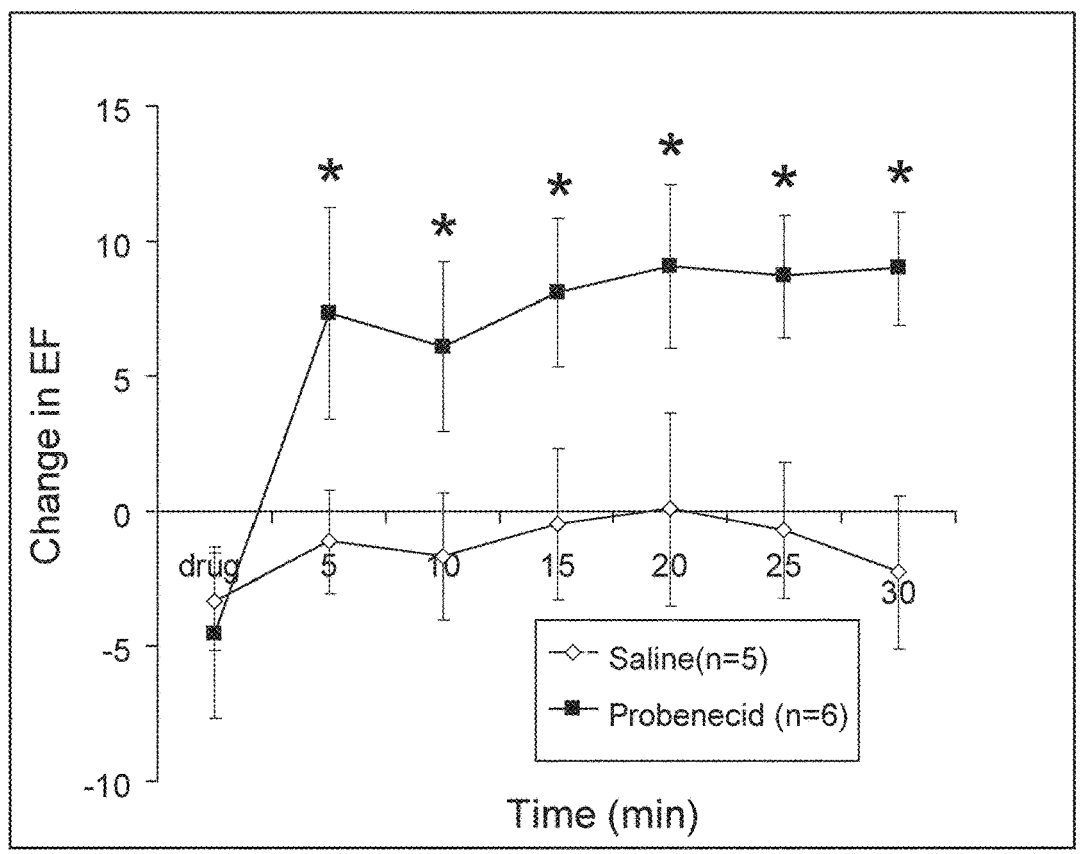
FIG. 1C is a curve illustrating a time course of the change in EF following IV administration of 200 mg/kg probenecid, in accordance with embodiments of the invention.
Figure 1D:
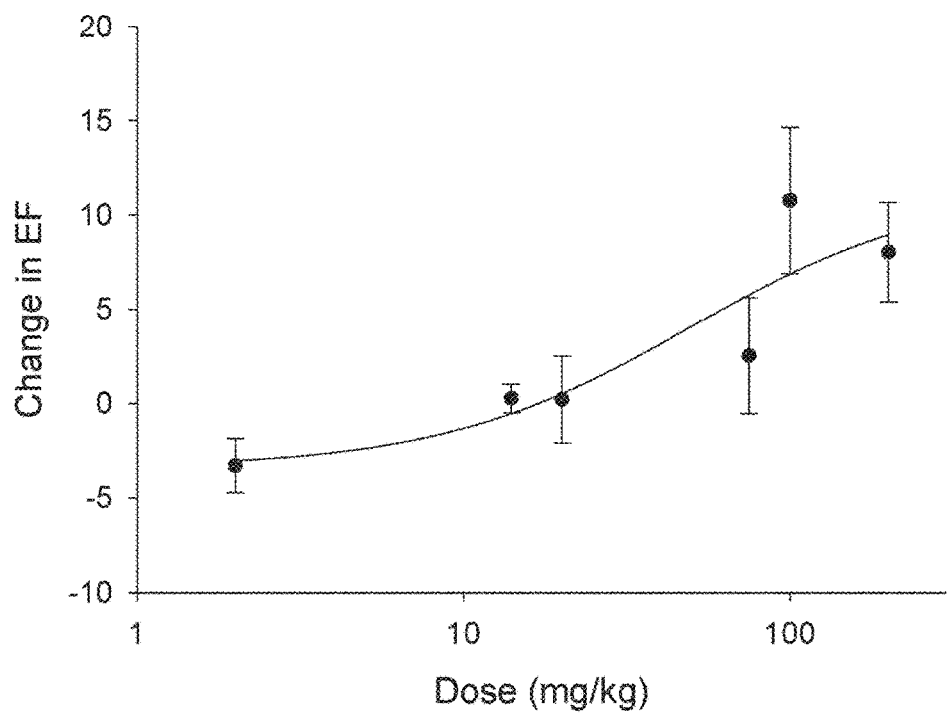
FIG. 1D is a curve illustrating the dose-dependent changes in EF after injection of various different concentrations of probenecid, in accordance with embodiments of the invention.

Probenecid increases in vivo contractility in WT but not $TRPV2^{-/-}$ mice.—Administration of probenecid to WT mice resulted in increased contractility as measured via EF relative to EF in control mice given saline (FIG. 1A). The increased contractility was noted within 5 minutes of the bolus injection with all doses at or above 75 mg/kg (peak change of 5.26±3.35, 8.40±2.80, 7.32±2.52 for 75 mg/kg, 100 mg/kg and 200 mg/kg, respectively) (FIGS. 1B and 1C, data not shown for 75 and 100 mg/kg). The measured change in contractility as measured at 5 minute intervals (for 30 minutes total) revealed a dose dependent increase in contractility with an estimated $EC_{50}$ of 49.33 mg/kg (FIG. 1D). The EF remained at an elevated state for at least 1 hour on subjects (n=5, dose of 200 mg/kg IV) that were evaluated for a longer period of time (average increase in EF over baseline of 8.9±2.57, data not shown).

Figure 1E:
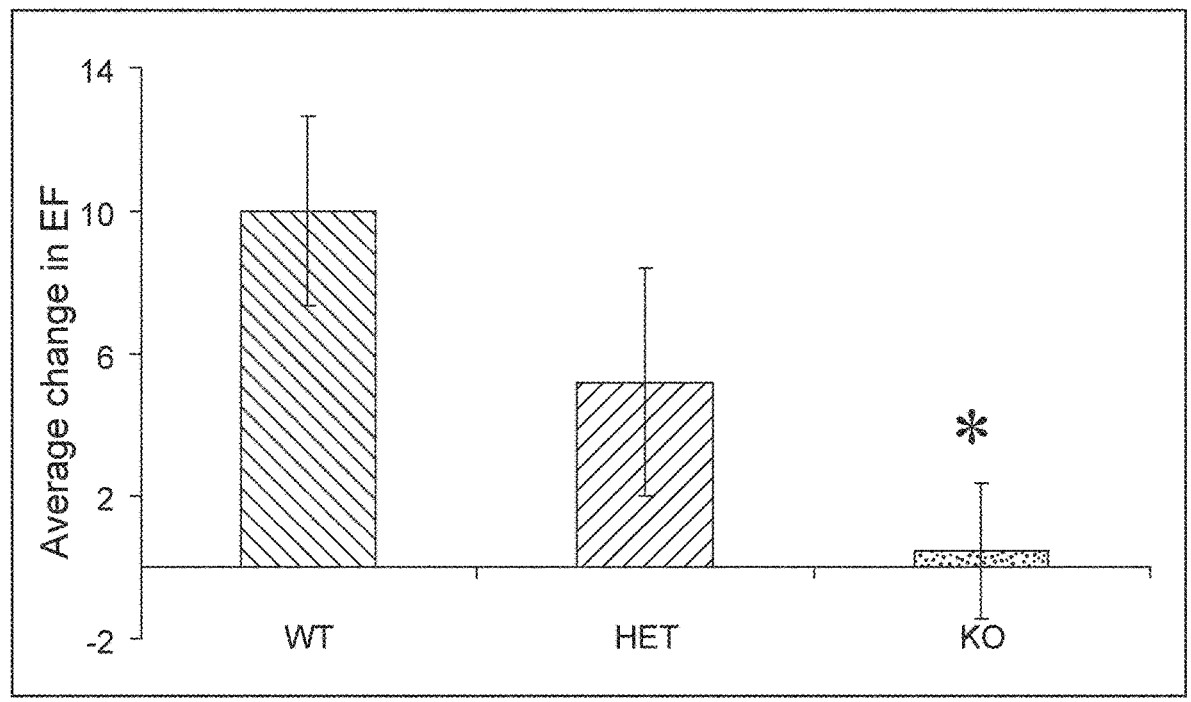
FIG. 1E is a bar graph illustrating the average change in EF following IP administration of 100 mg/kg probenecid for wild type (WT), TRPV2$^{+/-}$ (HET) and TRPV2$^{-/-}$ (KO).

Probenecid administered to the $TRPV2^{+/-}$ mice increased contractility, though the peak change in contractility was only 49% of that observed with the same dose in the WT mice (FIG. 1E). Furthermore, when probenecid was administered to the $TRPV2^{-/-}$, there was no discernable cardiac response noted during the 30 minutes of echocardiogram measurements.

Figure 2A:
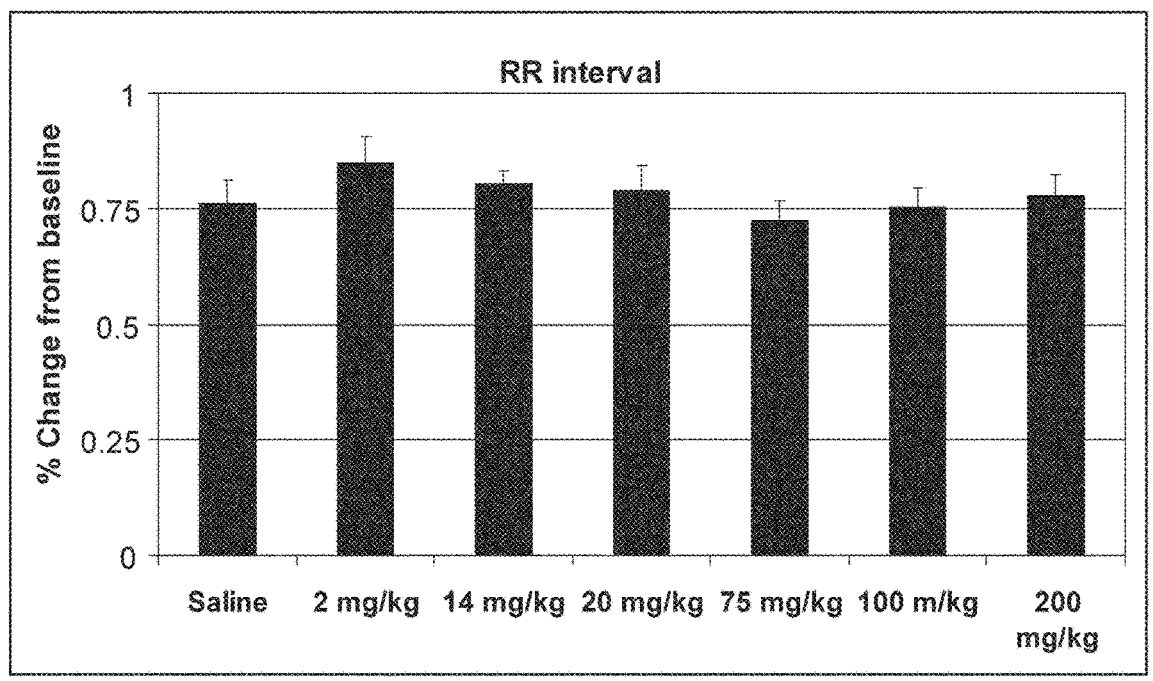
FIG. 2A is a bar graph illustrating the RR interval measured after various doses of probenecid were administered, in accordance with embodiments of the invention.
Figure 2B:
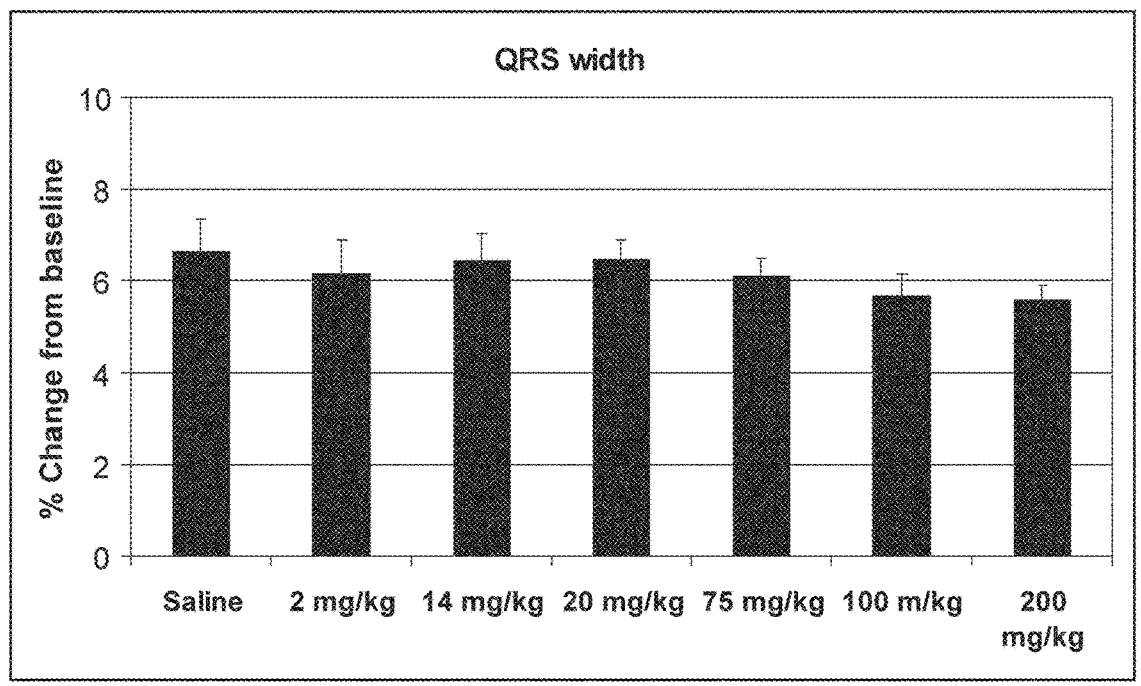
FIG. 2B is a bar graph illustrating the PR interval measured after various doses of probenecid were administered, in accordance with embodiments of the invention.
Figure 2C:
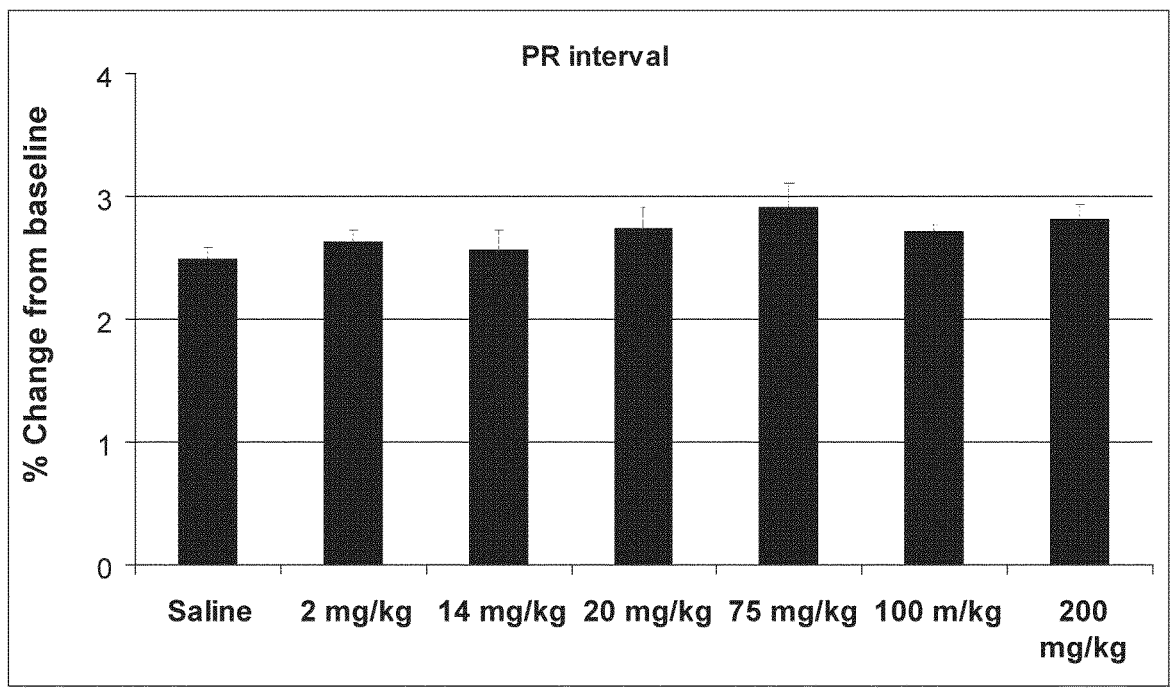
FIG. 2C is a bar graph illustrating the QRS interval measured after various doses of probenecid were administered, in accordance with embodiments of the invention.
Figure 2D:
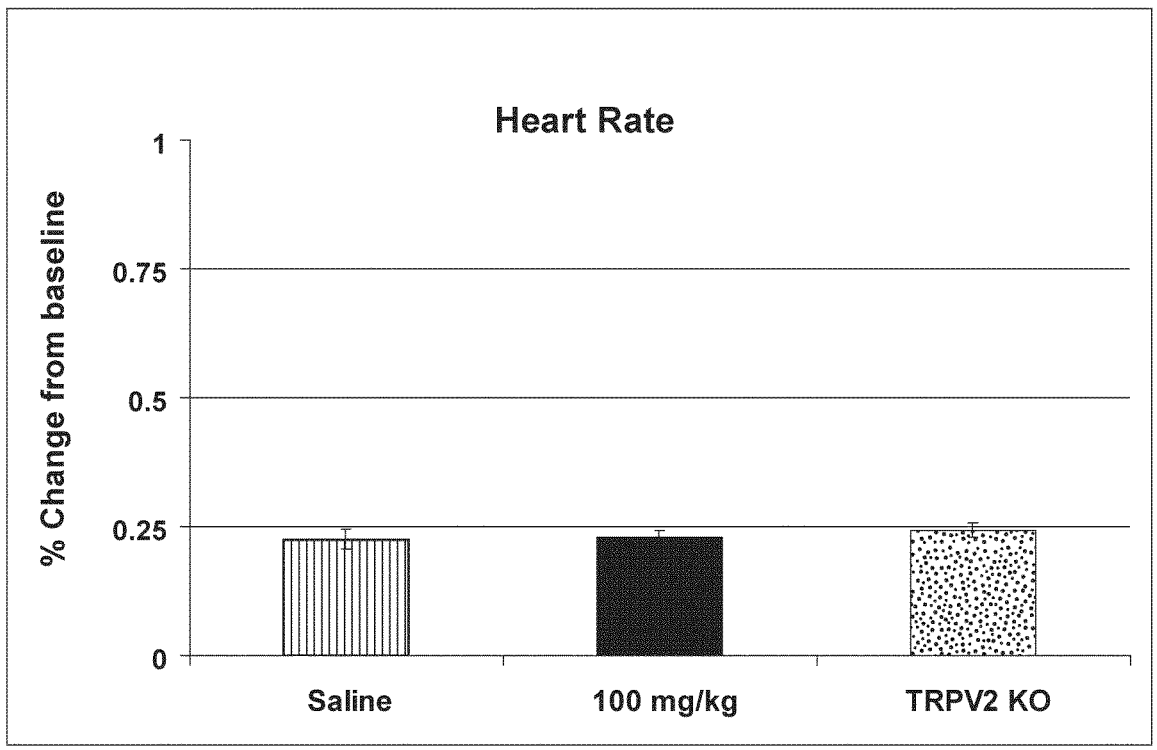
FIG. 2D is a bar graph illustrating the heart rate measured after various doses of probenecid were administered, in accordance with embodiments of the invention.

Probenecid does not cause any measurable changes in electrical conduction in vivo mice.—It is known that commonly used inotropes result in varied arrhythmias. No supraventricular or ventricular arrhythmias or premature atrial or ventricular beats were observed after any dose of probenecid administered in WT mice. Furthermore, at all doses there were no measured changes in any conduction intervals (FIGS. 2A, B and C), and there were no significant differences noted between probenecid (100 mg/kg) IP in WT and $TRPV2^{-/-}$ mice (FIG. 2D).

Figure 3A:
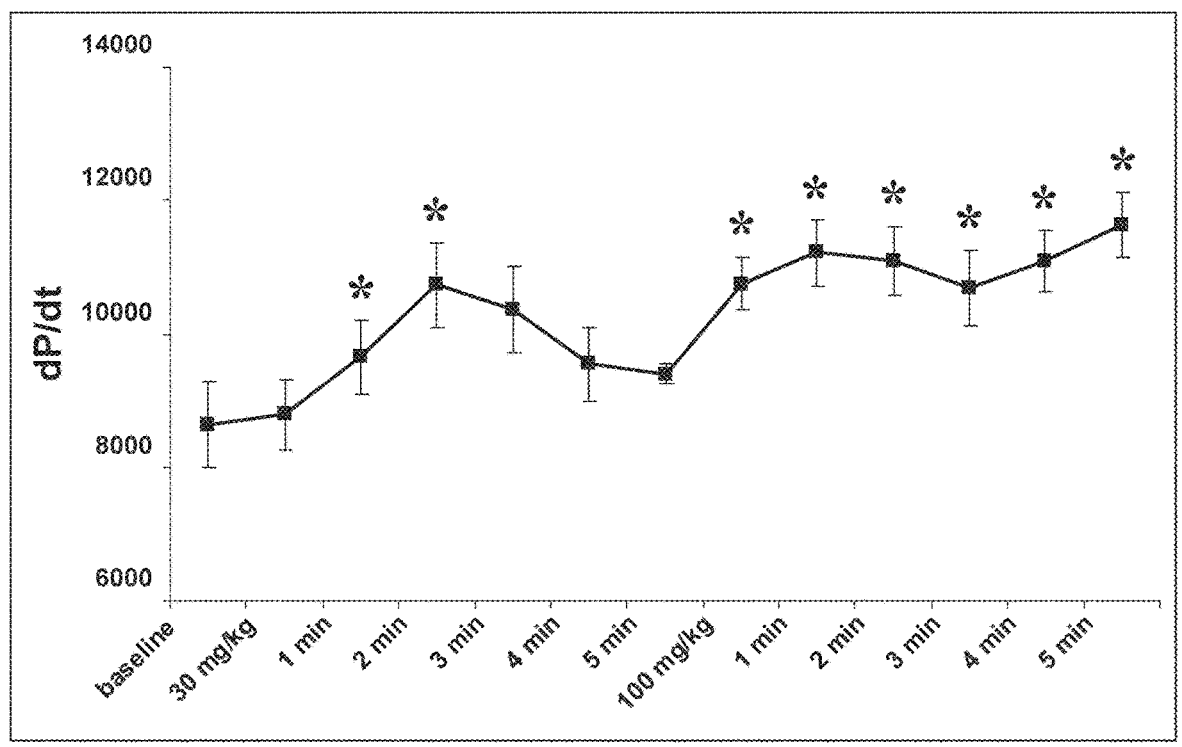
FIG. 3A is a curve illustrating the in vivo measurement of +dP/dt after administration of 30 mg/kg and 5 minutes following 100 mg/kg of probenecid IV, in accordance with embodiments of the invention.
Figure 3B:
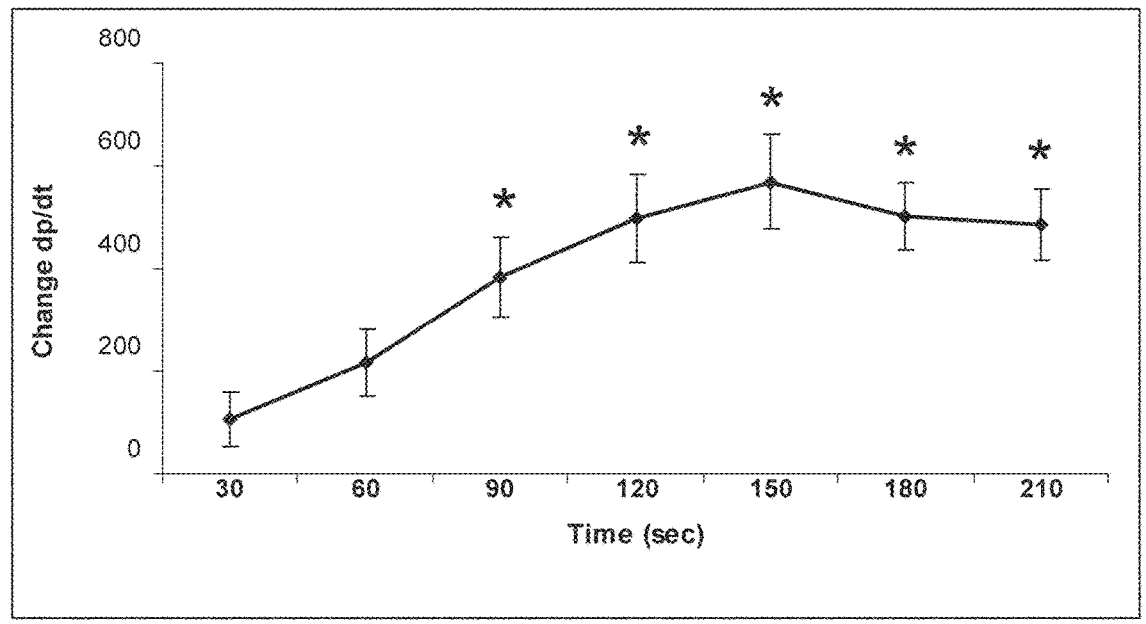
FIG. 3B is a curve illustrating the Langendorff perfused measurements of the change in +dP/dt during perfusion of $10^{-6}$ probenecid, 90-210 sec are all significantly different from baseline, in accordance with embodiments of the invention.

Probenecid increases contractility in in vivo hearts and in Langendorff perfused hearts.—Invasive measurements of +dP/dt demonstrated an effect similar to the Langendorff perfused hearts which were used to measure the cardiac specific effects of probenecid ($10^{-6}$ M) on contractility. We found that administration of probenecid in vivo at both a low (30 mg/kg) and high (100 mg/kg) dose rapidly increased the peak +dP/dt (FIG. 3A). The changes in average +dP/dt over time in Langendorff perfused hearts are shown in FIG. 3B. This change was found to be statistically significant from 90 to 210 seconds and reached a steady state between 120 and 180 seconds (FIG. 3B). Relaxation (−dP/dt) was also affected at the same concentration of probenecid, increasing from 1812±158 to 2309±133 (P<0.01). After treatment with probenecid, the hearts were flash frozen to be used for other experiments.

Figure 4:
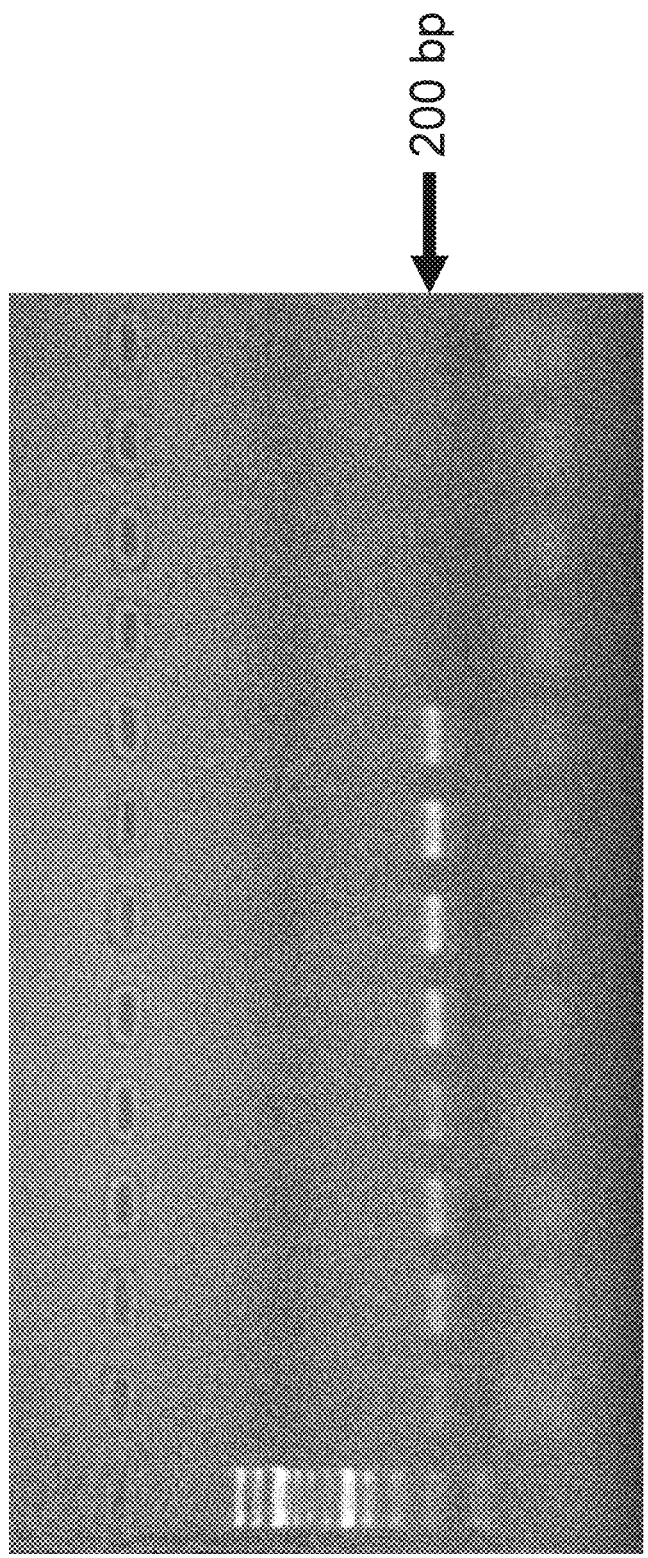
FIG. 4 is quantitative RT-PCR product from mRNA isolated from wild type (WT), TRPV2$^{+/-}$ (HET) and TRPV2$^{-/-}$ (KO) mouse hearts.

TRPV2 mRNA is found in cardiac tissue.—Quantitative real time PCR from WT, TRPV2$^{+/-}$ and TRPV2$^{-/-}$ mice revealed a decrease in expression from WT to TRPV2$^{+/-}$ mice, with no count detected for the TRPV2$^{-/-}$ mice. PCR products from the qRT-PCR were run on a 2% agarose gel to verify specificity and again found expression at approximately 200 bp with no expression in the TRPV2$^{-/-}$ and decreased in the TRPV2$^{+/-}$ (FIG. 4).

Figure 5A:
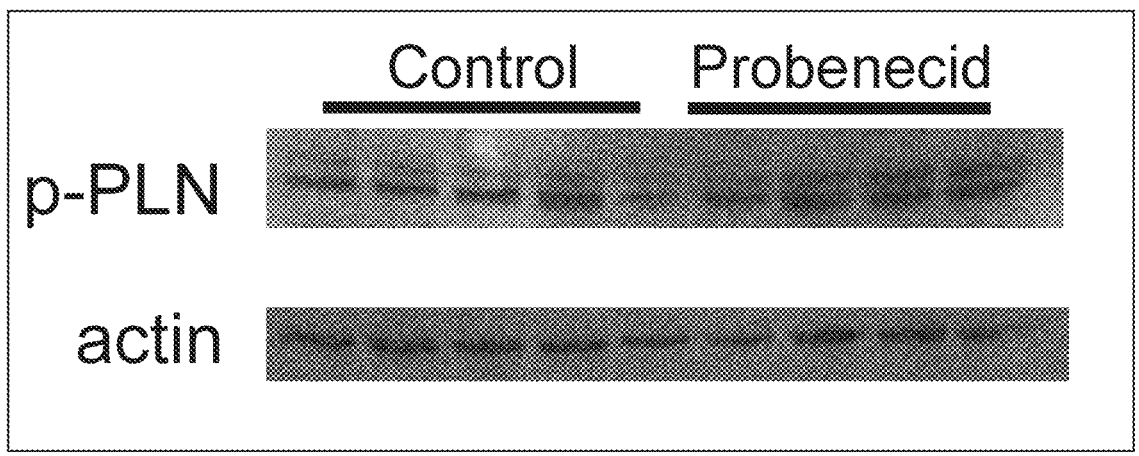
FIG. 5A is a representative Western blot analysis of phosphorylated Phospholamban (p-PLN) comparing saline to probenecid.
Figure 5B:
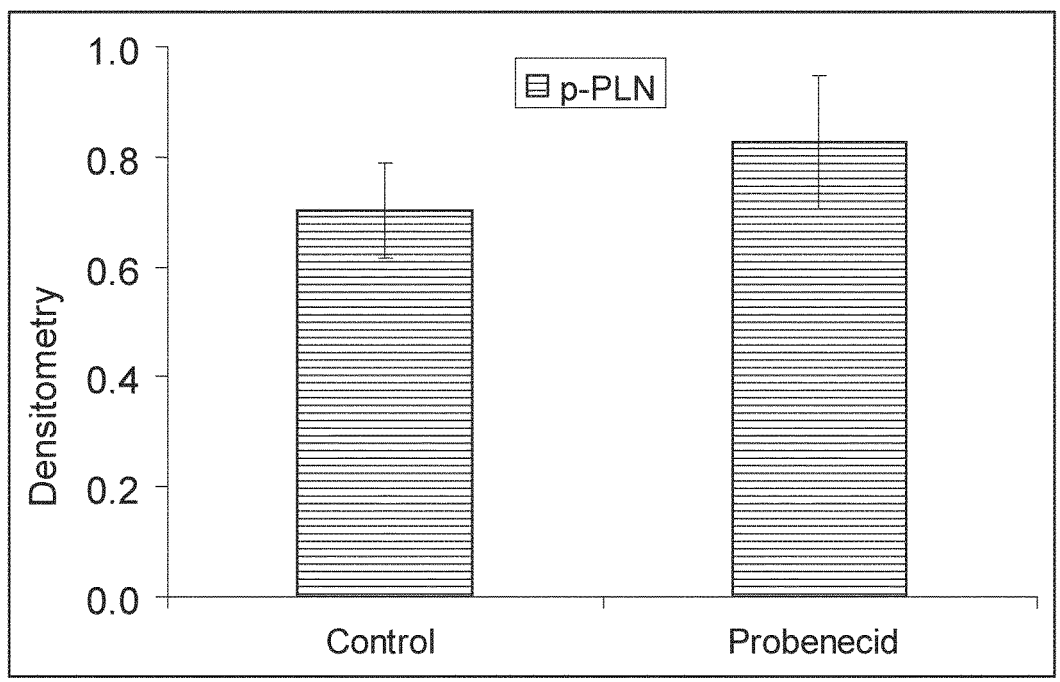
FIG. 5B is a bar graph quantifying the Western blot analysis of phosphorylated Phospholamban (p-PLN) comparing saline to probenecid.
Figure 5C:
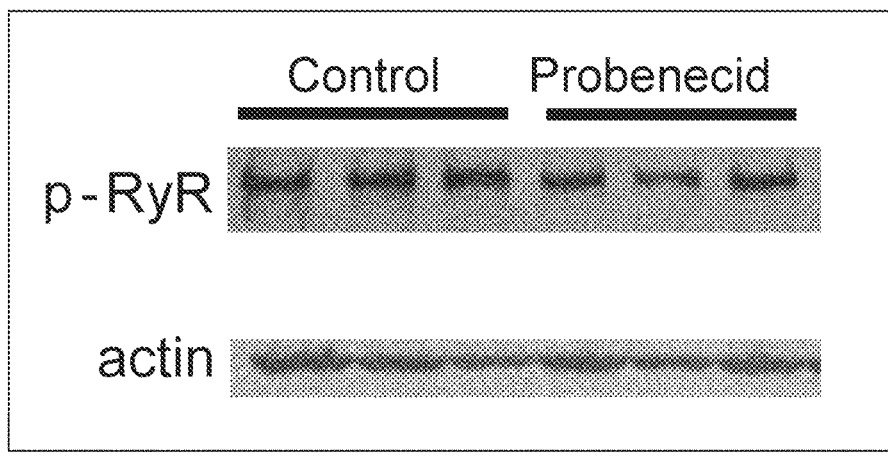
FIG. 5C is a representative Western blot analysis of phosphorylated Ryanodine receptor 2 (p-RyR2) comparing saline to probenecid.
Figure 5D:
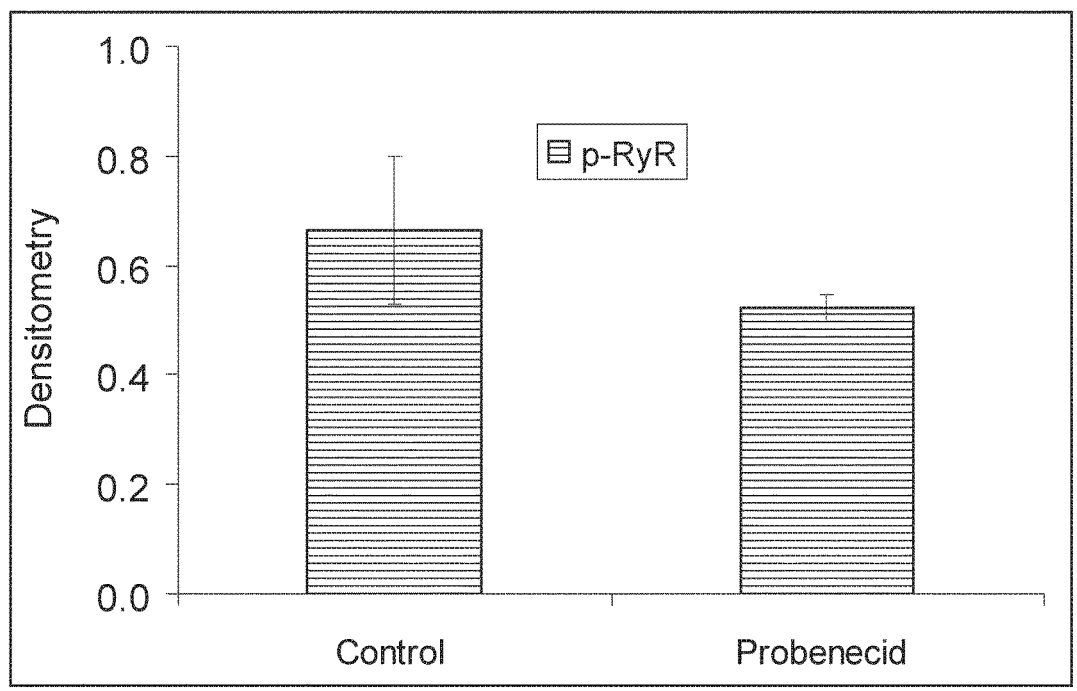
FIG. 5D is a bar graph quantifying the Western blot analysis of phosphorylated Ryanodine receptor 2 (p-RyR2) comparing saline to probenecid.

Expression levels of calcium handling proteins are unchanged after probenecid administration.—Using the hearts isolated from the Langendorff procedure animals and age-matched control mouse hearts perfused with Tyrode's solution, the expression of phospholamban (PLN) and the ryanodine receptor (RyR), phosphorylated and total protein, in the whole heart was assessed. Even though these hearts demonstrated an increase in contractility, no significant changes in the amount of phosphorylated or total phospholamban or ryanodine receptor in these hearts (FIGS. 5A and 5B) nor in the ratio of p-PLN to t-PLN were found (FIG. 5C). Furthermore, the sodium/calcium exchanger (NCX) and SERCA2a was investigated to determine if there was another Ca$^{2+}$-handling protein responsible for the increase in contractility, but found no changes were found in the expression levels (data not shown).

There is a dose-dependent increase of contractility by probenecid in isolated myocytes.—Probenecid was found to have increased the contractility of isolated ventricular myocytes in a dose-dependent manner (FIG. 6). Fractional shortening (FS) of myocytes was increased by 30.8±1.4% (from 6.9% to 9.0%; n=6, P<0.01) when exposed to 0.1 µM probenecid at 0.5 Hz and room temp, and increased from 10.1% to 13.9% (n=4; P<0.01) at 3 Hz and 32° C.; the dose-response curve for the action of probenecid had an EC$_{50}$ of 1.6 nM (FIGS. 6A and 6B). Pretreatment of myocytes with ruthenium red, a non-selective blocker of TRPV2 channels, completely abolished probenecid's effect on myocyte contractility (FIGS. 6C and 6D). In isolated myocytes, we measured the +dL/dt and −dL/dt. At room temperature, probenecid administration resulted in a change in maximum +dL/dt from 80.6±12.3 to 112.5±16.6 (n=10, P<0.01) while the −dL/dt increased from 57.7±7.4 to 77.6±8.7 µm/sec (P<0.01).

Figure 6A:
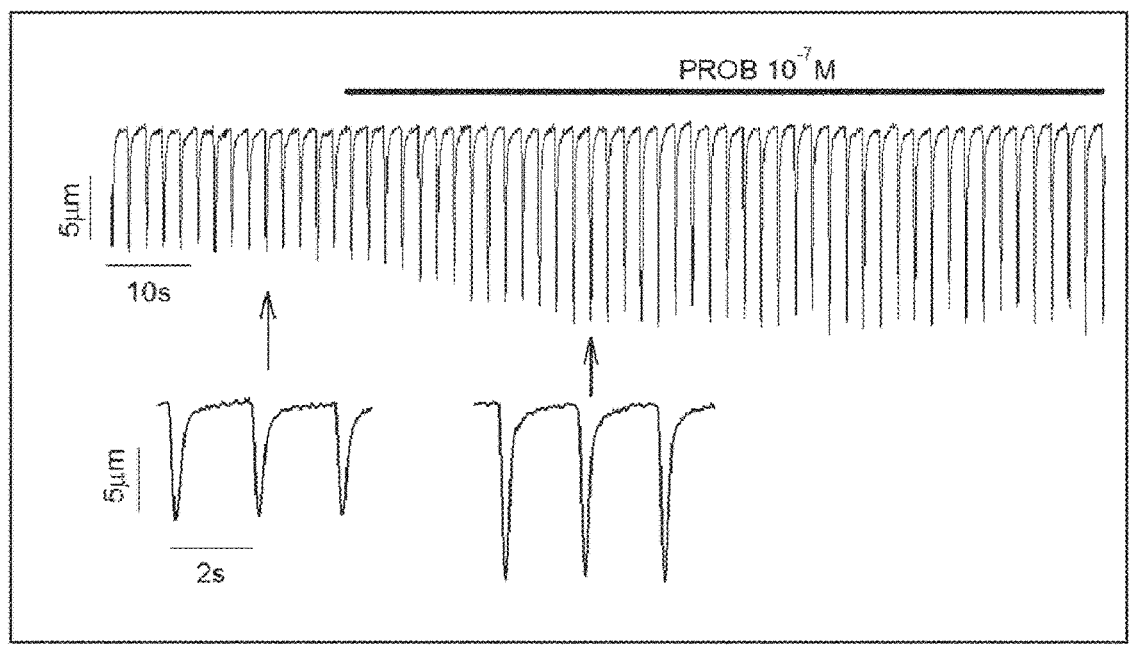
FIG. 6A is a representative contraction trace of ventricular myocytes upon exposure to $10^{-7}$ M probenecid (PROB).
Figure 6B:
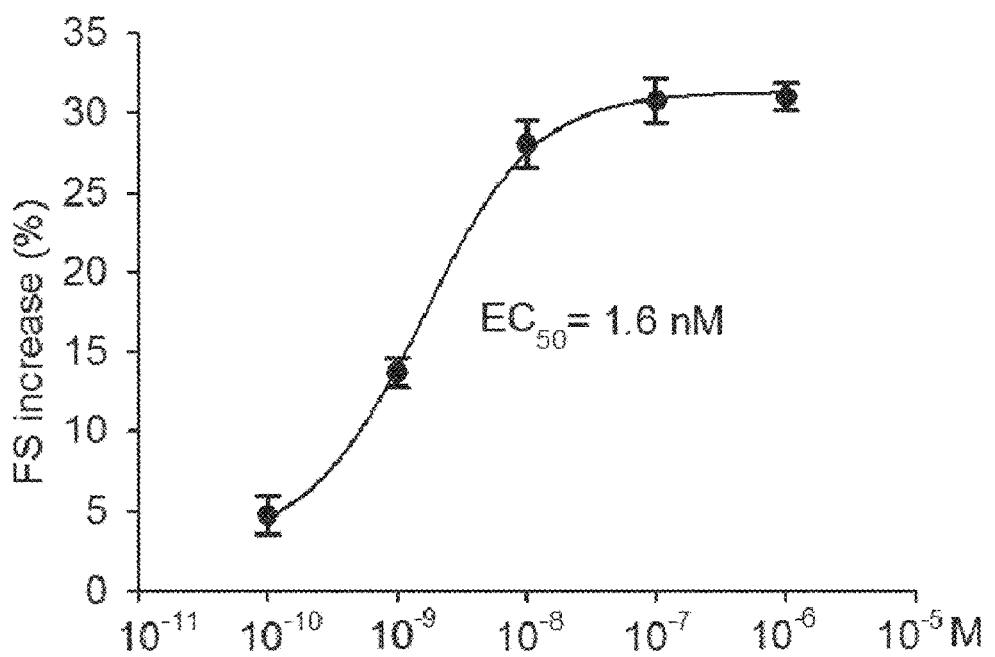
FIG. 6B is a Dose-response curve of probenecid on myocyte contractility. Data points are averages from 4 mice and fitted to sigmoidal non-linear regression curve.
Figure 6C:
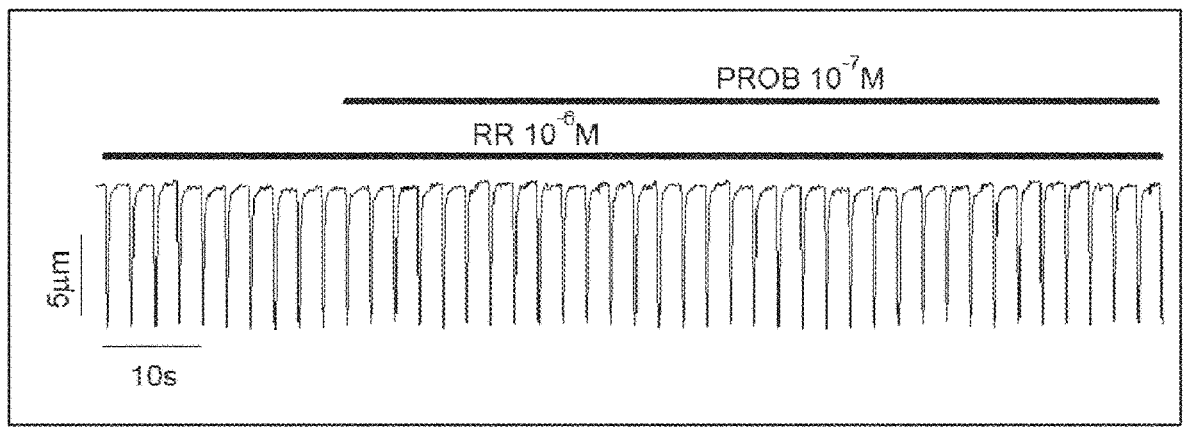
FIG. 6C is a representative contraction trace with ventricular myocytes upon exposure to $10^{-7}$ M probenecid (PROB) with ruthedium red pretreatment.
Figure 6D:
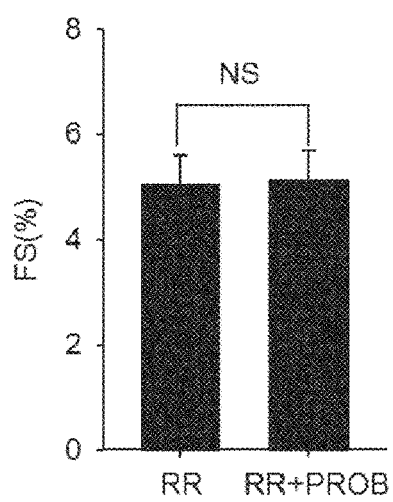
FIG. 6D is a bar graph illustrating the average data on myocyte fractional shortening (FS) under control and $10^{-7}$ M probenecid exposure.
Figure 6E:
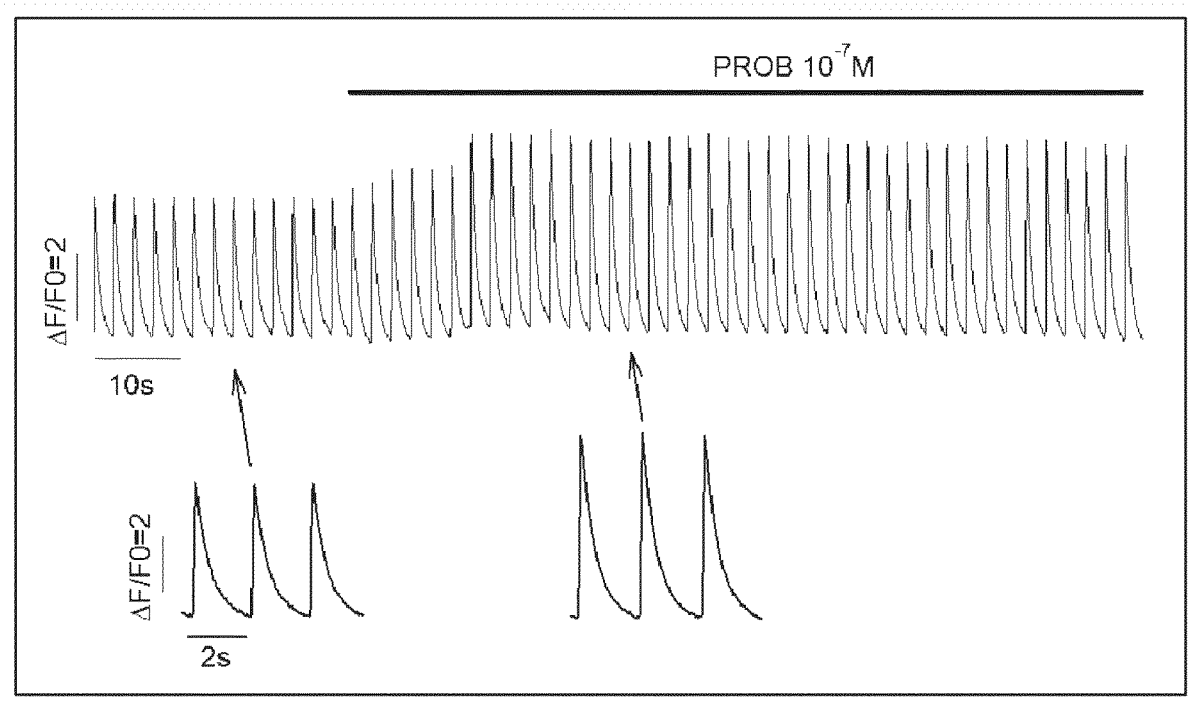
FIG. 6E is a representative Ca$^{2+}$ transient trace of ventricular myocytes upon exposure to $10^{-7}$ M probenecid (PROB).
Figure 6F:
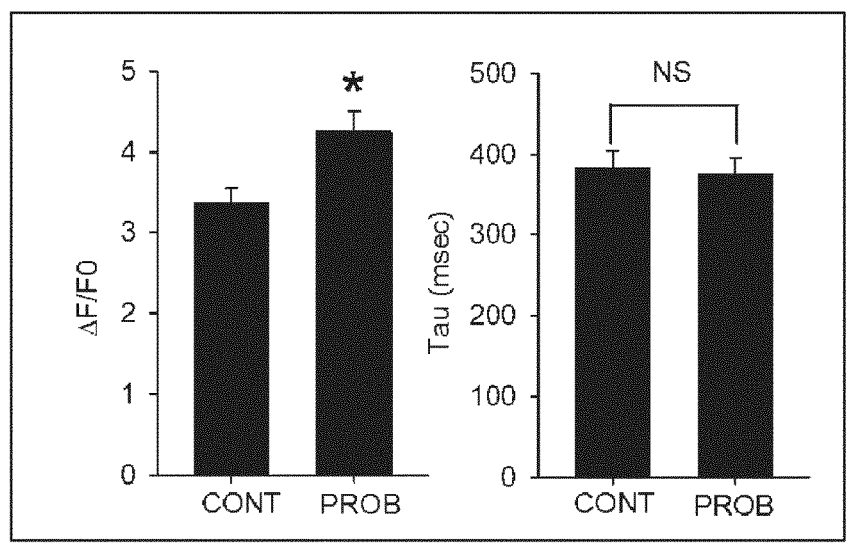
FIG. 6F is a bar graph illustrating average data on Ca$^{2+}$ transient amplitude F/F0 (left) and time constant tau (right) under control and $10^{-7}$ M probenecid exposure.

The effect of probenecid on the myocyte Ca$^{2+}$ transient was also examined. Probenecid caused a significant increase in Ca$^{2+}$ transient amplitude (ΔF/F0) (FIGS. 6E and 6F), which was consistent with the fractional shortening increase found in myocytes. The concentration of 0.1 µM probenecid increased the Ca$^{2+}$ transient amplitude (ΔF/F0) from 3.35±0.20 to 4.25±0.25 (P<0.001), while the decay rate (Tau) of Ca$^{2+}$ transient was not affected by probenecid treatment (FIG. 6F).

Figure 7A:
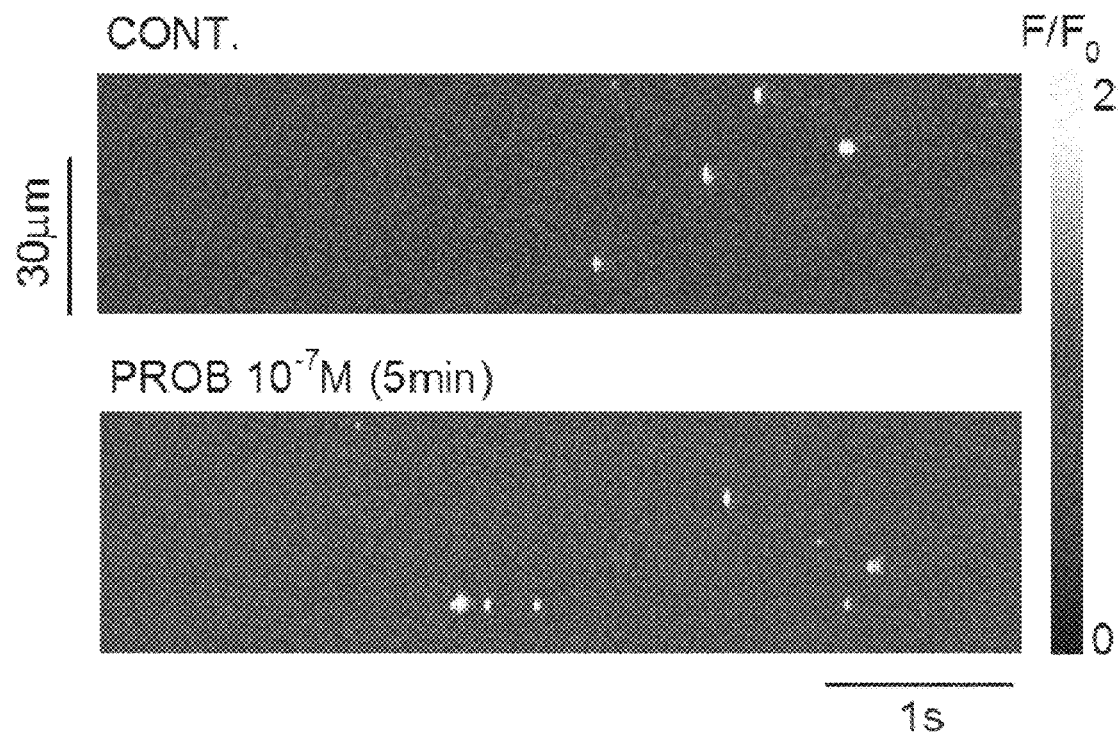
FIG. 7A are images of a confocal microscopic line-scan of cytosolic Ca$^{2+}$ from a myocyte under control and upon exposure to $10^{-7}$ M probenecid for 5 minutes with a a heat map shown to indicate the F/F0 intensity (valued from 0 to 2).
Figure 7B:
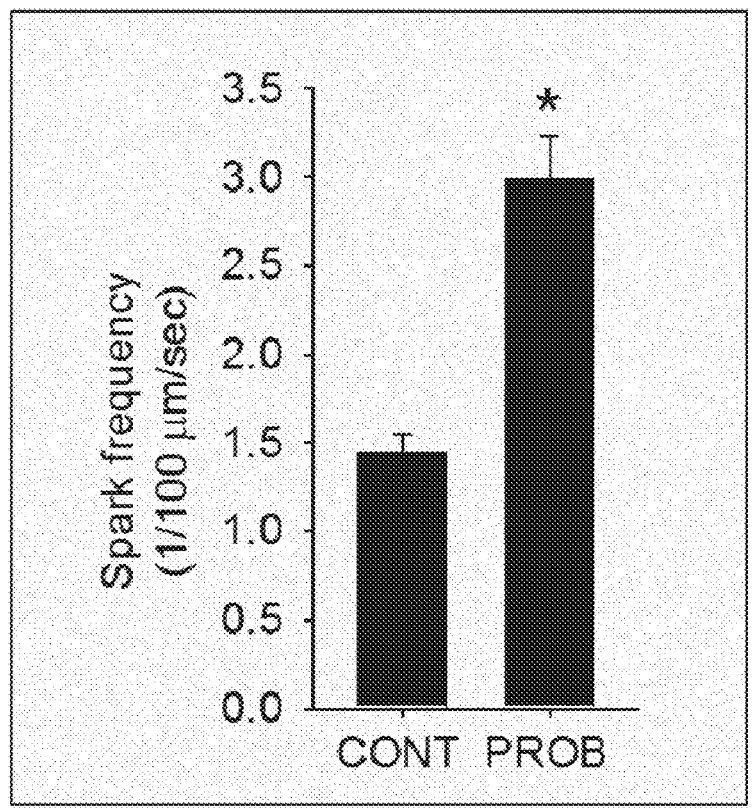
FIG. 7B is a bar graph illustrating average data on Ca$^{2+}$ spark frequency under control and upon exposure to $10^{-7}$ M probenecid for 5 minutes.
Figure 7C:
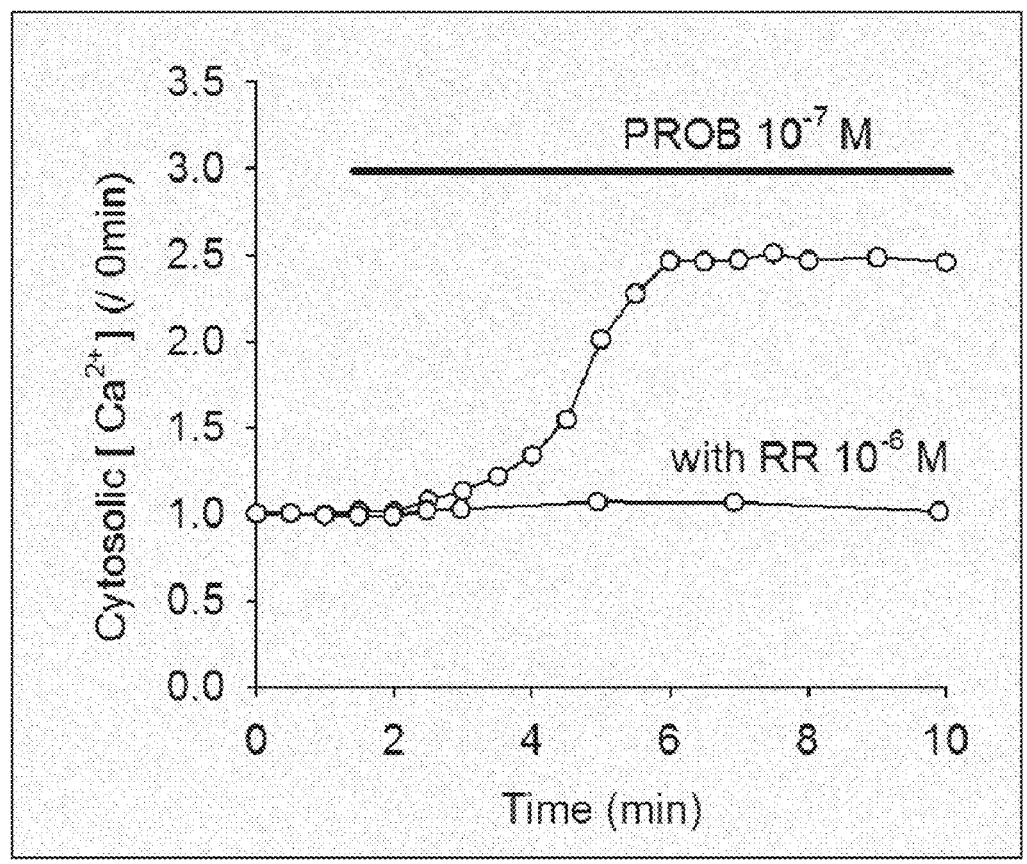
FIG. 7C is a curve illustrating time courses of cytosolic Ca$^{2+}$ in myocytes with and without $10^{-6}$ M ruthenium red (RR) pretreatment upon exposure to $10^{-7}$ M probenecid.
Figure 7D:
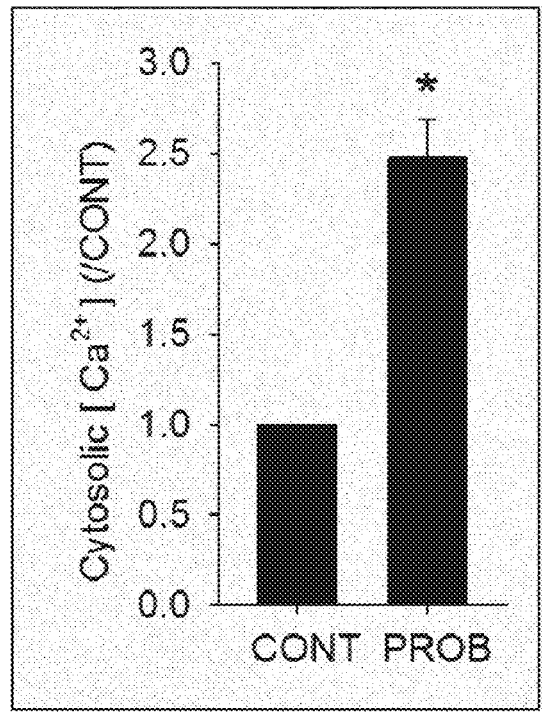
FIG. 7D is a bar graph illustrating average data on myocyte cytosolic Ca$^{2+}$ under control and $10^{-7}$ M probenecid exposure (for 5 minutes).
Figure 7E:
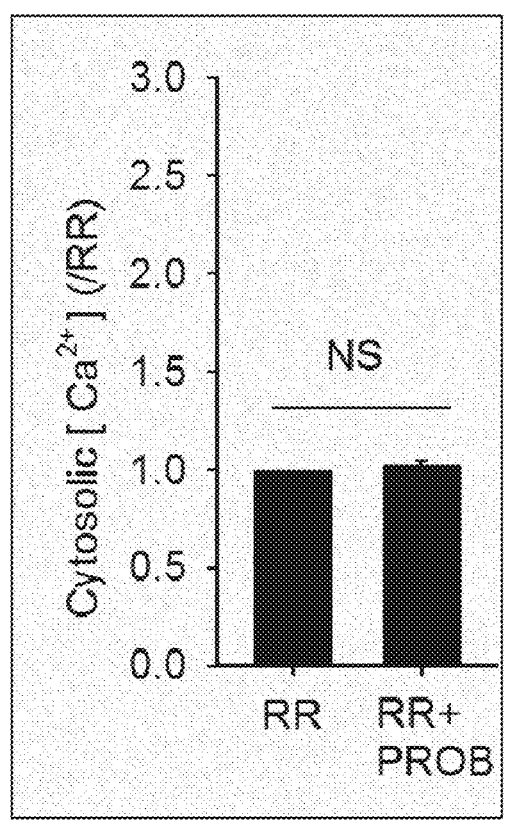
FIG. 7E is a bar graph illustrating average data on myocyte cytosolic Ca$^{2+}$ pretreated with $10^{-6}$ M ruthenium red under control and $10^{-7}$ M probenecid exposure (for 5 minutes).
Figure 7F:
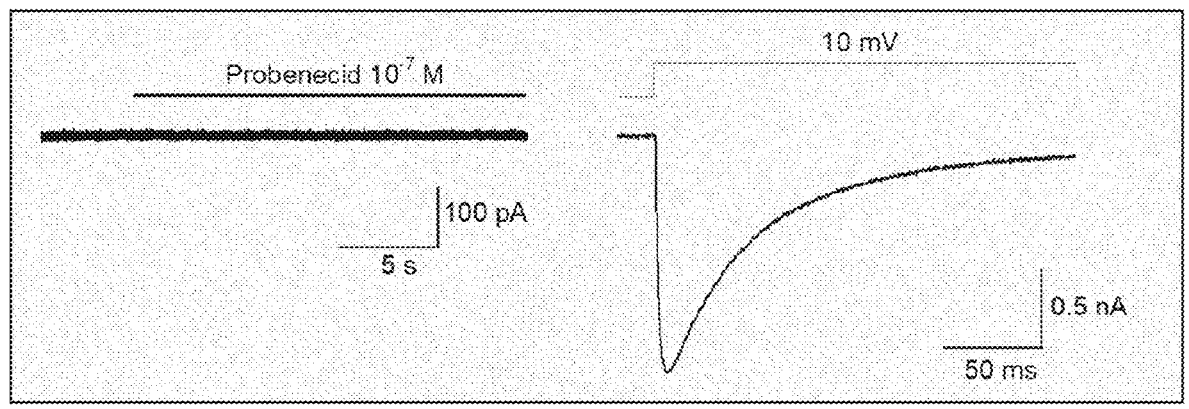
FIG. 7F are patch clamp data from the same myocyte showing no inward Ca$^{2+}$ current with $10^{-7}$ M probenecid treatment (left) and L-type Ca$^{2+}$ current elicited by depolarization voltage step to +10 mV.
Figure 7G:
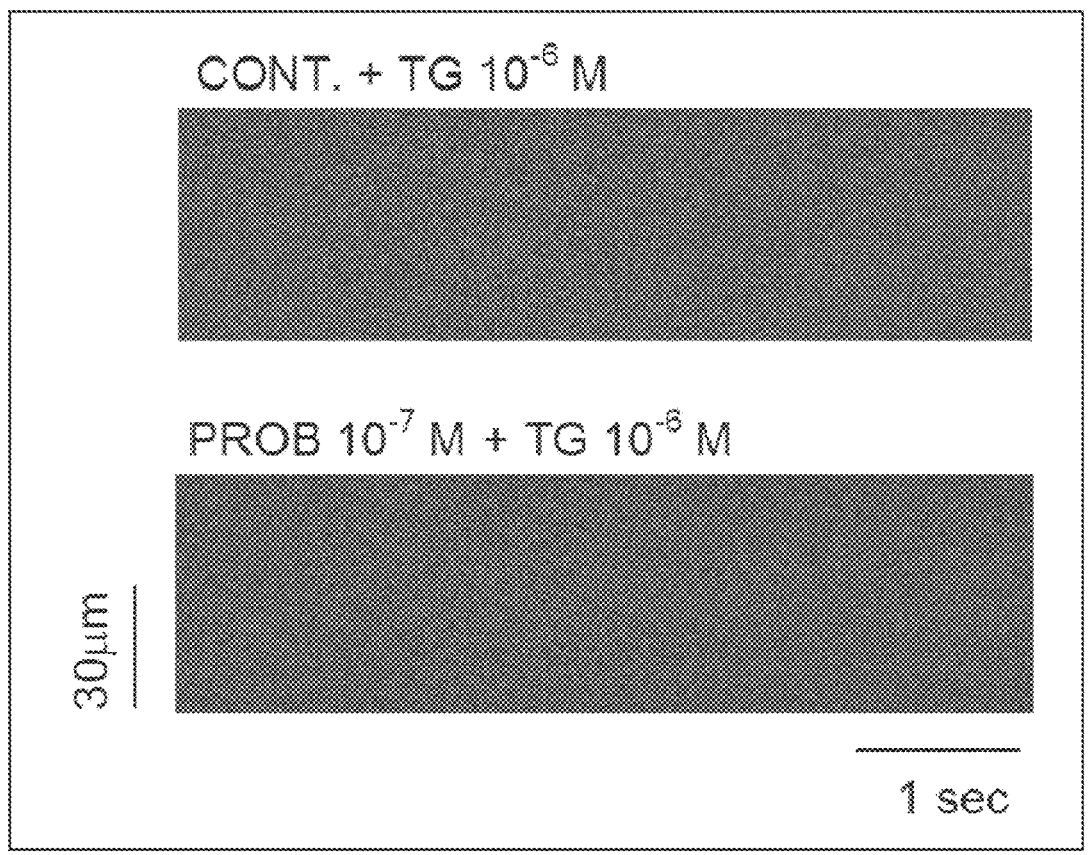
FIG. 7G are images of confocal microscopic line-scan of cytosolic $Ca^{2+}$ from a myocyte pretreated for 15 minutes with $10^{-6}$ M thapsigargin (TG), before and after treatment with $10^{-7}$ M probenecid for 5 minutes.
Figure 7H:
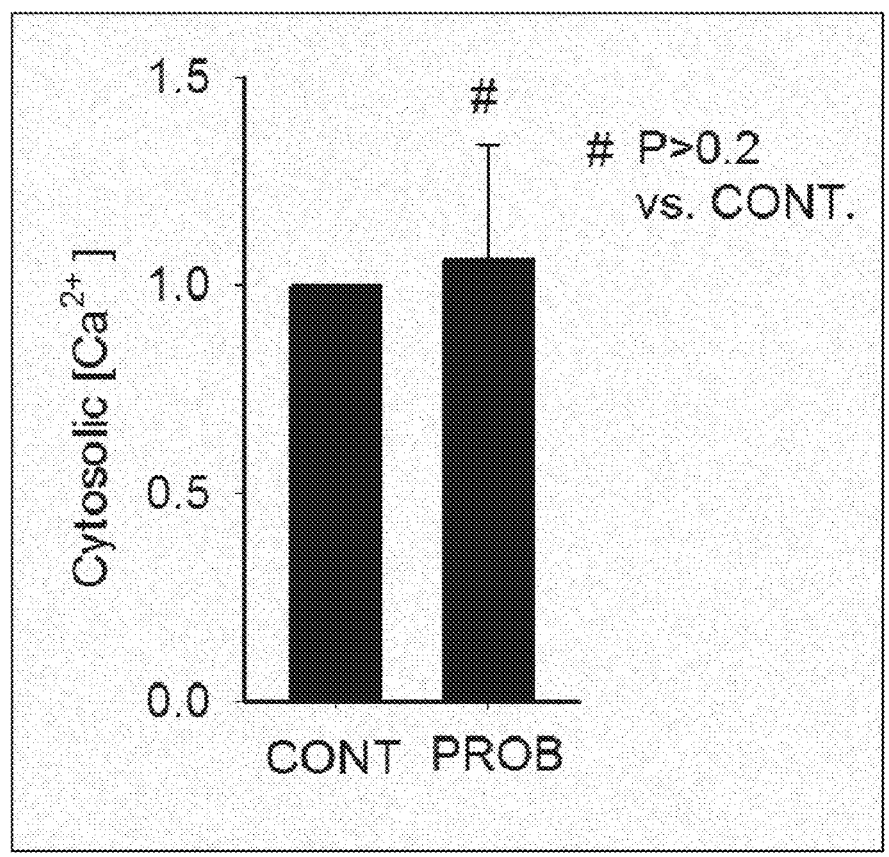
FIG. 7H is a bar graph illustrating average data on myocyte cytosolic $Ca^{2+}$ under control and after $10^{-7}$ M probenecid treatment, in myocytes pretreated with $10^{-6}$ M thapsigargin.

Cytosolic Ca$^{2+}$ increase by probenecid in isolated myocytes.—The effects of probenecid on cytosolic Ca$^{2+}$ and SR Ca$^{2+}$ release were further examined using confocal imaging. Probenecid (0.1 µM) caused a marked increase in SR release (as measured by Ca$^{2+}$ spark frequency) as well as a gradual increase in cytosolic Ca$^{2+}$ concentration (FIGS. 7A and 7B). On average, the spark frequency was increased two fold, from 1.45±0.09 to 2.99±0.24. The cytosolic Ca$^{2+}$ began to increase after 1 minute and typically reached a peak at approximately 5 min after probenecid treatment (FIG. 7C). Once steady state was achieved, cytosolic Ca$^{2+}$ was increased 2.5±0.2 fold under probenecid treatment compared to control (FIG. 7D). When ruthenium red (1 µM) was applied to the myocytes, the increase of cytosolic Ca$^{2+}$ by probenecid was fully blocked (FIG. 7E). Patch clamp experiments indicate that probenecid does not trigger any significant transmembrane Ca$^{2+}$ influx. No measurable inward Ca$^{2+}$ current was detected when myocytes were held at −70 mV and exposed to 0.1 µM probenecid (FIG. 7F, left). However, depolarization of the cell membrane from −70 mV to +10 mV elicited a robust L-type Ca$^{2+}$ current (FIG. 7F, right). Increased SR Ca$^{2+}$ release appeared to play a major role in generating the increased cytosolic Ca$^{2+}$ level. Emptying of SR content with thapsigargin, a SERCA blocker, abolished the change in cytosolic Ca$^{2+}$ by probenecid (FIGS. 7G and 7H).

Probenecid has positive inotropic properties which were previously not recognized, and the effect is mediated by TRPV2 channels.

These data indicate that probenecid increased contractility in the mouse heart as determined by echocardiography and invasive measurements in a dose-dependent manner. However, these studies required the introduction of a jugular catheter which was traumatic to the animals and likely stimulated a sympathetic response. IP injection at a lower dose (100 mg/kg) was observed to have similar effects with a simpler method of administration (and therefore this method and dose was used for the remainder of the studies).

Probenecid has been described to cause transient increases of certain monoamines in the brain, CSF and plasma. These studies suggested that probenecid therapy could raise the concentrations of 5-HIAA and HVA (acid metabolites of serotonin and dopamine, respectively) in dogs and the levels of norepinephrine or DOPAC (also an acid metabolite of dopamine) in humans. A series of experiments was performed to determine if the β-adrenergic (β-ADR) pathway was being stimulated by the administration of probenecid. The conclusion was reached that the increased contractility observed in the in vivo experiments occurred through a calcium dependent mechanism and not through β-ADR mediated phosphorylation of RyR or PLN. This is significant because β-ADR stimulation has been extensively described as having cardiotoxic effects resulting in increased infarct size through increased oxygen demand, induction of cardiocyte apoptosis, and hypertrophy, while β-antagonism is known to be cardioprotective and safe in the treatment of heart failure. Hence, β-ADR stimulation of the heart (directly or indirectly) results in increased contractility but with increased ischemia and cell death and is considered injurious in patients with ischemic heart disease. The data presented herein demonstrates that through ex vivo and in vitro experiments that the mechanism of action of probenecid (i.e. causing increased contractility) is not dependent on these pathways and can be potentially useful as a positive inotrope in patients with ischemic heart disease. Furthermore, a very thorough analysis of all electrocardiographic traces before, during and after administration of probenecid IP or IV on WT and TRPV2$^{-/-}$ mice demonstrated no arrhythmias and no significant changes in any of the measured electrocardiographic variables. This is in stark contrast with commonly used inotropes which result in significant arrythmias, including atrial tachycardia and AV conduction deficits (digoxin) and ventricular and supraventricular arrhythmias (dopamine, dobutamine, isoprotenelol).

While the initial in vivo experiments only describe an increase in contractility, and not a mechanism, we subsequently performed a series of Langendorff experiments in an attempt to separate the systemic from the cardiac specific effects of probenecid. These experiments showed an increase in contractility similar to that which was observed in vivo. A concentration of $10^{-6}$M used in a series of preliminary experiments showed this dose to result in the most reproducible response. Furthermore, the fact that these experiments resulted in corresponding changes in contractility within a similar time frame (5 minutes in all cases) argues convincingly against a significant systemic increase in adrenergic drive as the main cause for the positive inotropism. It was also observed that the increase in contractility was associated with an increased rate of relaxation in isolated myocytes when we measured the rate of shortening (+dL/dt) and the rate of relengthening (−dL/dt), and even though they are not identical, they are comparable to rate of contractility (+dP/dt) and relaxation (−dP/dt) found in ex vivo studies.

Probenecid was previously identified as a TRPV2 agonist in 2007 using TRPV2-expressing HEK293 cells. Fluro-3 AM calcium imaging experiments demonstrated that probenecid elicited a significant increase in cytosolic $Ca^{2-}$ in TRPV2-expressing cells but not in cells expressing other thermo-TRP channels, including TRPV1, TRPV3, TRPV4, TRPM8 and TRPA1. As a member of the thermoTRP channel family, TRPV2 is a $Ca^{2+}$ selective channel activated by noxious heat (>52° C.) and activation of TRPV2 has been shown to lead to $Ca^{2+}$ influx in neuron cells localized to dorsal root ganglia. Probenecid's stimulatory effects on cytosolic $Ca^{2+}$ and myocyte contractility were hypothesized to involve activation of the TRPV2 channel. This hypothesis is supported by the ability of ruthenium red (RR), a blocker of TRPV2 channels, to fully abolish probenecid's effects on both contractility and cytosolic $Ca^{2+}$ level. RR has been established as a general antagonist for TRPV channels, acting by blocking their aqueous pores, however, it has also been shown to affect mitochondrial calcium uptake and ryanodine receptor calcium release.

Having obtained $TRPV2^{-/-}$ mice, in vivo functional experiments were performed which showed that $TRPV2^{+/-}$ mice had an approximately 50% decrease in contractility, while $TRPV2^{-/-}$ mice had absolutely no change in function after exposure to probenecid (100 mg/kg). These findings argue for the necessity of TRPV2 receptors for increased contractility, but do not prove (as it is a whole body and not a cardiac specific knockout), that the effect is directly dependent on these receptors in the cardiomyocyte.

At the cellular level, the data show that probenecid increased contractility in mouse ventricular myocytes, though cardiac fibroblasts were not investigated separately. TRPV2 has been found to be present and active in various types of fibroblasts, which may potentially play a role in the observed effects. It was also found that probenecid increased the amplitude of the $Ca^{2+}$ transients, and in quiescent myocytes a gradual increase of the cytosolic $Ca^{2+}$ concentration was observed. Intriguingly, no measurable inward $Ca^{2+}$ current was detected upon exposure to probenecid, suggesting that $Ca^{2+}$ influx into the myocyte was not the direct source of the probenecid-triggered increase in cytosolic $Ca^{2+}$ levels. Rather, enhanced SR $Ca^{2+}$ release appeared to play a major role in the cytosolic $Ca^{2+}$ increase. It was found that probenecid markedly increased $Ca^{2+}$ spark frequency and emptying the SR with a SERCA blocker abolished the effect of probenecid on cytosolic $Ca^{2+}$.

EXAMPLE 2

The data in Example 1 demonstrates that probenecid has positive inotropic properties which were previously not recognized. The data in Example 1 also demonstrates that probenecid does not have significant malignant electrophysiologic properties (i.e no arrhythmias were noted) and hence may be a useful drug for the treatment of heart failure. As other positive inotropes are known to be cell injurious, the data in Example 2 demonstrate the potential cytotoxic/apoptotic properties of probenecid and its potential use as a positive inotrope in a mouse model of ischemic heart disease. These data suggest that probenecid functions through a mechanism separate from conventionally used inotropes, and that it will increase contractility and improve heart function after ischemia without decreasing cell survival or increasing apoptosis. The data were generated in vitro using the HL-1 cardiac cell line in addition to a well-established and clinically relevant mouse model of ischemia/reperfusion (I/R) and monitored cardiac function via echocardiography.

Methods

Cell Viability Assays—Cell viability was assessed using the ApoTox-Glo Triplex Assay (Promega, Madison, Wis.) per manufacturer's instructions. Briefly, HL-1 cells were seeded in 96 well plates at a density of $1\times10^4$ cells/well and allowed to grow overnight in Claycomb media supplemented with 10% FBS, 100 U/ml penicillin/streptomycin, and 2 mM L-glutamine. Cells were treated with indicated doses of probenecid or isoproterenol in supplemented growth media at 100 µl total volume and allowed to incubate overnight. GF-AFC viability was then added to ApoTox-Glo Assay Buffer at a ratio of 10 µl GF-AFC to 2.0 ml Assay Buffer and 20 µl of this mixture was added to each well and cells were incubated at 37° C. for 30 minutes. Fluorescence was measured at 400 nm (ex)/505 nm (em) and the data was normalized to untreated control cells.

Water soluble probenecid was used for all of the experiments.

Imaging and measurement of Ca2+ fluorescence.—HL-1 cells were obtained as described above. Dissociated cells were plated on glass cover-slip (GG-25-polylysine #1, Neuvitro, Calif.) placed inside each well of six-well plates (BD Falcon). Acquisition of images were done at 40-65 Hz by using LSM 510 Meta system equipped with the inverted Axiovert 200 M BP (Carl Zeiss Microscopy, LLC, Thornwood, N.Y.) and LSMS Software. Image acquisition was done with Plan-Apochromat 40x/water with frame size of 512 (X) and 256(Y). To optimize the speed of acquisition, the acquisition area was limited to a few cells. Cells were loaded with the Ca2+ indicator dye FLUO4-AM (Molecular Probes, Life Technologies, Carlsbad, Calif.) diluted in Tyrode's solution (Sigma-Aldrich, St. Louis, Mo.) to a final concentration of 1 µM) for 20 min at 37° C. and then washed twice for 5 minutes in Tyrode's solution. Coverslips with adherent HL1 cells pre-loaded with dye were placed in the recording chamber that was mounted on an inverted microscope and subsequently bathed in Tyrode's solution before perfusion of probenecid. After focusing and taking baseline images cells were perfused with probenecid ($10^{-8}$ to $10^{-4}$ M in different experiments) at a rate of 0.5 ml/15 sec. For these experiments, image exposure time was 5 ms with a camera on-chip multiplication gain of 500-600, and there were 700 cycles for each run of the different concentrations. The 488-nm line of a multiline argon laser excited FLUO-4 and an electronic shutter controlled cell exposure to the laser. Off-line Image processing was performed with LSMS software and statistical analyses on the data were done using MS Excel (Microsoft) and SAS 9.2(SAS Institute, Cary, N.C.).

Peak fluorescence before perfusion ($F_0$) and that after perfusion (F) were determined manually after acquisition of images from the saved LSM files. Circular areas within the cytosol of each cell of the saved images over the entire duration of respective experiments were used to determine changes in fluorescence before and after perfusion.

Normalized fluorescence, determined as a quotient of $F/F_0$, was used as a variable to compare the relative changes in fluorescence at different incremental concentrations during statistical analyses. Maximal likelihood estimates of the dependent variable (log $[F/F_0]$) was determined as a function of concentration of the probenecid (log [probenecid], M) dose using proc mixed modeling with repeated measures in SAS. A dose-response relationship was modeled using linear regression and linear regression plot of the model.

Detection of cell death.—Hearts were obtained from mice which were exposed to probenecid or sugar-water (control) under various conditions. There were 4 groups of mice for these experiments, including control (n=4), probenecid treated water (n=4), control after I/R injury (n=4) and probenecid treated water after I/R injury (n=4). The hearts were removed, rinsed with PBS, fixed with 3.7% buffered formaldehyde (after 30 minutes the buffer was changed) and dehydrated (hearts were placed in 70% ethanol after 18-24 hours). The samples were embedded in paraffin, sectioned into thicknesses of 6 µm, each 10 µm apart, and 2 heart sections were placed onto each slide. The slides were prepared using the in situ apoptosis detection kit, CardioTACS (Trevigen, Gaithersburg, Md.) according to the manufacturer's instructions. After staining, the slides were placed on a microscope (Olympus 1×71) and the number of apoptotic cells was counted by two separate and blinded readers in 5 fields of view for each heart section. The total number of cells was also determined for the same field, and the apoptotic cells were calculated to be a percentage of the total cells. These values were then averaged for each group; probenecid and control mice.

Animals—All mice (C57BL6J, Jackson laboratories, Bar Harbor, Me.) were males at 12-16 weeks of age.

Ischemia/Reperfusion methods—Mice were anesthetized with sodium pentobarbital and the heart exposed through a left thoracotomy at the level of the fourth intercostal space. The mice were intubated and placed on a mini-ventilator (Harvard apparatus, Holliston, Mass.). A loop occluder was placed around the left anterior descending artery (LAD), and tightened, occluding it for either 30 minutes or 45 minutes. After surgery, the thorocotomy was sutured in layers, and the animal was allowed to recover.

All mice had echocardiographic measurements as described after 24 hours post-IR to determine the severity of the injury in vivo.

Echocardiography methods—All echocardiographic studies were performed as previously described for Example 1.

Ischemia/Reperfusion followed by probenecid bolus—I/R studies were performed as described above with 45 minutes of ischemia. Echocardiography was performed at 24 hours post-I/R and weekly thereafter. There were 4 groups of mice, saline and probenecid with subgroups of mice with a post I/R EF of 50 to 60% (n=5 for saline and n=6 for probenecid) or those with a post I/R EF of 40 to 50% (n=6 for saline and n=6 for probenecid). The probenecid mice were treated with an IP bolus of 100 µl (100 mg/kg) while the saline groups only received 100 µl of saline IP. The mice were imaged at 5 minute intervals for a total of 30 minutes.

Ischemia/Reperfusion followed by oral probenecid—The I/R studies were performed as described above with 45 minutes of ischemia and echocardiography was performed at 24 hours post-I/R and weekly thereafter for 4 weeks. After 24 hours, the mice were randomized to probenecid treated water or untreated water cages. The probenecid was dissolved in water containing 5% sucrose at a concentration of 0.5 µg/ml. The water was changed twice a week and the volume was measured before and after consumption to determine the approximate dose. The mice were housed 2 to a cage for a more accurate assessment of total dose administered.

Probenecid bolus followed by Ischemia/Reperfusion—Either saline or probenecid (100 mg/kg) were administered IV 15 prior to a 45 minute coronary occlusion (i.e., at the time of maximal increase in contractility). At twenty-four hours post-I/R, echocardiography was performed and the hearts subsequently removed for determination of infarct size and normalized to the risk region.

Statistical Analysis—All data are expressed as means±standard error of the mean (SEM). Results were analyzed with a paired and unpaired Student's t-test and one-way ANOVA as needed. P values of ≤0.05 were considered significant. For all in vivo studies, power analysis was employed to determine the group size necessary to determine whether significant differences exist between endpoint measures in control versus experimental groups as previously described.

Results

Figure 8A:
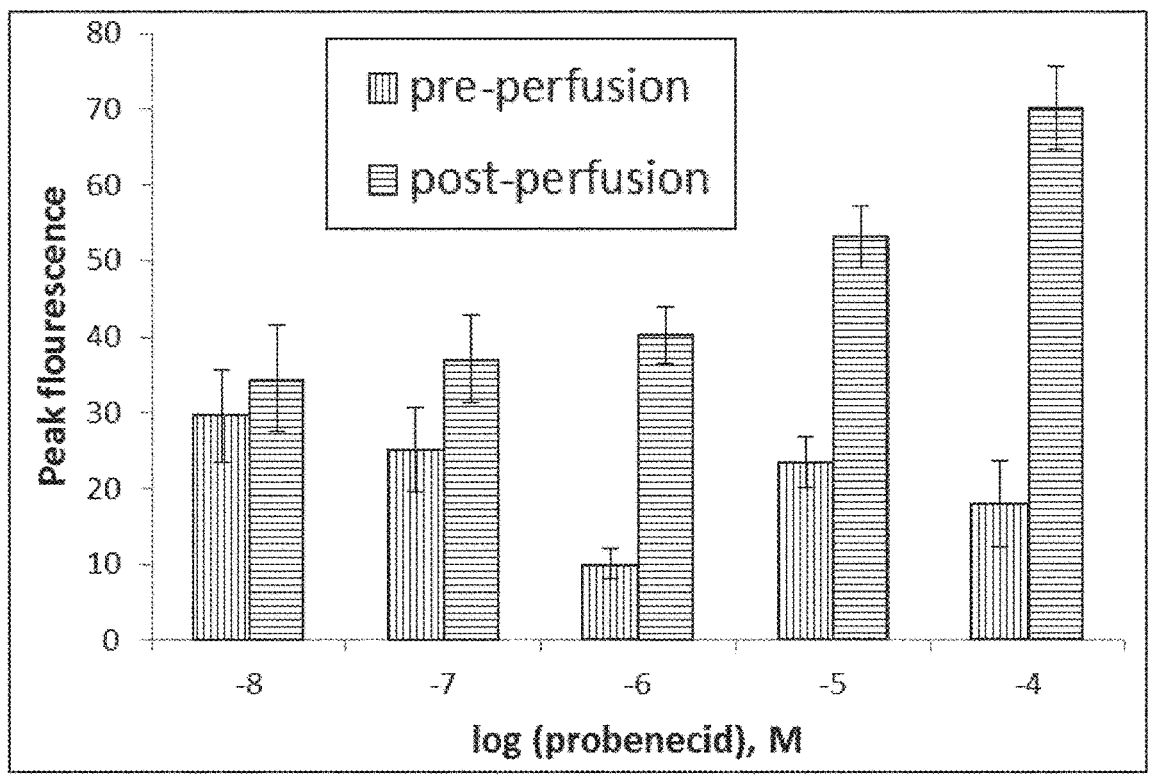
FIG. 8A is a bar graph illustrating the peak cystolic fluorescence before and after various doses of probenecid

Probenecid does not induce cell death in vitro.—For these experiments HL-1 cells were used to assay the effect of probenecid. No significant differences in the median measurement of the peak cytosolic fluorescence before and after perfusion of probenecid $10^{-8}$ were observed. Else the median of peak fluorescence after perfusion of higher probenecid concentrations were significantly higher than that before perfusion (FIG. 8A).

Figure 8B:
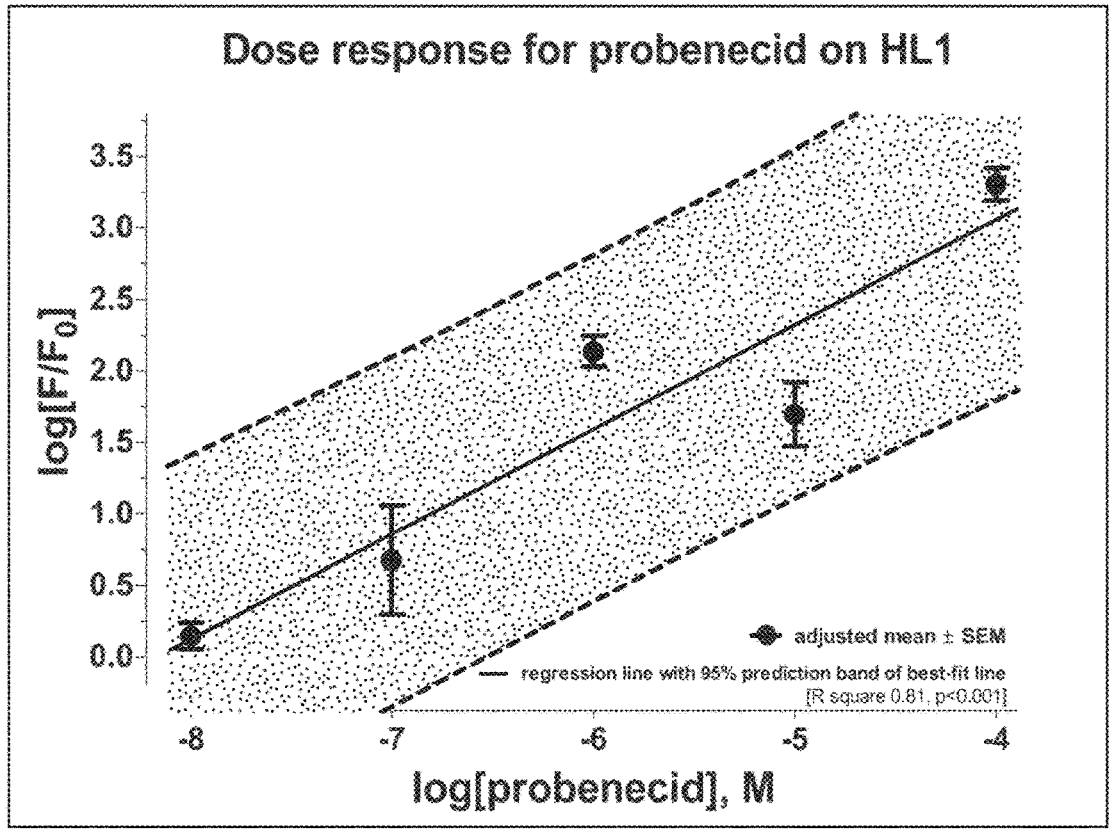
FIG. 8B is a linear regression illustrating a dose response curve of normalized fluorescence for various doses of probenecid.

A log-dose response curve for logarithm of normalized fluorescence ($F/F_0$) with incremental concentrations ($10^{-8}$-$10^{-4}$) showed linear response with increasing doses of probenecid. The R-square value for best-fit regression line of the dose-response was 0.67 (FIG. 8B). There were statistically significant differences in the response with the lowest probenecid concentration $10^{-8}$ vs. other higher concentrations (p-values ranging between 0.001-0.01 for these pairwise comparisons.

Figure 8C:
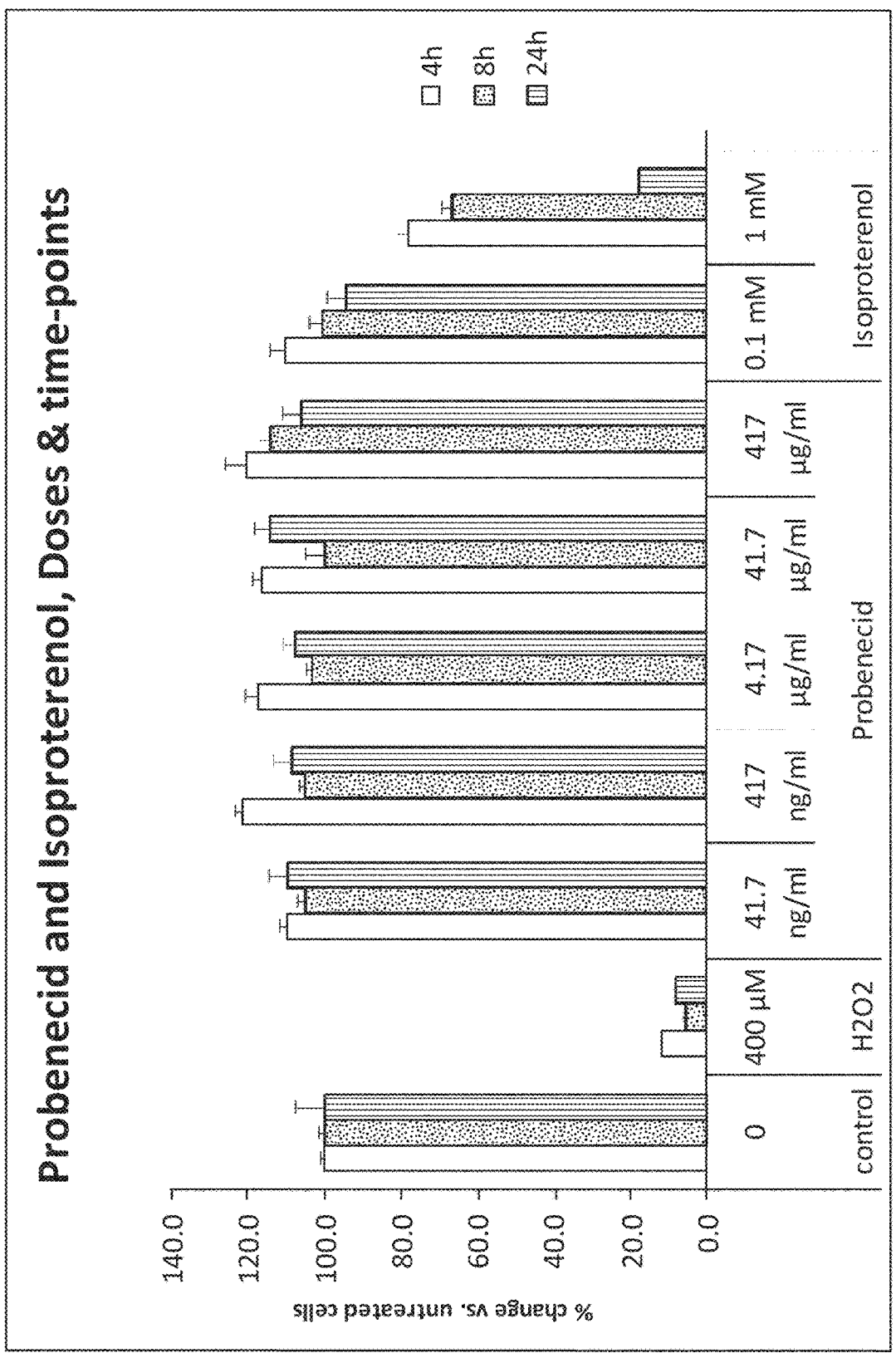
FIG. 8C is a bar graph illustrating no significant cell death with various doses of probenecid while treatment with 1 mM isoproterenol resulted in significant cell death at just 4 hours and was indistinguishable from $H_2O_2$ positive controls by 24 hours after treatment.

In addition, treatment of HL-1 cells with increasing doses of probenecid does not result in any detectable cytotoxicity at 4, 8 or 24 hours following treatment (FIG. 8B). However, similar treatment with 1.0 mM isoproterenol induced a significant amount of cell death after 4 and 8 hours of treatment (*p<0.001) and substantial cell death at 24 hours (**p<0.001) where less than 20% of the cells were still viable, which was indistinguishable from the $H_2O_2$ positive control (FIG. 8C).

Figure 9:
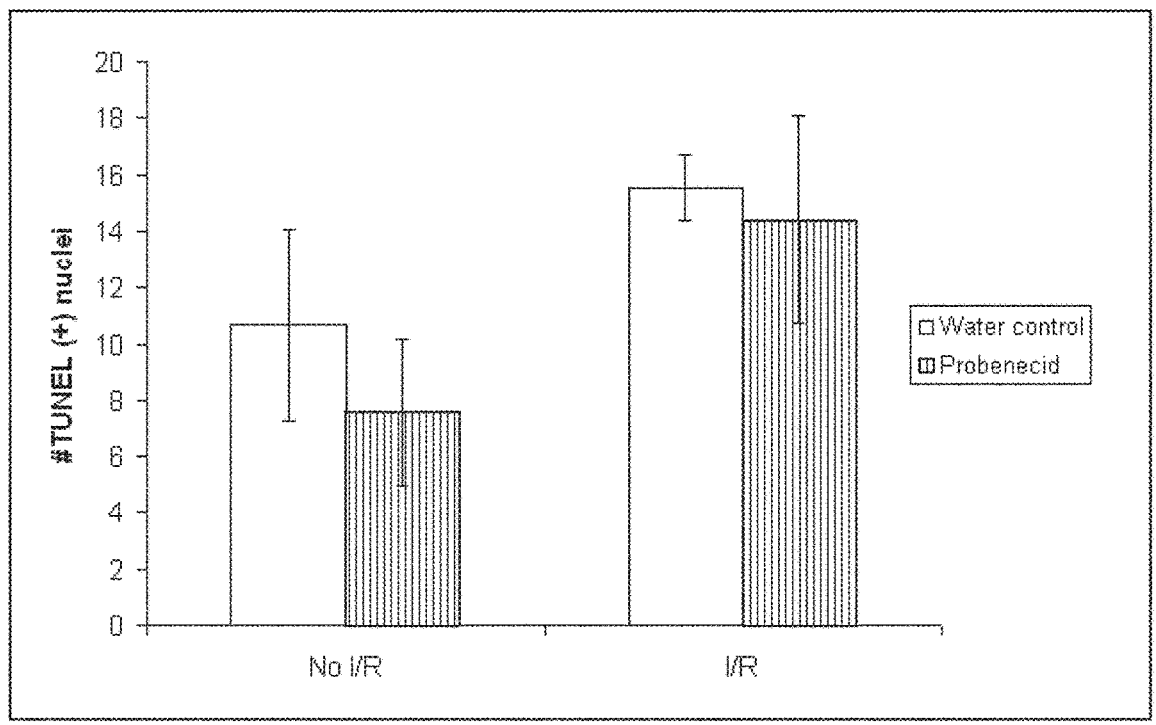
FIG. 9 is a bar graph illustrating no significant difference in cell death with and without pretreatment with probenecid as noted via TUNEL stained nuclei in mice with and without ischemic injury.

Probenecid does not cause significant myocyte cell death in vivo. Oral probenecid therapy in healthy mice did not induce significant apoptosis after 2 weeks of treatment where the average intake of probenecid was estimated to be 190.56±6.33 mg/kg/day based on the water consumption of paired mice per cage. Furthermore, mice that were subjected to I/R and subsequently randomized to either probenecid treated water or untreated water did not show significant differences in amount of cell death between the probenecid treatment and untreated water (FIG. 2A). As expected, mice subjected to I/R injury did demonstrate higher levels of apoptosis in comparison to non-I/R mice (FIG. 9).

Figure 10A:
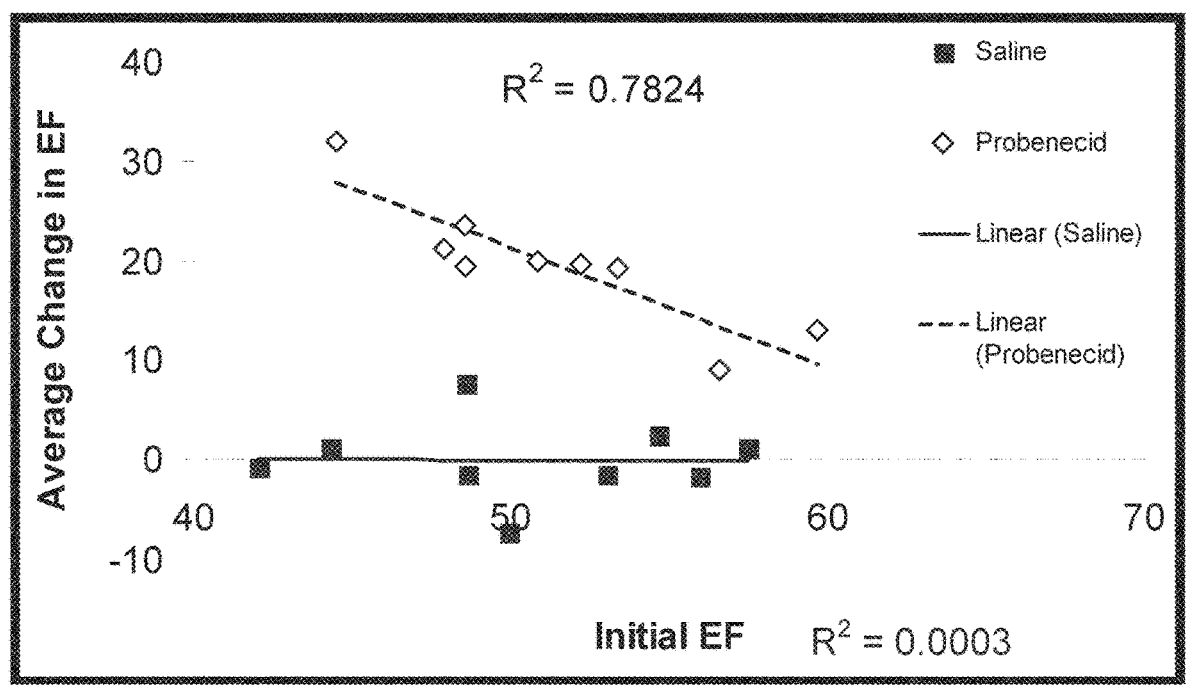
FIG. 10A is a scatter plot illustrating the correlation between initial EF and the change in EF in mice subjected to I/R injury and followed via echocardiography for cardiac function after probenecid administration and the groups divided by initial EF with 50-60%.
Figure 10B:
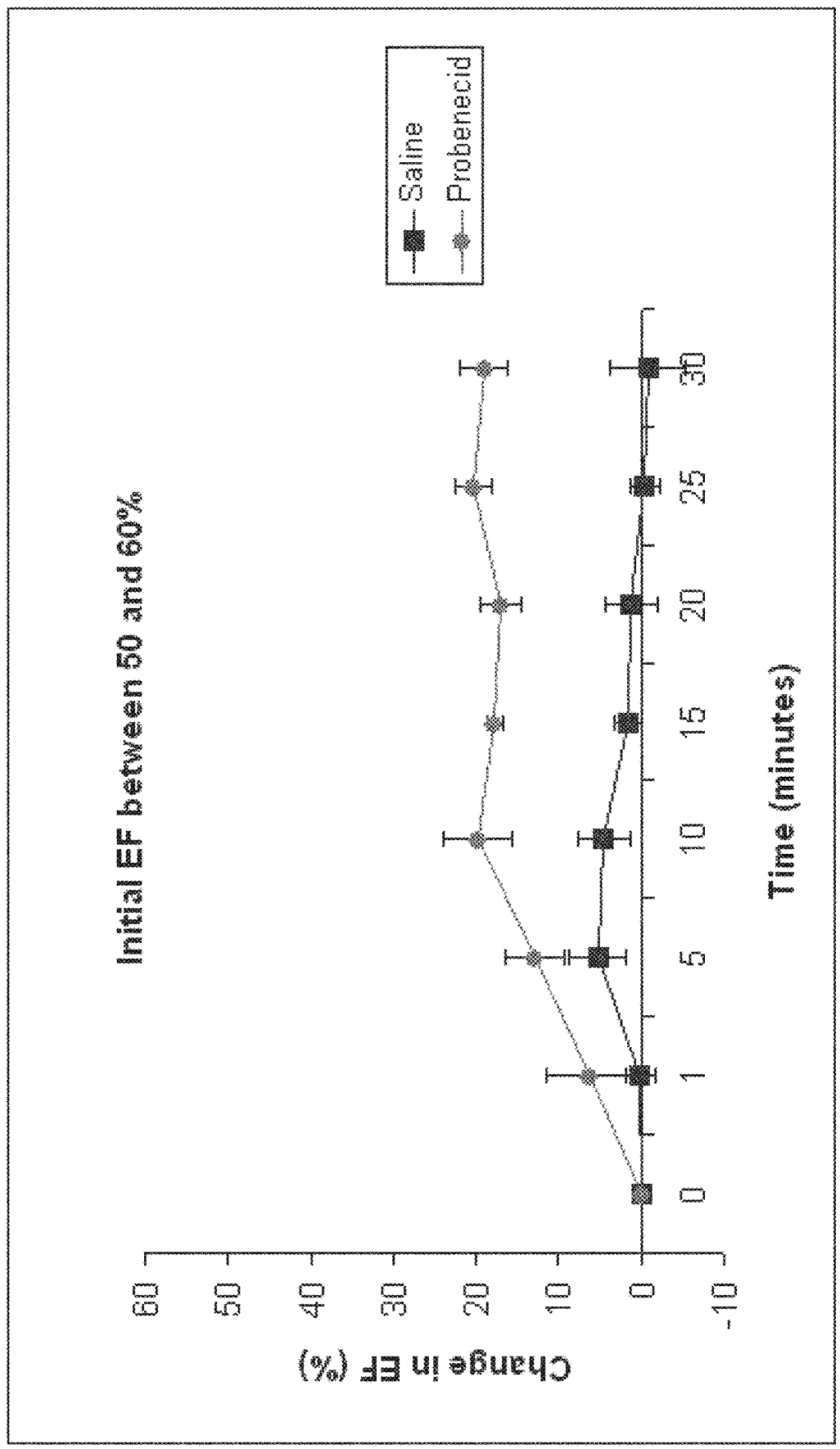
FIG. 10B is a curve illustrating the correlation between initial EF and the change in EF after probenecid administration representing minimal damage, 50 and 60%.
Figure 10C:
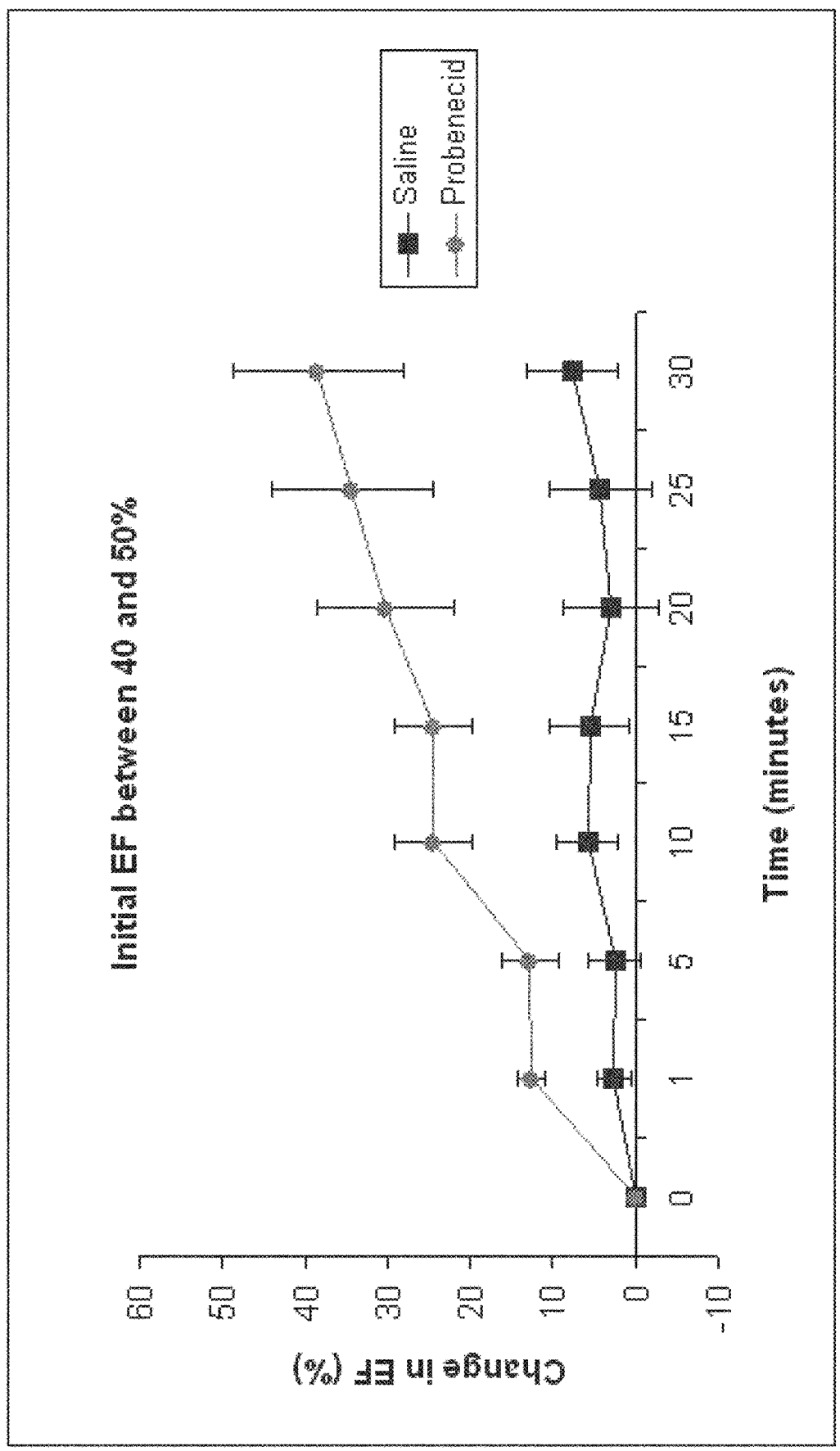
FIG. 10C is a curve illustrating the correlation between initial EF and the change in EF after probenecid administration representing more significant myocardial injury.

Bolus probenecid improves function acutely in ischemically damaged hearts. After I/R injury, probenecid administered IP caused a statistically significant increase in EF in all treated mice. Interestingly, treatment with probenecid was able to more strongly enhance function in mice that display a lower initial EF, as indicated by the strong correlation between the probenecid-induced increase in EF and initial EF (FIG. 10A). This effect occurred in a similar time frame as previously reported, with an initial rise observed at 1 and 5 minutes in both groups. However, though the peak effect was found at 10 minutes (change in EF was 19.72±4.10%) in mice with a higher initial EFs (50-60%), probenecid continued to enhance contractility throughout the full 30-minute experiment in mice with lower initial EFs (40-50%) (FIGS. 10B and 10C).

Oral probenecid improves function after ischemia and reperfusion injury. Twenty-four hours after I/R injury, there was no significant difference in EF or LV Vol;d between the mice subsequently randomized to water control and probenecid treatment (EF: 43.44±2.05 and 41.81±3.40, respectively, p=0.65; LV Vol;d:66.51±2.65 and 71.99±5.44, respectively, p=0.39).

Figure 11A:
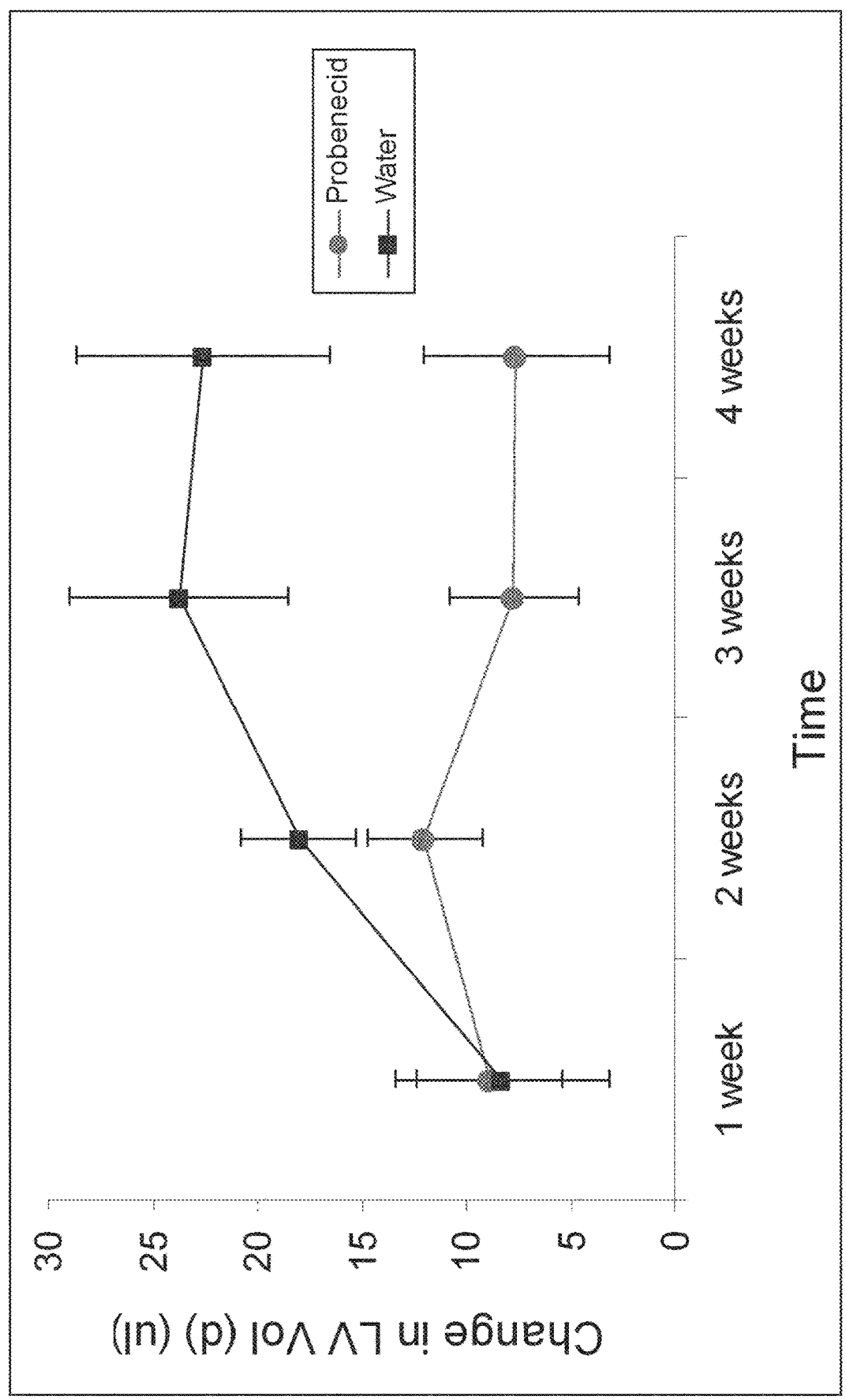
FIG. 11A is a curve illustrating that after I/R injury water treated mice had an increased left ventricular volume during diastole (LV Vol;d) as compared to mice treated with probenecid
Figure 11B:
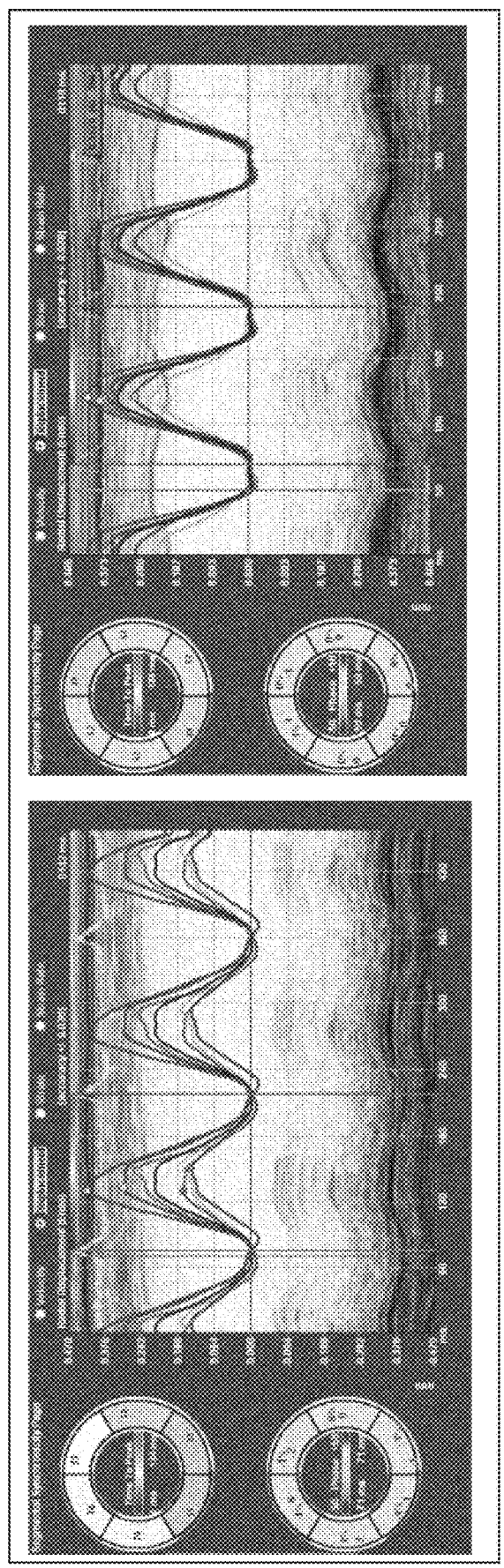
FIG. 11B is an echocardiogram showing that probenecid mice had a improved myocardial contractility as measured via higher displacement compared to water treated mice
Figure 11C:
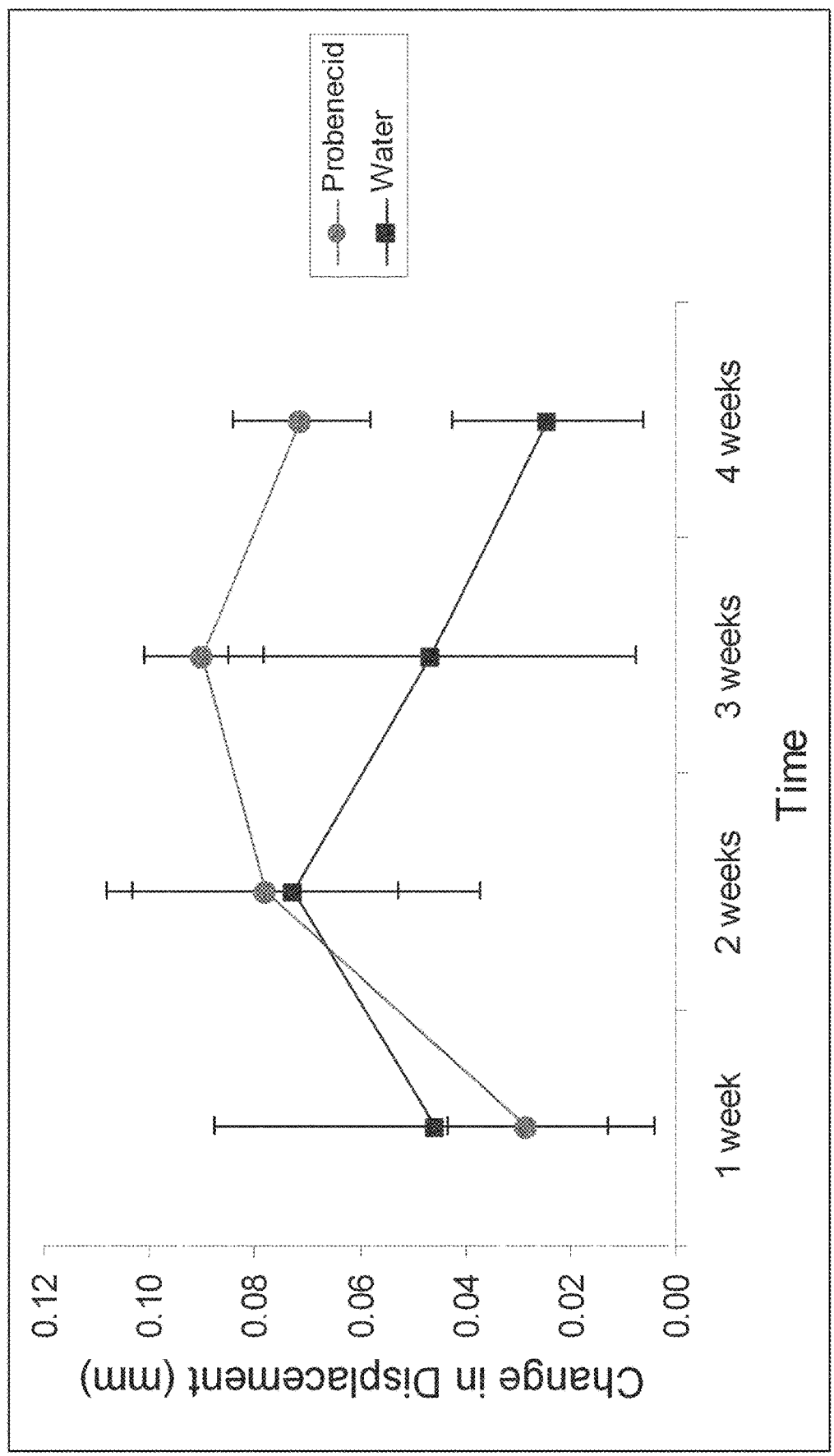
FIG. 11C is a curve illustrating the echocardiogram data of FIG. 11B.
Figure 11D:
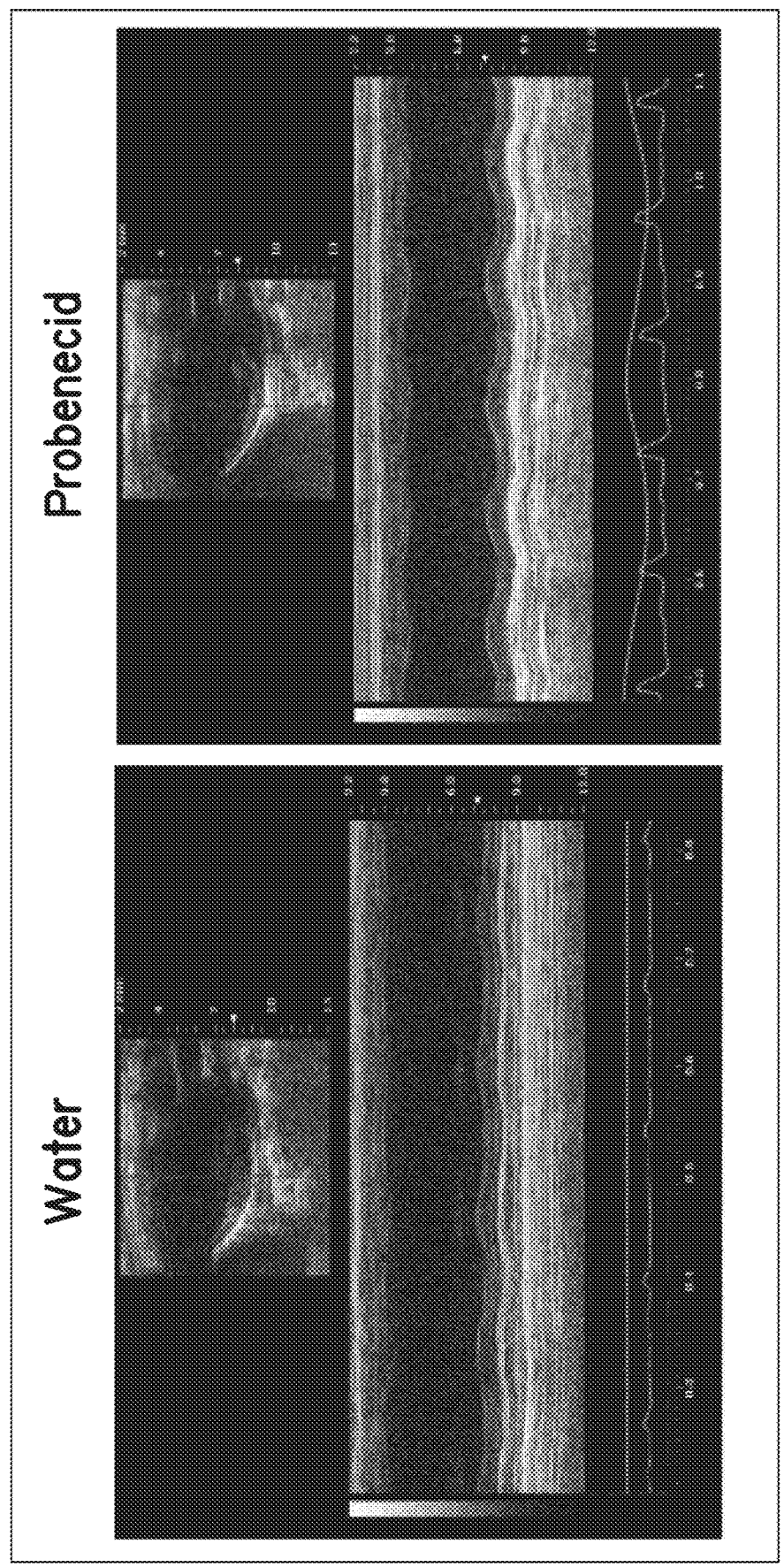
FIG. 11D is an echocardiogram showing that there was a slight (but not statistically significant) increase in the change in EF with probenecid
Figure 11E:
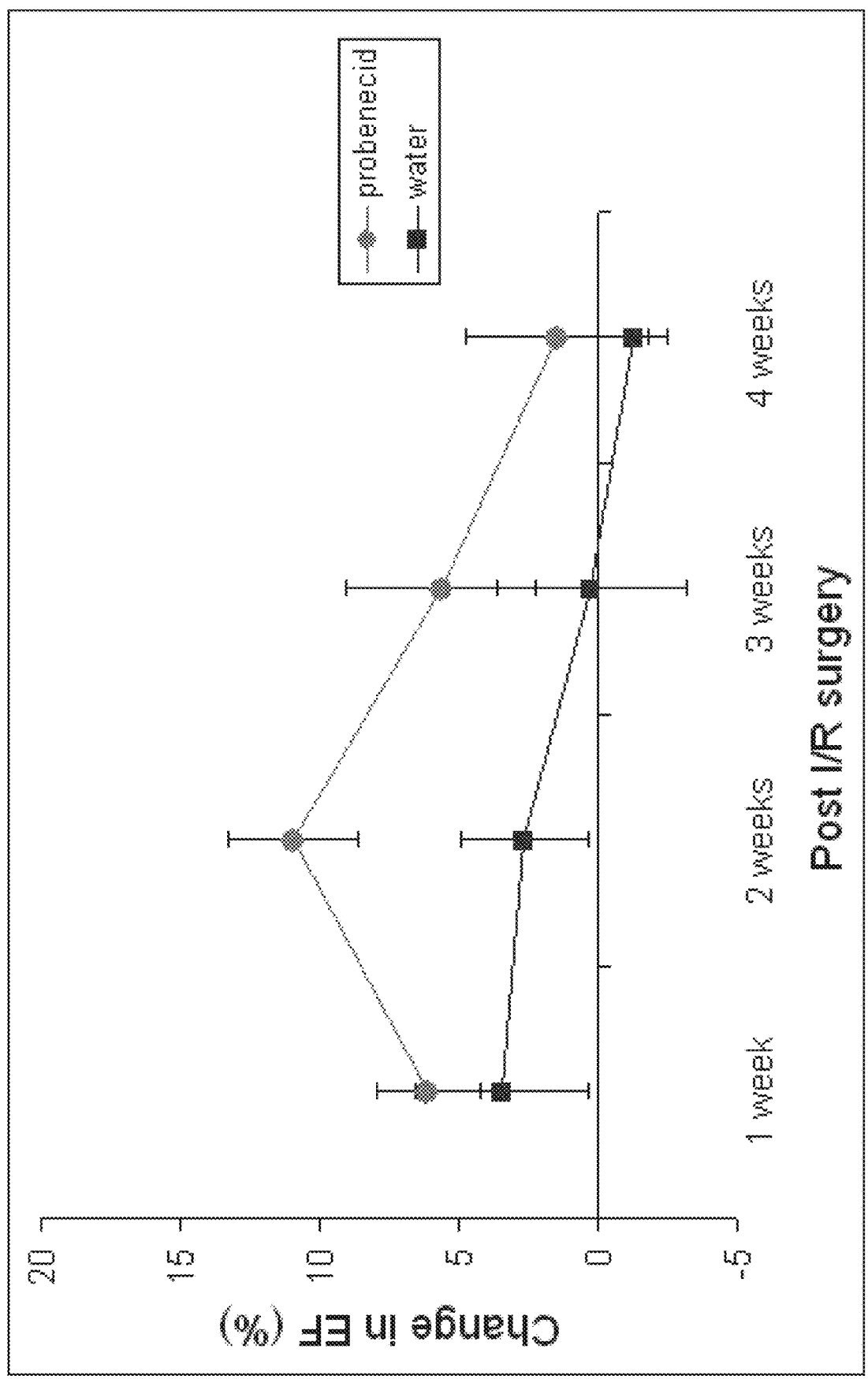
FIG. 11E is a curve illustrating the echocardiogram data of FIG. 11C.

The LV cavity size (LV Vol;d) was minimally dilated after 1 week but did not worsen over the course of the experiment in the probenecid group, though it increased further in the sham treated mice (water 22.55±4.47 and probenecid 7.59±6.08, p=0.076, FIG. 11A). In addition, the water treated mice had a decrease in radial displacement as compared to the probenecid treated mice (representative echocardiogram pictures are displayed in FIGS. 11B and 11C), indicating preserved myocardial function (water 0.018±0.018 and probenecid 0.071±0.013, p<0.05, FIGS. 11D and 11E). Thus, despite equal initial ischemia/reperfusion injury, the probenecid-treated mice had preserved function relative to controls.

Figure 12A:
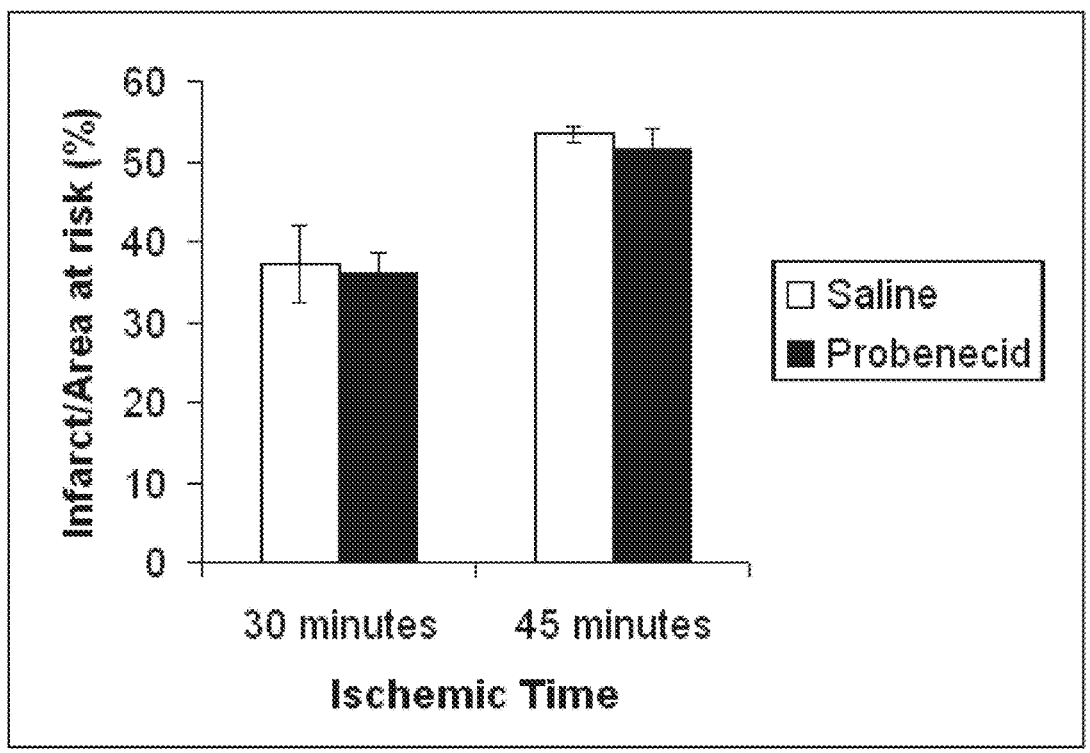
FIG. 12A is a bar graph illustrating the infarct size was higher for 45 minutes of ischemia compared to the 30 minute ischemia, however there was no difference between control mice and mice pre-treated with 200 mg/kg probenecid at either time point.
Figure 12B:
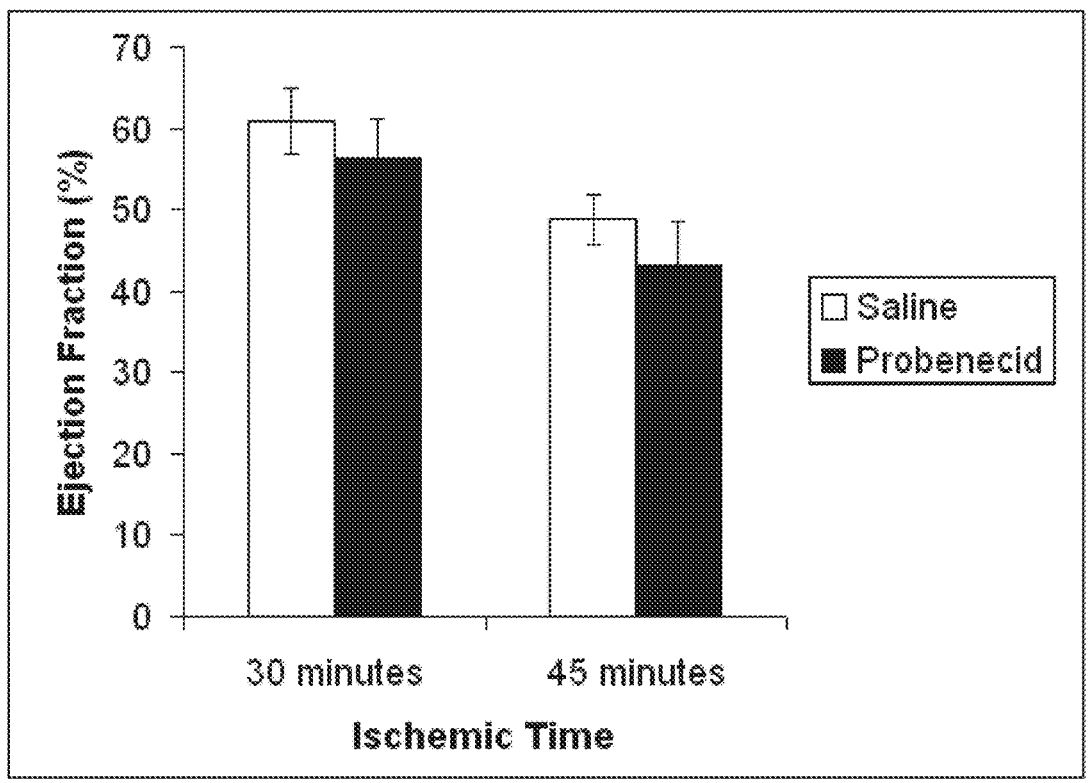
FIG. 12B is a bar graph illustrating that there was no difference between control and pretreated mice at either time point with regards to EF.
Figure 12C:
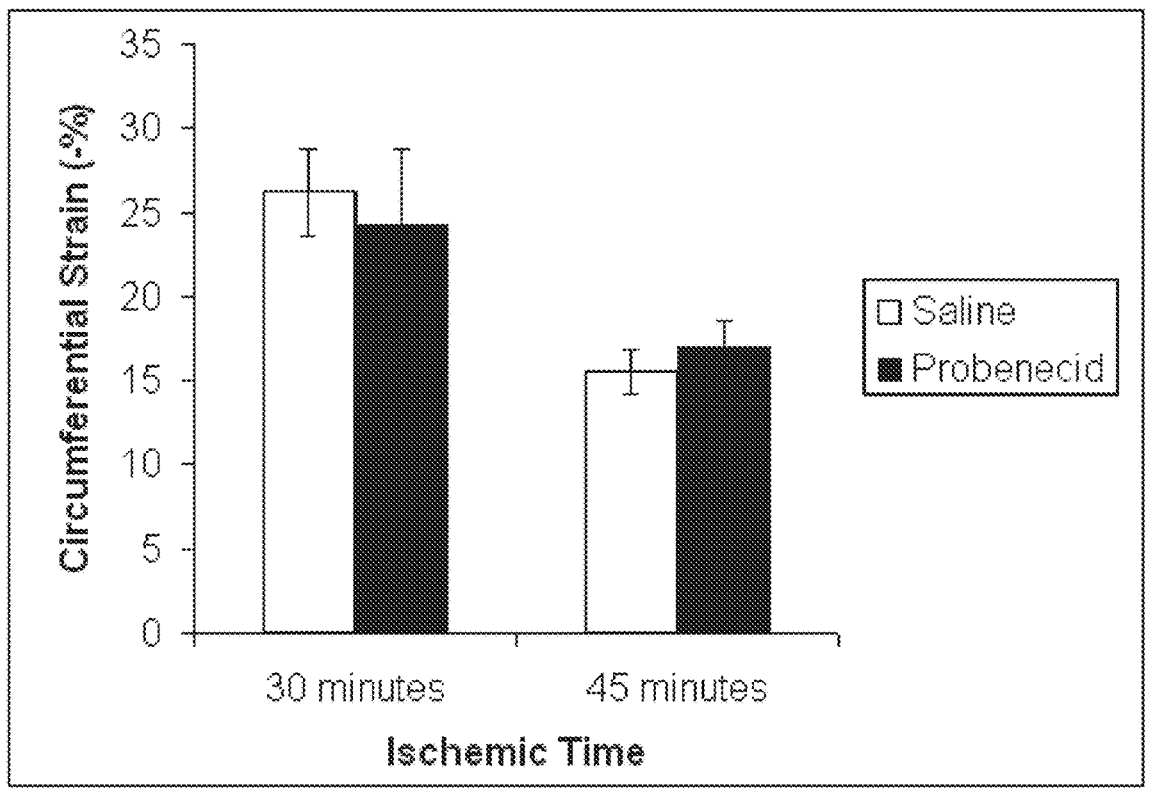
FIG. 12C is a bar graph illustrating that there was no difference between control and pretreated mice at either time point with regards to circumferential strain.
Figure 12E:
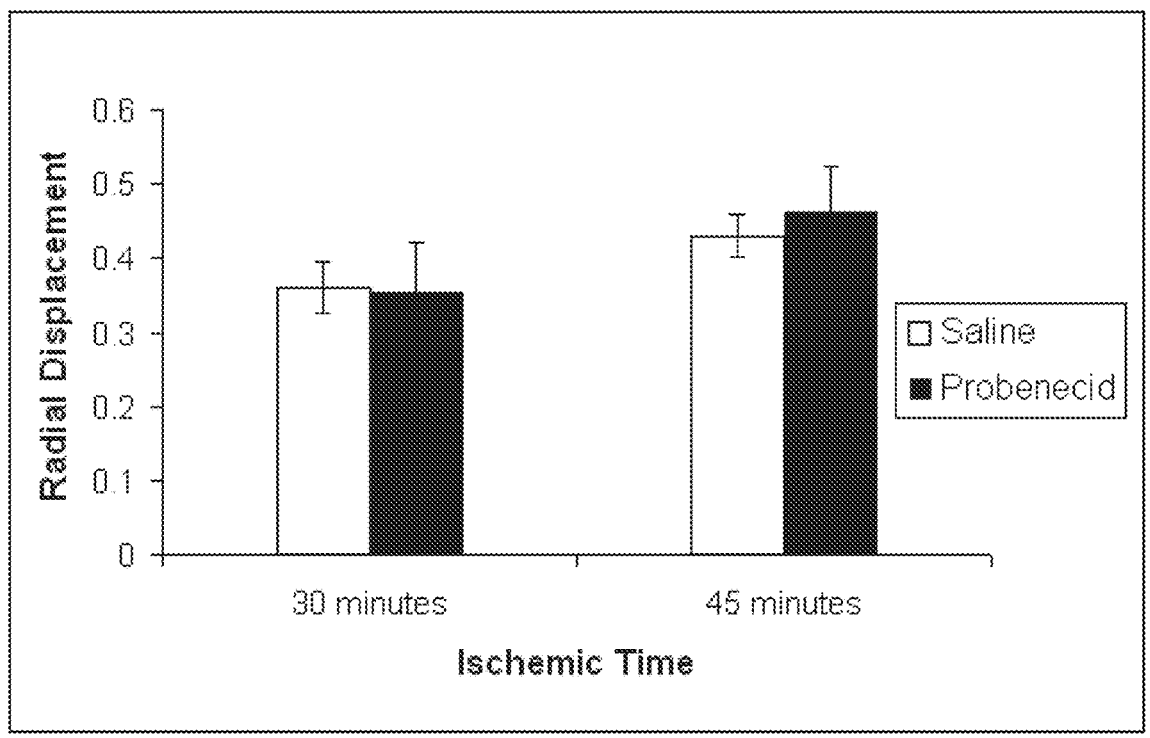
FIG. 12E is a bar graph illustrating that there was no difference between control and pretreated mice at either time point with regards to radial displacement.
Figure 12D:
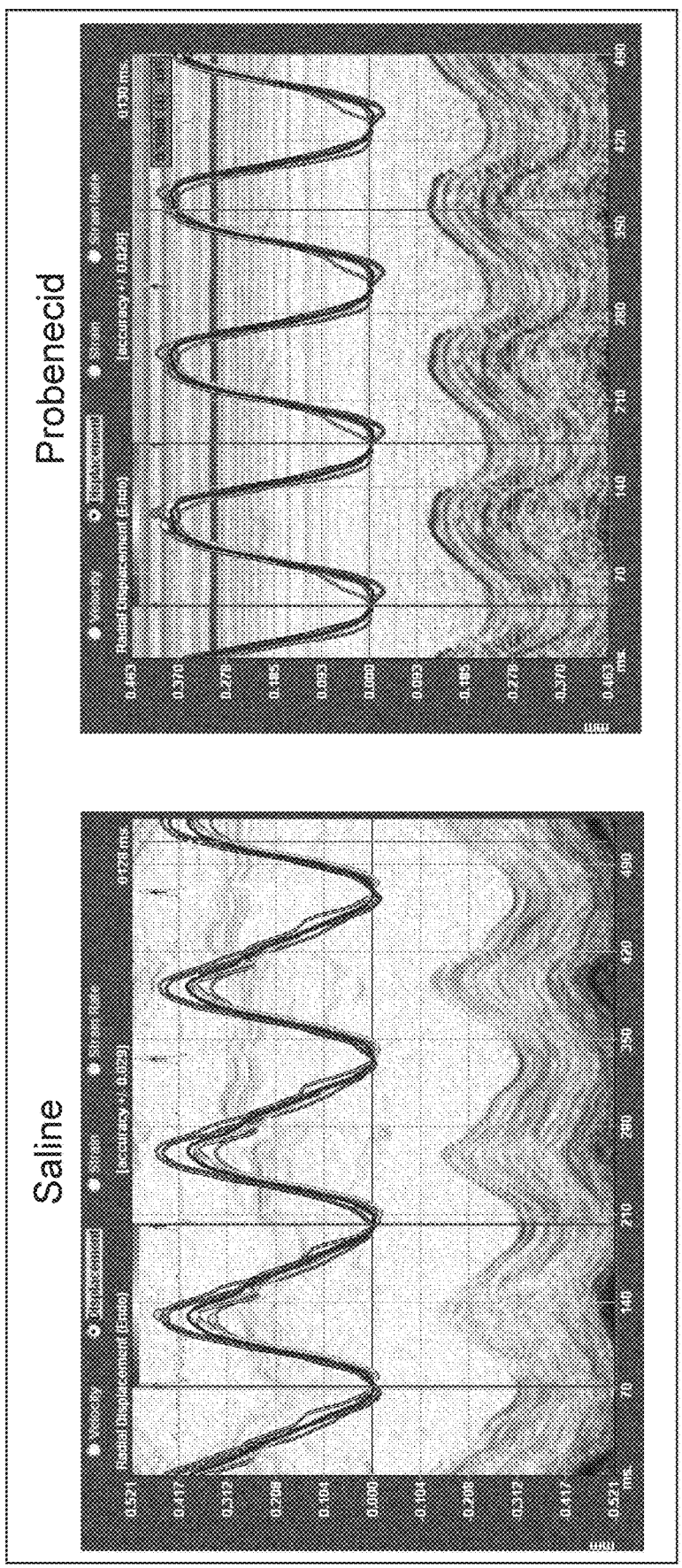
FIG. 12D is an echocardiogram showing IR with pre-treatment with probenecid.
Figure 13:
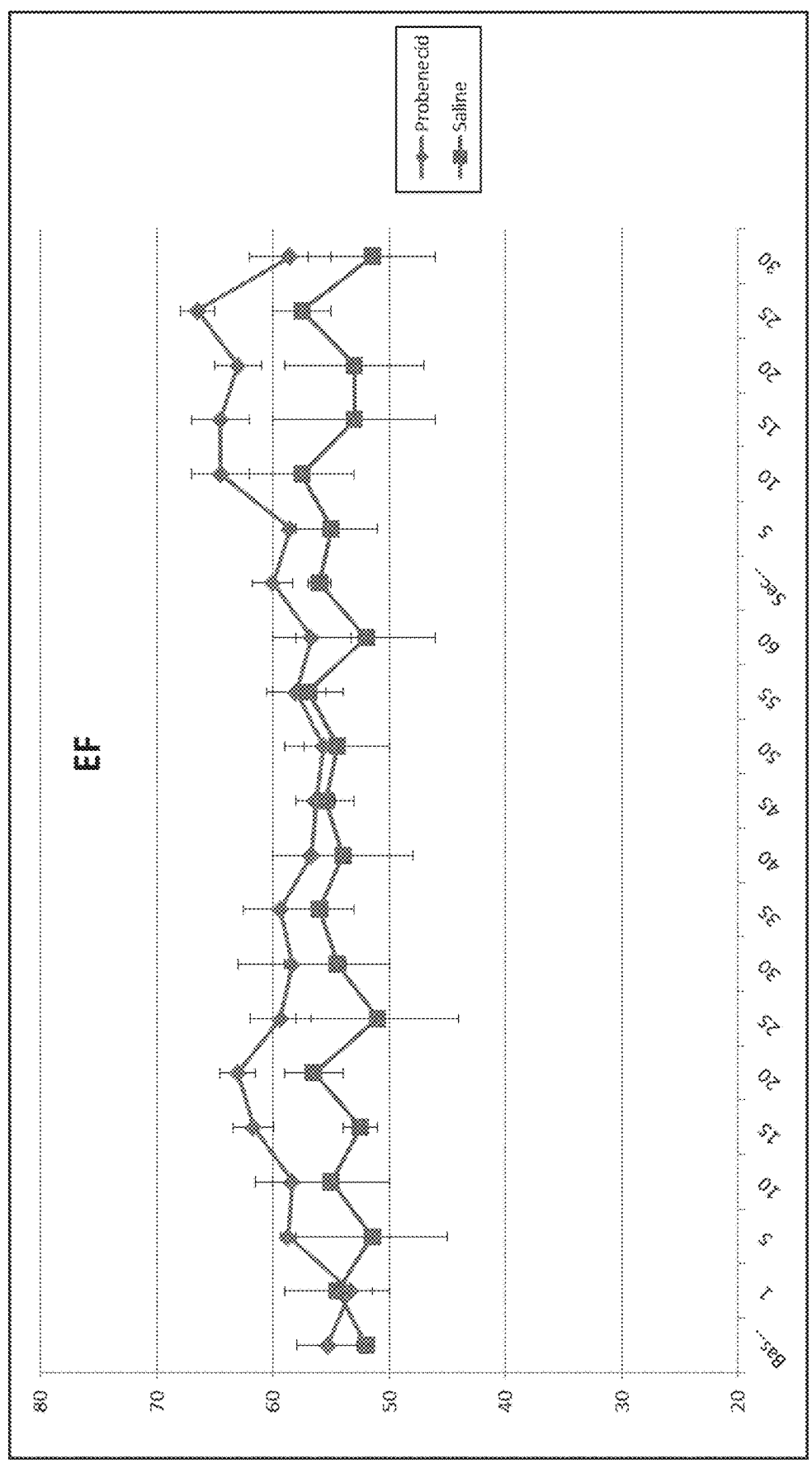
FIG. 13 is a curve illustrating the improvement in cardiac function as measured via echocardiography in a healthy pig model after various doses of probenecid IV.
Figure 14:
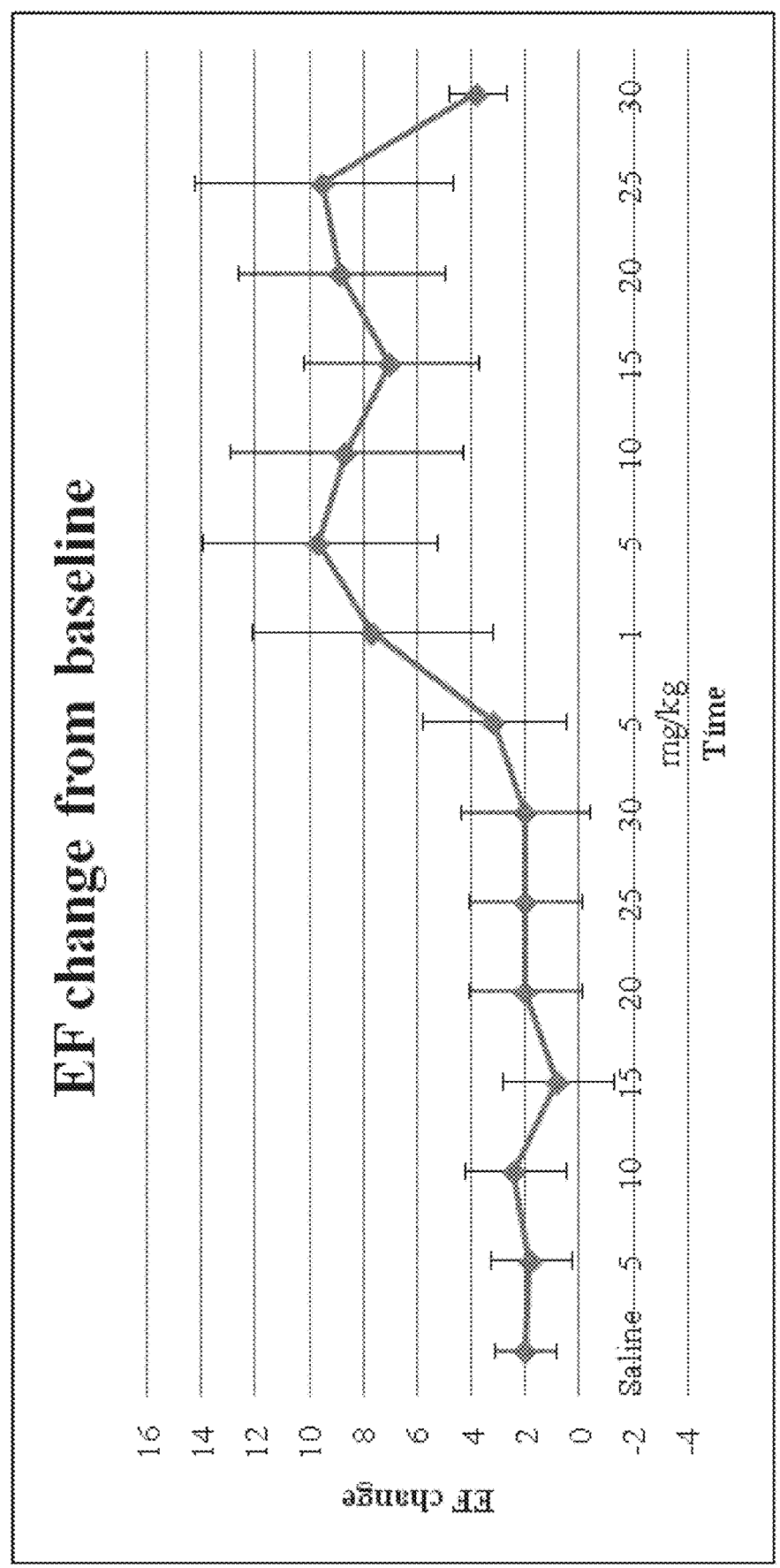
FIG. 14 is a curve illustrating no change in cardiac function after saline administration and a rapid increase in EF after 5 mg/kg IV administration of probenecid.

Probenecid does not worsen ischemia and reperfusion injury. It is well established that adrenergic stimulation results in increased myocyte contractility but is also associated with cellular damage and death through several mechanisms including increased metabolic requirements and induction of apoptotic mechanisms. The present study was conducted to evaluate the effects of increased contractility observed with probenecid administration during an ischemic event. The infarct size as measured via histology was not significantly different in mice pretreated with probenecid in comparison to saline for both the 30 and 45 minute ischemia groups after 24 hours of reperfusion (FIG. 12A). Furthermore, the systolic function in these mice (as measured via EF and global circumferential strain) was not significantly different between the saline and probenecid treated groups (FIGS. 12B and 12C). Interestingly, when regional wall motion was determined via strain imaging measuring radial displacement, there was also a significant difference in the function of the anterior wall after 30 minutes as compared to 45 minutes of ischemia, but no difference between the treatment groups (30 minutes, saline 0.43±0.02 mm vs probenecid 0.46±0.06 mm and 45 minutes, saline 0.36±0.03 mm. vs. 0.35±0.06 mm, p>0.05 between both saline and probenecid treated groups) (FIGS. 12D and 12E).

Discussion

Data from Example 1 demonstrated that probenecid, an FDA approved drug, has inotropic properties, which went unrecognized for decades. These experiments demonstrated that probenecid increased cytosolic $Ca^{2+}$ levels resulting in increased contractility independent of β-adrenergic signaling. The lack of stimulation of the β-AR pathway initiated the research presented herein, as adrenergic stimulation has been previously shown to increase myocardial metabolic demand, stimulate apoptotic pathways and cause myocyte hypertrophy. This has been reflected in numerous clinical trials involving traditional β1-agonists (dobutamine, dopamine) as well as PDIs (i.e milrinone) which have found that even as symptoms and hemodynamic parameters improve, the short and long term mortality of patients exposed to these drugs increases.

The two principal findings of this work address these issues: 1) the lack of cell death associated with the improved inotropic response and 2) the positive inotropic effect of probenecid in an ischemically damaged heart.

Regarding the latter, initially a clinically relevant model of ischemic heart disease was used in which ischemia is caused for a short period time and subsequently the vessel is opened. This pathophysiology is not dissimilar to the common clinical course of an acute myocardial infarction in which revascularization is accomplished in a short period of time and the subsequent ischemic damage is minor. the present model was able to detect small decreases in systolic function due to the high frequency probe used which permitted us to dichotomously divide the mice between mild damage (EF of 50-60%) and moderate damage (EF of 40-50%). The present finding that probenecid, not only increases contractility as previously described, but also that the increase is inversely correlated with post-ischemic EF (the moderately damaged group, EF of 40-50%, showed a larger increase in EF) importantly lends credence to the translational potential of this drug for use in patients with moderate systolic dysfunction.

The mechanism of action of probenecid in the undamaged/non-ischemic myocyte was reported by our group previously, and we are currently pursuing the effect of TRPV2 channels as modulators of contractility in response to stressors (such as ischemia). There is some evidence outside of the cardiovascular system that describe the TRPV2 channels mostly in the intracellular compartments of uroepithelial cells, pancreatic cells and neuroendocrine cells and have been found to be activated and/or translocated to the cell membrane after stretch stimulation. While this study did not seek to address the role of TRPV2 in this process, the present results demonstrate that the effect of probenecid on the heart is enhanced in ischemically damaged myocardium. This is consistent with previous studies demonstrating that TRPV2 translocation and activation are stress mediated (i.e via stretch, increased cAMP) and may be a useful compensatory mechanism after injury.

As further evidence for the use of probenecid as a potential therapeutic agent in I/R, it was also demonstrated that treatment with oral probenecid decreases deterioration of cardiac function (as evidenced by less ventricular dilation and improved systolic function) in comparison to sham treated mice.

The second critical finding of this study was the lack of cellular damage that probenecid caused both in vivo and in vitro. This is a dramatic finding as the vast majority of the clinically available inotropes have been found to increase mortality and stimulate cardiotoxic pathways resulting in increased infarct size and apoptosis. However, even high dose therapy did not result in significant cell death (compared to untreated water) in vivo after 2 weeks of therapy or in vitro at several different time points and at substantially higher concentrations than would be achieved when administered clinically). This finding may be potentially important, as only digoxin can be used as a positive inotrope over prolonged periods of time orally, though it requires tight monitoring as it has a very narrow therapeutic window. This is in stark contrast to probenecid that has a very positive safety profile over decades and as the present data show, is safe in a murine model when administered even at very high doses.

In summary, the present data present the next step in a translational process that began with the interesting finding that probenecid is a positive inotropic drug. The data demonstrate that probenecid improves function following I/R injury and does not induce an apoptotic response in vivo or in vitro. These findings, together with the previous work presented in Example 1 documenting a β-AR-independent mechanism for probenecid, indicate that probenecid may be safely used to treat heart failure in humans.

EXAMPLE 3

Probenecid induces increased intracellular calcium concentrations without an increase in cell death in HL-1 cells in vitro. We confirmed that probenecid increases intracellular calcium and does not damage cardiac cells. This is in contrast to isoproterenol (commonly used beta-agonist) that also increases contractility but clearly results in increased cell death at clinically relevant concentrations. Even at supraphysiological concentrations, probenecid has causes no cell death, and in fact, there is a trend towards enhanced cell survival. We believe this is due to the fact that probenecid nudges the heart by small increases in intracellular calcium without activating pro-cell death pathways. In contrast, isoproterenol causes signaling that both increases calcium levels more drastically, and activates pro-cell death and hypertrophic pathways that are known to be injurious. Assessment of activities of some of these pathways demonstrates that probenecid does not activate β-AR-dependent pathways (the target of isoproterenol and dobutamine) and does not change the phosphorylation state of calcium handling proteins that are modulated by isoproterenol to increase calcium levels.

With and without ischemic injury (equivalent of heart attack) in a mouse there is no difference in cardiac cell death between no treatment and probenecid treatment. This confirms that probenecid is safe to use orally (given in water) after a heart attack in mice and supports that probenecid does not enhance cell death even in a high-stress model of injury. Similar studies with β-AR agonists show increased infarct size indicative of additional damage.

Furthermore, the mice treated with probenecid had less ventricular dilation (heart increasing in size) and better function in comparison to those without treatment.

After ischemic injury (heart attack) there is a stronger effect of probenecid (administered intra peritoneal) in mice that have the most damage (i.e. larger infarct regions).

We measured heart function (EF) in mice after injury. The lower the EF was after myocardial infarction (MI) the more potent the inotropic effect. This lends credence to its use in ischemically damaged hearts and suggests that even lower doses may be effective in injured or failing hearts.

Probenecid improves function in a healthy porcine model as measured via echocardiography when administered via continuous drip at 5 mg/kg/hr (first 60 minutes) and 10 mg/kg/hr (second thirty minutes). This effect was also seen when probenecid was given at a bolus of 5 mg/kg IV.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the general inventive concept.

What is claimed is:

1. A method of treating acute decompensated heart failure in a subject comprising intravenously infusing probenecid to achieve a probenecid plasma concentration effective to treat acute decompensated heart failure in the subject maintained for 18 to 24 hours, wherein the subject is treated for at least one week.

2. The method of claim 1 using bolus or continuous infusion.

3. The method of claim 1 where a dose of probenecid ranges from about 1 mg/kg/day to about 100 g/kg/day.

4. The method of claim 1 wherein a dose of probenecid is administered over a period of about 10 minutes per day to about 24 hours per day.

5. The method of claim 1 wherein the subject is treated for a least one month.

6. The method of claim 1 comprising an initial probenecid bolus at 1 mg/kg to 50 mg/kg.

7. The method of claim 1 wherein probenecid is administered over a period of about 10 minutes per day to about 24 hours per day.

8. The method of claim 1 wherein infusion is by a metered pump.

9. The method of claim 1 where probenecid is a free acid.

10. The method of claim 1 where probenecid is a sodium salt.

11. A method of treating acute decompensated heart failure in a patient in need thereof, the method of comprising administering to the patient an initial bolus of probenecid at 1 mg/kg to 50 mg/kg followed by intravenous infusion of probenecid at about 1 mg/kg/day to about to 100 mg/kg/day over a period of about 10 minutes per day to about 24 hours per day to result in treating acute decompensated heart failure in the patient.

12. A method of treating acute decompensated heart failure in a patient in need thereof, the method comprising administering to the patient by intravenous infusion a therapeutically effective concentration of probenecid at about 1 mg/kg/day to about 100 mg/kg/day over a period of about 10 minutes per day to about 24 hours per day.

\* \* \* \* \*

UNITED STATES PATENT AND TRADEMARK OFFICE
CERTIFICATE OF CORRECTION

Page 1 of 3

PATENT NO. : 10,806,711 B2
APPLICATION NO. : 13/584713
DATED : October 20, 2020
INVENTOR(S) : Jack Rubinstein et al.

It is certified that error appears in the above-identified patent and that said Letters Patent is hereby corrected as shown below:

On the Title Page

Column 2, Line 10 of Abstract, "levels," should be --level,--.

Page 2, Column 2, Line 44, "Annais" should be --Annals--.

Page 3, Column 2, Line 42, "arrhtyhmias" should be --arrhythmias--.

Page 4, Column 1, Line 39, "Damaga" should be --Damage--.

In the Specification

Column 1, Line 39, "ans" should be --and--.

Column 2, Line 6, "was" should be --were--.

Column 3, Line 5, "with a quantifiable clinical observations" should be --with quantifiable clinical observations--.

Column 3, Line approx. 11, "direct" should be --directed--.

Column 3, Lines 29-30, "with a quantifiable clinical observations" should be --with quantifiable clinical observations--.

Column 5, Line 38, "probenecid" should be --probenecid.--.

Column 5, Line 41, "water treated mice" should be --water treated mice.--.

Column 5, Line 46, "probenecid" should be --probenecid.--.

Signed and Sealed this
Twelfth Day of January, 2021

Andrei Iancu
*Director of the United States Patent and Trademark Office*

CERTIFICATE OF CORRECTION (continued)
U.S. Pat. No. 10,806,711 B2

Column 6, Line 28, "allow" should be --allows--.

Column 6, Line 32, "indeed lower the doses of" should be --indeed lower than doses of--.

Column 6, Line 55, "with a quantifiable clinical observations" should be --with quantifiable clinical observations--.

Column 7, Line 44, "may be desired to a treat a subject." should be --may be desired to treat a subject.--.

Column 7, Lines 64-65, "administering via oral administration of a therapeutically effective dose" should be --administering via oral administration a therapeutically effective dose--.

Column 8, Line 31, "with a quantifiable clinical observations" should be --with quantifiable clinical observations--.

Column 9, Line 10, "with a quantifiable clinical observations" should be --with quantifiable clinical observations--.

Column 10, Line 7, "as well as," should be --as well as--.

Column 12, Line 14, "was measured" should be --were measured--.

Column 15, Line 41, "+dL/dt and –dL/dt)." should be --+dL/dt and –dL/dt.--.

Column 18, Line 38, "were done" should be --was done--.

Column 18, Line 48, "1 µM)" should be --1 µM--.

Column 19, Line 7, "was determined" should be --were determined--.

Column 20, Line 39, "comparisons." should be --comparisons).--.

Column 22, Line 20, "probenecid," should be --probenecid--.

Column 22, Line 60, "clinically)." should be --clinically.--.

Column 23, Line 20, "causes" should be --caused--.

In the Claims

Column 24, Line 59 (Claim 3), "100 g/kg/day." should be --100 mg/kg/day.--.

Column 24, Line 65 (Claim 5), "a least" should be --at least--.

Column 25, Line 10 (Claim 11), "method of comprising" should be --method comprising--.

CERTIFICATE OF CORRECTION (continued)
U.S. Pat. No. 10,806,711 B2

Column 25, Line 13 (Claim 11), "1 mg/kg/day to about to 100 mg/kg/day" should be --1 mg/kg/day to about 100 mg/kg/day--.

SEQUENCE LISTING

```
<160> NUMBER OF SEQ ID NOS: 2

<210> SEQ ID NO 1
<211> LENGTH: 18
<212> TYPE: DNA
<213> ORGANISM: Mus musculus

<400> SEQUENCE: 1
ctactgctca acatgctc                                              18

<210> SEQ ID NO 2
<211> LENGTH: 19
<212> TYPE: DNA
<213> ORGANISM: Mus musculus

<400> SEQUENCE: 2
ctcatcaggt ataccatcc                                             19
```